(12) United States Patent
Tsunoda et al.

(10) Patent No.: US 6,670,447 B2
(45) Date of Patent: Dec. 30, 2003

(54) AMINO ACID N-CARBOXYANHYDRIDES WITH ACYL SUBSTITUENTS ON NITROGEN ATOMS THEREOF

(75) Inventors: Hidetoshi Tsunoda, Chiba (JP); Michiru Sekiguchi, Chiba (JP); Hajime Iizuka, Chiba (JP); Kazuya Sakai, Chiba (JP)

(73) Assignee: Mitsui Chemicals, Inc., Tokyo (JP)

( * ) Notice: Subject to any disclaimer, the term of this patent is extended or adjusted under 35 U.S.C. 154(b) by 18 days.

(21) Appl. No.: 10/070,156

(22) PCT Filed: Jul. 4, 2001

(86) PCT No.: PCT/JP01/05780

§ 371 (c)(1),
(2), (4) Date: Mar. 4, 2002

(87) PCT Pub. No.: WO02/02538

PCT Pub. Date: Jan. 10, 2002

(65) Prior Publication Data

US 2002/0173664 A1 Nov. 21, 2002

(30) Foreign Application Priority Data

Jul. 4, 2000 (JP) .......................... 2000-201745
Oct. 3, 2000 (JP) .......................... 2000-303522

(51) Int. Cl.$^7$ .............................. C07K 16/00
(52) U.S. Cl. .................. 530/323; 530/334; 530/335; 548/226
(58) Field of Search ................ 530/335, 334, 530/323; 548/226

(56) References Cited

U.S. PATENT DOCUMENTS 4,946,942 A * 8/1990 Fuller et al. ............... 548/183

FOREIGN PATENT DOCUMENTS

JP 48-86886 11/1973
WO WO 89/08643 A1 9/1989

OTHER PUBLICATIONS

Theodora W. Greene, 1982, Wiley–Interscience Publication, "Protective Groups in Organic Synthesis", 218–287.*
Cosani et al, 1967, "Poly[iminocarbonyl[3–[(benzyloxy)carbonyl]propylidene]], .alpha.–[3–carboxy–1–[[4–(2–carboxyethyl)–2,5–dioxo–3–oxazolidinyl]carbonyl]propyl]–.omega.–amino–dibenzyl ester"; CA:67:32972.*
Savrda et al, 1994, "2,5–Oxazolidinedione, 3–benzoyl–4(2–methylpropyl)–, (S)–"; CA:122:10484.*
Tobiki et al. 1973, "2,5–Oxazolidinedione, 4–(1, 4–cyclohexadien–1–yl)–3–(1,3–dioxobutyl)–"; CA: 80:146150.*
Tobiki et al, 1980, "2,5–Oxazolidinedione, 3–(1,3–dioxobutyl)–"; CA:80:146150.*
Cosani et al, 1967, "Poly[iminocarbonyl[3–[(benzyloxy)-carbonyl]propylidene]],.alpha.–[3–carboxy–1–[[4–(2–carboxyethyl)–2,5–dioxo–3–oxazolidinyl]carbonyl]-propyl]–.omega.–amino–dibenzyl ester"; CA:67:329724.*
Savrda et al, "Activation of N,N–bis(alkoxycarbonyl) Amino acid. Synthesis of N–alkoxycarbonyl amino acid N–carboxyanhydrides and N,N–Dialkoxycarbonyl Amino acid Fluorides . . . " Elsevier Science Ltd., 1994, 50:5309–5322.*
Tobiki et al, 1980, "2,5–Oxazolidinedione, 3–(1, 3–dioxobutyl)–4–phenyl–, (R)–" CA:93:114382.*
Chem. Abs., vol. 77, 20166(b), (1972) Registry No. 34895–29–9.
M. Wakselman et al., *Urethane Protected Amino Acid N–Carboxyanhydrides and Fluorides (U–NCAs and U2AAFs)*, (1994), 7(1), pp 67 to 77.

* cited by examiner

*Primary Examiner*—Alan L. Rotman
*Assistant Examiner*—Robert Shiao
(74) *Attorney, Agent, or Firm*—Burns, Doane, Swecker & Mathis, LLP

(57) ABSTRACT

This invention provides amino acid N-carboxyanhydrides, each of which has an N-acyl substituent on its nitrogen atom, is represented by the following formula (1):

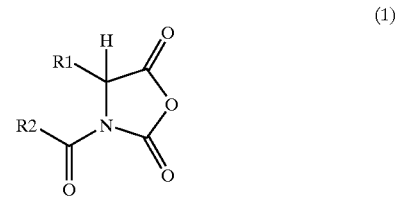

readily reacts with nucleophilic reagents such as free amino acids, alcohols, anions or the like, and are intermediates useful for the high-yield production of amino acid derivatives, optically active compounds, peptides, polypeptides and the like useful in many fields lead by the fields of pharmaceuticals and agrochemicals, and also provides a process for the production of the amino acid N-carboxyanhydrides. Further, the present invention also provides a process for the production of diamides, which uses the compounds of the formula (1) and amine derivatives represented by the following formula (7):

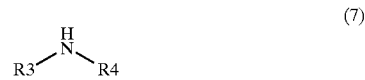

These diamides can also be suitably used for the production of amino acid derivatives, optically active compounds, peptides, polypeptides and the like.

9 Claims, No Drawings

US 6,670,447 B2

AMINO ACID N-CARBOXYANHYDRIDES WITH ACYL SUBSTITUENTS ON NITROGEN ATOMS THEREOF

TECHNICAL FIELD

This invention relates to activated amino acid derivatives which are important intermediates useful in many fields led by the fields of pharmaceuticals and agrochemicals. The present invention is also concerned with novel amino acid N-carboxyanhydrides each of which has a substituent of the N-acyl type on a nitrogen atom thereof, and also with a process for the production of diamides, which makes use of the amino acid N-carboxyanhydrides, requires fewer steps and is economical.

BACKGROUND ART

Amino acids are available rather readily at low prices and have diverse structures and asymmetric carbon atoms, so that they have been widely used for many years as raw materials or the like for a variety of optically active compounds led by peptides. In particular, production technology of peptides, which uses amino acids as raw materials, has been one of important basic technologies for many years in many fields led by the fields of pharmaceuticals and agrochemicals. Keeping in step with the advance of molecular biology in recent years, the importance of peptides tends to increase progressively. There is, accordingly, an outstanding demand for an economical production process of peptides, which is suited for industrial practice on large scale.

The principle of peptide production resides a reaction in which a carboxyl group of an amino acid and an amino group of an amine derivative, which may be an amino acid, are subjected to dehydrating condensation to form an amide bond. In practice, however, a free amino acid becomes an ampholytic ion, forms an internal salt and is stabilized, so that the above-mentioned reaction does not occur spontaneously. Even if the reaction should proceed, high-yield production of a specific target product cannot be expected because the amino groups contained in the respective reactants are free and many dipeptides, diketopiperazine derivatives and the like are hence byproduced.

To obtain the target peptide with good yield, functional groups other than those needed have to be masked beforehand to prevent occurrence of undesired reactions. In the case of a methyl ester or the like, its reaction velocity is low and impractical so that a carboxyl component must be activated suitably. A protecting group used as a mask not only plays a role to prevent a side reaction but also has an effect to reduce the polarity of the amino acid and to render it more readily soluble in an organic solvent.

Examples of the protecting group can include urethane-type protecting groups such as tert-butoxycarbonyl (Boc) group and benzyloxycarbonyl (Z) group, alkyl-type protecting groups such as trityl group, and acyl-type protecting groups such as formyl group, tosyl group, acetyl group and benzoyl group. In these protecting groups, urethane-type protecting groups can hardly induce racemization [Jiro Yajima, Yuki Gosei Kyokai Shi (Journal of Synthetic Organic Chemistry, Japan), 29, 27 (1971); Noboru Yanaihara, Pharmacia, 7, 721 (1972)], but acyl-type and alkyl-type protecting groups are accompanied by a drawback that they tend to induce racemization. Further, alkyl-type protecting groups do not fully mask the basicity of an amino group so that the amino group may still be subjected to further acylation. With a trityl group, no second acylation can take place owing to its steric hindrance. Conversely, this steric hindrance makes it difficult to achieve introduction itself of a trityl group, and further, it is not easy to conduct a condensation reaction between a trityl-protected amino acid with and a trityl-protected amine.

A synthesis process which includes introduction of protecting groups requires protecting and deprotecting steps, each of which requires a costly reagent, and also purification steps after the protecting and deprotecting groups, respectively. This synthesis process, therefore, results in multi-step production, leading to an increase in cost.

If it is difficult to allow a condensation reaction to proceed easily between an amino acid and an amine, there are processes in each of which a carboxyl group of an amino acid derivative with a protected amino group is activated by an electron-attracting substituent to facilitate its nucleophilic attack on the carbon atom of a carbonyl group of the amine. Illustrative of these processes are the acid chloride process in which an activated amino acid is derived using $PCl_5$, $PCl_3$ or thionyl chloride, the azidation process in which an activated amino acid is derived from an amino acid ester or the like via a hydrazide, the mixed acid anhydride process in which an activated amino acid is derived from a protected amino acid and another acid, and the crosslinking process making use of a conventional condensing agent such as N,N'-dicyclohexylcarbodiimide (DCC) or 1,1-carbonyldiimidazole (hereinafter abbreviated as "CDI"). However, the acid chloride process involves a problem that many side reactions occur, the azidation process is accompanied by a problem that the derivation into an azide is very cumbersome, and the mixed acid anhydride process has a problem that disproportionation tends to occur when the temperature rises ("Peptide Synthesis" written by Nobuo Izumiya et al.). The process making use of a condensing agent is also accompanied by some drawbacks. In the case of DCC, for example, an acylisourea which is an intermediate formed by a reaction between a carboxyl group and DCC may undergo an intermolecular rearrangement in the presence of a base to form an acylurea, thereby lowering the yield of the target product or making it difficult to separate the acylurea from the target product. Further, DCC dehydrates the ω-amide of asparagine or glutamine to form a nitrile. On the other hand, CDI is an expensive reagent, and the crosslinking process making use of CDI is not considered to be an economical production process of peptides.

As described above, many peptide production processes have been studied. To be industrially stable production technology or low-cost production technology, however, these processes have to be considered to be still insufficient.

On the other hand, amino acid N-carboxyanhydrides (referred to as "NCAs" when abbreviated) which have been studied as active amino acids readily react with most free amines. Primary merits of NCAs include that they themselves are effective acylating agents ("Peptides", 9, 83) and that they permit more economical production through fewer steps than the commonly-employed crosslinking process making use of a condensing agent such as N,N-dicyclohexylcarbodiimide or 1,1-carbonyldiimidazole or the N-hydroxysuccinimide ester crosslinking process. In addition, these amino acid NCAs do not develop the problem of racemization or the like of amino acids under reaction conditions commonly employed for the production of peptides. NCAs have, therefore, been expected for many years to serve as important intermediates for the synthesis of peptides [Pheiol Chem., 147, 91 (1926)].

The peptide synthesis which uses an N-unsubstituted NCA as a production intermediate and has been known well for many years, however, involves many problems in that side reactions such as a polymerization reaction are always hardly controllable and the reactivity and stability differ depending on the kinds of the reactants. This peptide synthesis, therefore, has not been considered as a common peptide production process although its potential utility has been recognized. With a view to solving these problems, numerous improvements have been made. For example, Bailey et al. reported an illustrative condensation reaction between L-alanine-NCA and glycine under low temperature (−40° C.) conditions in an organic solvent [J. Chem. Soc., 8461 (1950)]. Further, Robert G. D. et al. reported illustrative production of a dipeptide under 0 to 5° C. conditions in an aqueous solution (around pH 10) by using L-phenylalaline-NCA [J. Am. Chem. Soc., 88, 3163 (1966)]. In addition, Thomas J. B. et al. reported potential industrial utility of a condensation reaction making use of L-alanine-NCA and L-proline [J. Org. Chem., 53, 836 (1988)].

Despite these efforts, however, N-unsubstituted NCAs are very limited in conditions optimal for the prevention of a polymerization reaction and racemization reaction as side reactions and are not suited from the industrial viewpoint.

Accordingly, efforts have been made in attempts to solve problems in polymerization control and the like by introducing a substituent of the N-alkyl or N-sulfenyl type onto a nitrogen atom of an NCA. Reported in patents and other technical publications include, for example, N-methyl-NCA, N-ethyl-NCA, N-nitrophenylsulfenyl-NCA [Kricheldorf et al., Angew. Chem. Acta 85, (1978) 86], N-xanthyl-NCA [Halstroem and Kovacs et al., Acta Chemica Scandvnavia, Ser. B, 1986, BYO(6), 462; U.S. Pat. No. 4,267,344], and N-trityl-NCA (Block and Cox et al., "Peptides, Proc. of the 5$^{th}$ Europ. Symp., Oxford, September 1962, Pergramon Press 1963, Compiled by G. T. Young, page 84". However, production processes of these compounds themselves lack general applicability, and effects of these compounds for polymerization control and the like are not sufficient. These compounds, therefore, have not lead to solution of the fundamental problems.

In 1980's, it was attempted to control the reactivity of an NCA by introducing a trimethylsilyl group onto the nitrogen atom of the NCA. This control was practiced with glycine-NCA (Bayer AG, DE 1768871). This approach indicated possibility of suppressing a polymerization reaction which was considered to be one of serious side reactions, but involves a problem in stability and a problem of an increase in production cost, and its application to other amino acids has not been made since then. The idea of introducing a substituent onto a nitrogen atom was subsequently applied by Palomo C. et al. to a condensation reaction between a non-natural amino acid and an amine by using a NCA in which a nitrogen atom is protected by a benzyl group [Chem. Commun., 7, 691 (1997); Tetrahedron Lett., 38(17), 3093 (1997)]. However, these processes are also accompanied by problems in that the target NCA cannot be produced economically due to the need for many steps for its synthesis and a limitation is imposed on amino acids which can be synthesized.

In recent years, N-substituted NCAs with substituents of the urethane type as substituents on nitrogen atoms were reported. Firstly, Kricheldolf et al. reported a process for the production of N-methoxycarbonylglycine-NCA and N-ethoxycarbonylglycine-NCA [Macromol. Chem., 178, 905 (1977)]. Then, Fuller et al. reported production of N-urethane-substituted NCA and N-urethane-substituted thiocarboxylic acid anhydride from amino acids other than glycine (Bioresearch Inc., JP 2875834 B). They admirably solved the problem of polymerization control or the like by using these N-urethane-substituted NCAs. They, however, used costly N-urethane groups as amino-protecting groups, thereby failing to make good use of the merit of NCAs that amide compounds can be produced through fewer steps at low cost without using protecting groups. Further, they did not conduct any study on N-substituted NCAs other than N-urethane-substituted NCAs and made no mention about N-acyl-substituted NCAs.

An N-acyl-substituted NCA, on the other hand, is expected to provide a short and economical process for forming an amino acid into a derivative thereof because use of a target amide structure as a substituent in NCA prevents side reactions such as polymerization and obviates protection and deprotection. For example, a reaction with a desired amine has possibility of synthesizing a diamide compound at low cost without steps such as bonding and elimination of a protecting group to and from an amino group.

Only an extremely limited number of reports have, however, been made on the synthesis of N-acyl-substituted NCAs. Moreover, none of these synthesis processes are equipped with general applicability. For example, Kricheldolf et al. reported 3-(3,5-dinitrobenzoyl)-4,4-dimethyl-2,5-oxazolinedinedione in the article referred to in the above [Macromol. Chem., 178, 905 (1977)]. This is the only example reported by them concerning N-acyl-substituted NCAs. In addition, the amino acid employed in their report is di-substituted at the a-position and contains no asymmetric carbon atom, and their report does not disclose any N-acyl-substituted NCA with other acyl group. Accordingly, their process is poor in wide applicability.

N-(3-oxobutanoyl)-substituted NCAs, on the other hand, are reported in JP 48-86886 A. The substituent on the nitrogen atom is, however, limited only to an N-(3-oxobutanoyl) group introduced using a diketene in their production process, so that this process cannot introduce acyl groups which are widely used. Concerning the compounds represented by the formula (2) and the formula (3), respectively, no synthesis process is disclosed [M. Wakselman et al., Amino Acids, 7, 67–77 (1994); Reibel Leonard et al., Bull. Soc. Chim. Fr., 3, 1025–319 (1972)]. These articles disclose only the structures of such compounds, and therefore, no synthesis is feasible following the articles.

As described above, many of conventional reports are directed to alkyl- or urethane-substituted NCAs, and production and use of N-acyl-substituted NCAs are still considered to be very difficult or impossible although they are expected to have high utility ["Peptides, Proc. of the 5$^{th}$ Europ. Symp., Oxford, September 1962", Pergamon Press 1963, Compiled by G. T. Young, Pages 84–87; Yonezawa et al., "Yuki Gosei Kagaku (Synthetic Organic Chemistry)", 47(9), 782–794 (1989)].

In short, N-acyl-substituted NCAs and various amino acid derivatives produced by amidation reactions making use of these NCAs are expected to find utility as useful compounds or production processes in many fields led by the fields of pharmaceuticals and agrochemicals. Nonetheless, neither commonly applicable production process of N-acyl-substituted NCAs nor widely applicable, industrially-excellent peptide production process making use of these NCAs were known practically to date.

DISCLOSURE OF THE INVENTION

Objects of the present invention is to provide a novel amino acid N-carboxyanhydride with an N-acyl substituent on a nitrogen atom thereof, which is considered to be an important intermediate extremely useful in many fields led by the fields of pharmaceuticals and agrochemicals but cannot be obtained by the conventional production techniques, and its production process, and a production process of a diamide compound, which owing to use of the N-carboxyanhydride, does not develop problems such as racemization, includes fewer steps and is economical.

The present inventors have proceeded with an extensive investigation to achieve the above-described objects. As a result, they have succeeded in obtaining a novel amino acid N-carboxyanhydride with an N-acyl substituent on a nitrogen atom thereof and based on use of the compound, have also found a novel amidation reaction which does not develop problems such as racemization, leading to the completion of the present invention.

Described specifically, an amino acid N-carboxyanhydride with a substituent on a nitrogen atom thereof according to the present invention has a structure represented by the following formula (1):

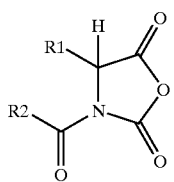

(1)

wherein $R^1$ and $R^2$ each independently represents a substituted or unsubstituted alkyl group, a substituted or unsubstituted cycloalkyl group, a substituted or unsubstituted aralkyl group, a substituted or unsubstituted aryl group, a substituted or unsubstituted heterocycle, or a substituted or unsubstituted heterocyclic alkyl group.

Examples of the invention compound represented by the formula (1) can include the following compounds:

1. Among compounds represented by the formula (1), those falling within neither the following category A nor the following category B:
   A. Compounds of the formula (1) in which $R^2$ is a 2-oxopropyl group; and
   B. Compounds of the following formulas (2) and (3):

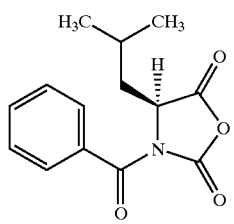

(2)

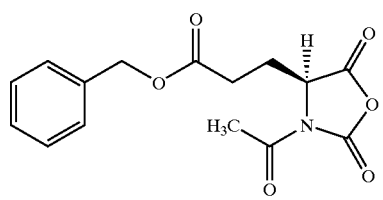

(3)

2. Compounds of the formula (1) in which $R^2$ is a substituted or unsubstituted alkyl group, a substituted or unsubstituted cycloalkyl group, or a substituted or unsubstituted aralkyl group.

3. Compounds of the formula (1) in which $R^2$ is a substituted or unsubstituted alkyl group, a substituted or unsubstituted cycloalkyl group, or a substituted or unsubstituted aralkyl group, with a proviso that the compounds falling within the above category A or B are excluded.

4. Compounds of the formula (1) in which $R^2$ is a substituted or unsubstituted aryl group.

5. Compounds of the formula (1) in which $R^2$ is a substituted or unsubstituted aryl group, with a proviso that the compounds falling within the above category B are excluded.

6. Compounds of the formula (1) in which $R^2$ is a substituted or unsubstituted heterocycle or a substituted or unsubstituted heterocyclic alkyl group.

7. Compounds of the formula (1) in which $R^1$ is a side chain on an α-carbon atom of a protected or unprotected amino acid.

8. Compounds having any one of the structures described above under items 1–6, in which $R^1$ is a side chain on an α-carbon atom of a protected or unprotected amino acid.

A process according to the present invention for the production of the compound represented by the formula (1), in a first aspect thereof, comprises reacting, in an inert diluent and in the presence of a condensing agent, an amino acid N-carboxyanhydride represented by the following formula (4):

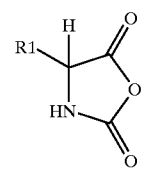

(4)

wherein $R^1$ has the same meaning as defined in claim 1 with a compound represented by the following formula (5):

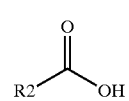

(5)

wherein $R^2$ has the same meaning as defined in claim 1.

The process according to the present invention for the production of the compound represented by the formula (1), in a second aspect thereof, comprises reacting, in an inert diluent and in the presence of an amine base, an amino acid N-carboxyanhydride represented by the following formula (4):

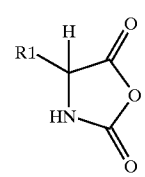

(4)

wherein $R^1$ has the same meaning as defined in claim 1 with a compound represented by the following formula (6):

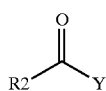

(6)

wherein R² has the same meaning as defined in claim 1 and Y represents a halogen atom.

A process according to the present invention for the production of an amide derivative represented by the following formula (8):

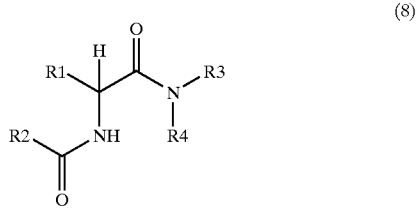

(8)

wherein R¹ and R² have the same meanings as defined above, and R³ and R⁴ each independently represents a hydrogen atom, a substituted or unsubstituted alkyl group, a substituted or unsubstituted cycloalkyl group, a substituted or unsubstituted aralkyl group, a substituted or unsubstituted aryl group, a substituted or unsubstituted heterocycle, or a substituted or unsubstituted heterocyclic alkyl group, which comprises a step of reacting a compound represented by the formula (1), for example, any one of the compounds exemplified above under items 1–8 with an amine derivative represented by the following formula (7):

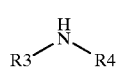

(7)

wherein R³ and R⁴ have the same meanings as defined above.

The process according to the present invention for the production of the compound represented by the formula (8), in another aspect thereof, comprises a step of reacting a compound represented by the formula (1), for example, any one of the compounds exemplified above under items 1–8 with an unprotected or protected amino acid.

BEST MODES FOR CARRYING OUT THE INVENTION

The compounds according to the present invention will next be described in further detail.

The term "substituted or unsubstituted alkyl group" represented by R¹, R², R³ and R⁴ in the formulas (1), (4), (5), (6), (7) and (8) means an alkyl group which may be substituted at one or more desired parts thereof. Examples of the alkyl group can include methyl, ethyl, methoxyethyl, phenoxymethyl, benzyloxymethyl, methylthiomethyl, phenylthiomethyl, fluorenylmethyl, fluoroethyl, n-propyl, chloropropyl, isopropyl, n-butyl, (substituted amino)-n-butyl, isobutyl, sec-butyl, tert-butyl, pentyl, hexyl, heptyl, octyl, nonyl, and decyl.

The term "substituted or unsubstituted cycloalkyl group" means a cycloalkyl group which may be substituted at one or more desired parts thereof. Examples of the cycloalkyl group can include cyclopropyl, cyclobutyl, cyclopentyl, ethoxycyclopentyl, cyclohexyl, tert-butoxycyclohexyl, benzyloxycyclohexyl, nitrocyclohexyl, cycloheptyl, cyclooctyl, cyclononyl, and cyclodecyl.

The term "substituted or unsubstituted aralkyl group" means an aralkyl group which may be substituted at one or more desired parts thereof. Examples of the aralkyl group can include benzyl, 2-phenylethyl, 3-phenylpropyl, cinnamyl, naphthylmethyl, 3-chlorobenzyl, 4-aminobenzyl, 2-nitrobenzyl, 4-methoxybenzyl, 3,4-dihydroxybenzyl, and 3,4-dimethoxybenzyl.

The term "substituted or unsubstituted aryl group" means an aryl group which may be substituted at one or more desired parts thereof. Examples of the aryl group can include phenyl, tolyl, bromophenyl, methoxyphenyl, ethylphenyl, propylphenyl, nitrophenyl, amidophenyl, fluorenyl, naphthyl, hydroxynaphthyl, anthracenyl, phenanthrenyl, and benzophenanthrenyl.

The term "substituted or unsubstituted heterocycle" means a heterocycle which may be substituted at one or more desired parts thereof. Examples of the heterocycle can include tetrahydropyranyl, tetrahydrofuranyl, alkyltetrahydrofuranyl, tetrahydrothienyl, methylsulfonyltetrahydrothienyl, pyridyl, pyrazyl, pyrimidyl, thienyl, hydroxypyridyl, imidazolyl, thiazolyl, pyrazolyl, pyrazolonyl, isoxazolyl, isothiazyl, pyrrolyl, furanyl, naphthylidinyl, quinolyl, sulfamoylquinolyl, and sydononyl.

The term "substituted or unsubstituted heterocyclic alkyl group" means a heterocyclic alkyl group which may be substituted at one or more desired parts thereof. Examples of the heterocyclic alkyl group can include 3-pyridylmethyl, 4-pyridylmethyl, 6-methoxy-3-pyridylmethyl, 3-quinolylmethyl, N-methyl-4-imidazolemethyl, 2-amino-4-thiazolemethyl, and morpholinomethyl.

The term "side chain on an α-carbon atom of a protected or unprotected amino acid" means a side chain on an α-carbon atom of an amino acid such as alanine or valine, leucine, isoleucine, tert-leucine, serine, threonine, aspartic acid, glutamic acid, asparagine, glutamine, lysine, hydroxylysine, arginine, cysteine, cystine, methionine, phenylalanine, tyrosine, tryptophan, histidine, homoserine or ornithine, for example. Representative examples of the side chain can include those represented by the following formulas (9) to (29):

(9)

(10)

(11)

(12)

(13)

-continued

(14) 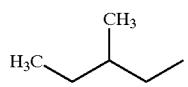

(15) 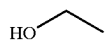

(16) 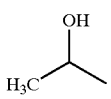

(17) 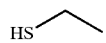

(18) 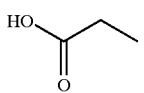

(19) 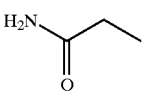

(20) 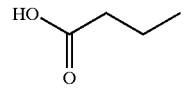

(21) 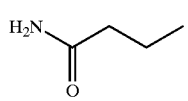

(22) 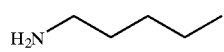

(23) 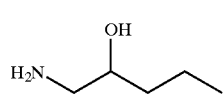

(24) 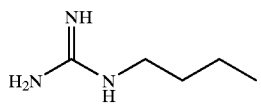

(25) 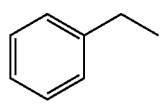

(26) 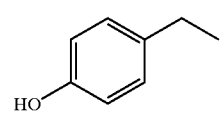

(27) 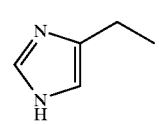

(28)

-continued

(29) 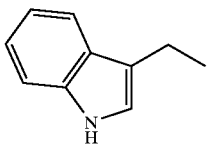

The above-described side chains may be protected with protecting groups by methods, both of which are known commonly to those having ordinary skill in the art, as desired. For example, they may be protected using a commonly-employed, amino-protecting group, thiol-protecting group or carboxy-protecting group.

Illustrative inert diluents, which are usable in the first and second aspects of the process according to the present invention for the production of the compound represented by the formula (1), are chlorine-containing organic solvents such as methylene chloride, chloroform, carbon tetrachloride, dichloroethane and tetrachloroethane; esters such as methyl acetate, ethyl acetate and butyl acetate; ethers such as diethyl ether, diphenyl ether, dioxane and tetrahydrofuran; and hexane, liquid sulfur dioxide, carbon disulfide, benzene, toluene, xylene, nitromethane, nitrobenzene, acetonitrile, dimethylformamide, dimethylacetamide, and 1,3-dimethyl-2-imidazolidinone. They can be used either singly or in combination as needed.

Examples of the condensing agent can include thionyl chloride, thionyl bromide, N,N-dicyclohexylcarbodiimide, and 1,1-carbonyldiimidazole. They can be used either singly or in combination as needed.

Examples of the halogen atom represented by Y in the formula (6) can include a chlorine atom, bromine atom and iodine atom.

Illustrative of the amine base are trimethylamine, triethylamine, tributylamine, diisopropylethylamine, pyridine, lutidine, N,N-dimethylaniline, N,N-dimethyltoluidine, 4-dimethylaminopyridine, N-methylmorpholine, diazabicycloundecene, and 1,8-bis(dimethylamino)-naphthalene.

Examples of the protected or unprotected amino acid usable as an amine in the production process of the compound of the formula (8) can include alanine, valine, leucine, isoleucine, tert-leucine, serine, threonine, aspartic acid, glutamic acid, asparagine, glutamine, lysine, hydroxylysine, arginine, cysteine, cystine, methionine, phenylalanine, tyrosine, tryptophan, histidine, homoserine, and ornithine. They can be used either singly or in combination as needed.

When the invention derivative represented by the formula (1) contains one or more asymmetric carbon atoms, the derivative may exist in the form of a specific stereoisomer or in the form of a mixture of stereoisomers including a racemic form.

Compounds encompassed by the formula (1) will be exemplified in Table 1 to Table 46, although they shall by no means restrict the compound according to the present invention. Incidentally, "Ph" in the tables means "a phenyl group" or "a phenylene group".

TABLE 1
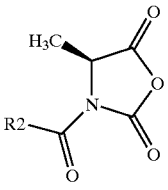
| Compound No. | R2 | Compound No. | R2 |
|---|---|---|---|
| 1001 | CH3 | 1045 |  |
| 1002 | CH2CH3 | 1046 | 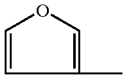 |
| 1003 | (CH2)2CH3 | 1047 | 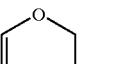 |
| 1004 | CH(CH3)2 | 1048 | 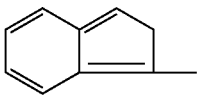 |
| 1005 | (CH2)3CH3 | 1049 | 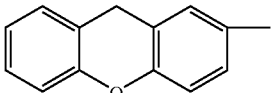 |
| 1006 | CH2CH(CH3)2 | 1050 | 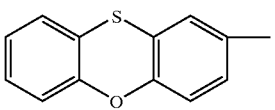 |
| 1007 | CH(CH3)CH2CH3 | 1051 | 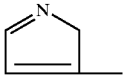 |
| 1008 | C(CH3)3 | 1052 | 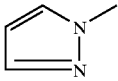 |
| 1009 | (CH2)4CH3 | 1053 | 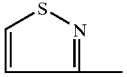 |
| 1010 | (CH2)5CH3 | 1054 | 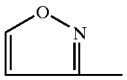 |
| 1011 | (CH2)6CH3 | 1055 | 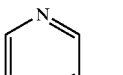 |
| 1012 | (CH2)7CH3 | 1056 | 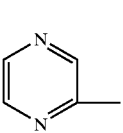 |

TABLE 1-continued
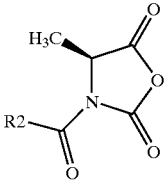
| Compound No. | R2 | Compound No. | R2 |
|---|---|---|---|
| 1013 | (CH2)8CH3 | 1057 | 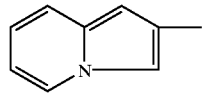 |
| 1014 | cyclopropyl | 1058 | 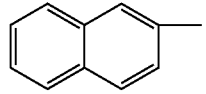 |
| 1015 | cyclobutyl | 1059 | 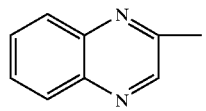 |
| 1016 | cyclohexyl | 1060 | 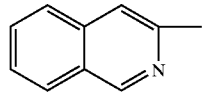 |
| 1017 | Ph | 1061 | 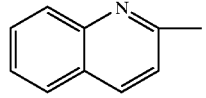 |
| 1018 | PhCH2 | 1062 | 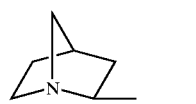 |
| 1019 | Ph(CH2)2 | | |
| 1020 | Ph(CH2)3 | | |
| 1021 | PhO(CH2)2 | | |
| 1022 | PhCH2OCH2CH2 | | |
| 1023 | PhCH2O(C=O)CH2CH2 | | |
| 1024 | o-CH3Ph | | |
| 1025 | m-CH3Ph | | |
| 1026 | p-CH3Ph | | |
| 1027 | 2,4-(CH3)2Ph | | |
| 1028 | 3,5-(CH3)2Ph | | |
| 1029 | 2,4,6-(CH3)3Ph | | |
| 1030 | p-CH3OPh | | |
| 1031 | p-CH3CH2OPh | | |
| 1032 | p-CH3(CH2)2OPh | | |
| 1033 | p-FPh | | |
| 1034 | p-ClPh | | |

TABLE 1-continued
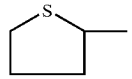
| Compound No. | R2 | Compound No. | R2 |
|---|---|---|---|
| 1035 | p-BrPh | | |
| 1036 | p-IPh | | |
| 1037 | p-PhOPh | | |
| 1038 | p-PhCH2OPh | | |
| 1039 | p-NO2Ph | | |
| 1040 | p-CNPh | | |
| 1041 | p-CH3SO2Ph | | |
| 1042 | 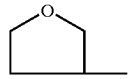 | | |
| 1043 | 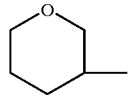 | | |
| 1044 | 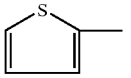 | | |
TABLE 2
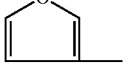
| Compound No. | R2 | Compound No. | R2 |
|---|---|---|---|
| 2001 | CH3 | 2045 | 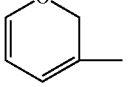 |
| 2002 | CH2CH3 | 2046 | |
| 2003 | (CH2)2CH3 | 2047 | |
| 2004 | CH(CH3)2 | 2048 | 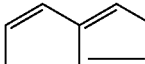 |

TABLE 2-continued
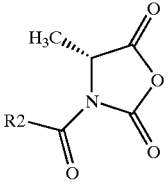
| Compound No. | R2 | Compound No. | R2 |
| --- | --- | --- | --- |
| 2005 | (CH2)3CH3 | 2049 | 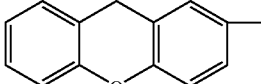 |
| 2006 | CH2CH(CH3)2 | 2050 | 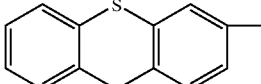 |
| 2007 | CH(CH3)CH2CH3 | 2051 | 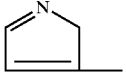 |
| 2008 | C(CH3)3 | 2052 | 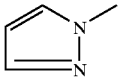 |
| 2009 | (CH2)4CH3 | 2053 | 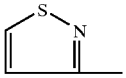 |
| 2010 | (CH2)5CH3 | 2054 | 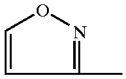 |
| 2011 | (CH2)6CH3 | 2055 | 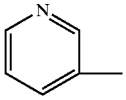 |
| 2012 | (CH2)7CH3 | 2056 | 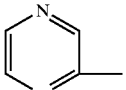 |
| 2013 | (CH2)8CH3 | 2057 | 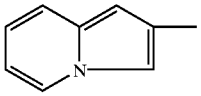 |
| 2014 | cyclopropyl | 2058 | 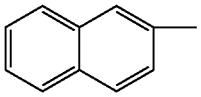 |
| 2015 | cyclobutyl | 2059 | 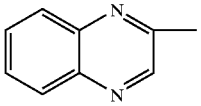 |
| 2016 | cyclohexyl | 2060 | 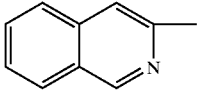 |

TABLE 2-continued
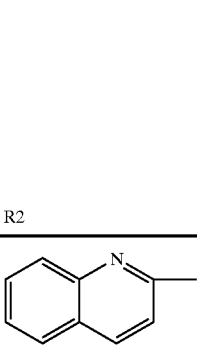
| Compound No. | R2 | Compound No. | R2 |
|---|---|---|---|
| 2017 | Ph | 2061 |  |
| 2018 | PhCH2 | 2062 | 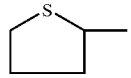 |
| 2019 | Ph(CH2)2 | | |
| 2020 | Ph(CH2)3 | | |
| 2021 | PhO(CH2)2 | | |
| 2022 | PhCH2OCH2CH2 | | |
| 2023 | PhCH2O(C=O)CH2CH2 | | |
| 2024 | o-CH3Ph | | |
| 2025 | m-CH3Ph | | |
| 2026 | p-CH3Ph | | |
| 2027 | 2,4-(CH3)2Ph | | |
| 2028 | 3,5-(CH3)2Ph | | |
| 2029 | 2,4,6-(CH3)3Ph | | |
| 2030 | p-CH3OPh | | |
| 2031 | p-CH3CH2OPh | | |
| 2032 | p-CH3(CH2)2OPh | | |
| 2033 | p-FPh | | |
| 2034 | p-ClPh | | |
| 2035 | p-BrPh | | |
| 2036 | p-IPh | | |
| 2037 | p-PhOPh | | |
| 2038 | p-PhCH2OPh | | |
| 2039 | p-NO2Ph | | |
| 2040 | p-CNPh | | |
| 2041 | p-CH3SO2Ph | | |
| 2042 | 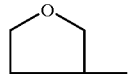 | | |
| 2043 |  | | |

TABLE 2-continued
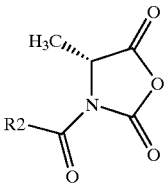
| Compound No. | R2 | Compound No. | R2 |
|---|---|---|---|
| 2044 | 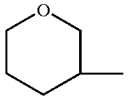 | | |
TABLE 3
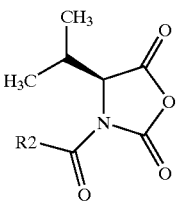
| Compound No. | R2 | Compound No. | R2 |
|---|---|---|---|
| 3001 | CH3 | 3045 | 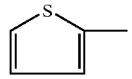 |
| 3002 | CH2CH3 | 3046 | 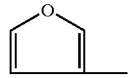 |
| 3003 | (CH2)2CH3 | 3047 | 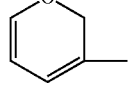 |
| 3004 | CH(CH3)2 | 3048 | 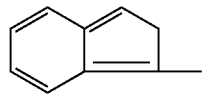 |
| 3005 | (CH2)3CH3 | 3049 | 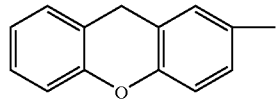 |
| 3006 | CH2CH(CH3)2 | 3050 | 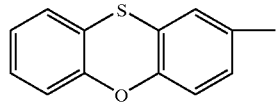 |
| 3007 | CH(CH3)CH2CH3 | 3051 | 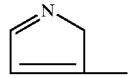 |
| 3008 | C(CH3)3 | 3052 | 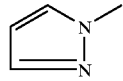 |

TABLE 3-continued
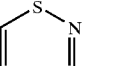
| Compound No. | R2 | Compound No. | R2 |
|---|---|---|---|
| 3009 | (CH2)4CH3 | 3053 | 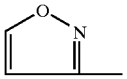 |
| 3010 | (CH2)5CH3 | 3054 | 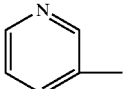 |
| 3011 | (CH2)6CH3 | 3055 | 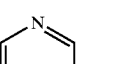 |
| 3012 | (CH2)7CH3 | 3056 | 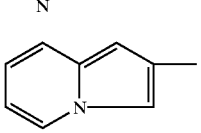 |
| 3013 | (CH2)8CH3 | 3057 | 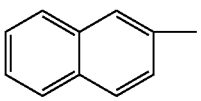 |
| 3014 | cyclopropyl | 3058 | 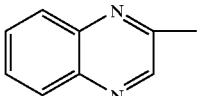 |
| 3015 | cyclobutyl | 3059 | 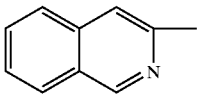 |
| 3016 | cyclohexyl | 3060 | 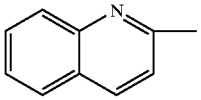 |
| 3017 | Ph | 3061 |  |
| 3018 | PhCH2 | 3062 | |
| 3019 | Ph(CH2)2 | | |
| 3020 | Ph(CH2)3 | | |
| 3021 | PhO(CH2)2 | | |
| 3022 | PhCH2OCH2CH2 | | |
| 3023 | PhCH2O(C=O)CH2CH2 | | |

TABLE 3-continued

[Structure: oxazolidine-2,5-dione with isopropyl group at 4-position and R2-C(=O)- on N]

| Compound No. | R2 |
|---|---|
| 3024 | o-CH3Ph |
| 3025 | m-CH3Ph |
| 3026 | p-CH3Ph |
| 3027 | 2,4-(CH3)2Ph |
| 3028 | 3,5-(CH3)2Ph |
| 3029 | 2,4,6-(CH3)3Ph |
| 3030 | p-CH3OPh |
| 3031 | p-CH3CH2OPh |
| 3032 | p-CH3(CH2)2OPh |
| 3033 | p-FPh |
| 3034 | p-ClPh |
| 3035 | p-BrPh |
| 3036 | p-IPh |
| 3037 | p-PhOPh |
| 3038 | p-PhCH2OPh |
| 3039 | p-NO2Ph |
| 3040 | p-CNPh |
| 3041 | p-CH3SO2Ph |
| 3042 | 2-tetrahydrothienyl |
| 3043 | 2-tetrahydrofuryl |
| 3044 | 3-tetrahydropyranyl |

TABLE 4

| Compound No. | R2 | Compound No. | R2 |
|---|---|---|---|
| 4001 | CH3 | 4045 | 2-thienyl |
| 4002 | CH2CH3 | 4046 | 2-furyl |
| 4003 | (CH2)2CH3 | 4047 | 3-pyranyl |
| 4004 | CH(CH3)2 | 4048 | indenyl |
| 4005 | (CH2)3CH3 | 4049 | xanthenyl |
| 4006 | CH2CH(CH3)2 | 4050 | phenoxathiinyl |
| 4007 | CH(CH3)CH2CH3 | 4051 | 3-pyrrolyl |
| 4008 | C(CH3)3 | 4052 | 1-methylpyrazolyl |
| 4009 | (CH2)4CH3 | 4053 | isothiazolyl |
| 4010 | (CH2)5CH3 | 4054 | isoxazolyl |
| 4011 | (CH2)6CH3 | 4055 | 3-pyridyl |
| 4012 | (CH2)7CH3 | 4056 | 2-pyrazinyl |

TABLE 4-continued

[Structure: oxazolidine-2,5-dione with isopropyl group at position 4 and R2-C(=O)- on nitrogen]

| Compound No. | R2 | Compound No. | R2 |
|---|---|---|---|
| 4013 | (CH2)8CH3 | 4057 | indolizin-2-yl |
| 4014 | cyclopropyl | 4058 | naphthalen-2-yl |
| 4015 | cyclobutyl | 4059 | quinoxalin-2-yl |
| 4016 | cyclohexyl | 4060 | isoquinolin-3-yl |
| 4017 | Ph | 4061 | quinolin-2-yl |
| 4018 | PhCH2 | 4062 | 1-azabicyclo[2.2.1]heptyl |
| 4019 | Ph(CH2)2 | | |
| 4020 | Ph(CH2)3 | | |
| 4021 | PhO(CH2)2 | | |
| 4022 | PhCH2OCH2CH2 | | |
| 4023 | PhCH2O(C=O)CH2CH2 | | |
| 4024 | o-CH3Ph | | |
| 4025 | m-CH3Ph | | |
| 4026 | p-CH3Ph | | |
| 4027 | 2,4-(CH3)2Ph | | |
| 4028 | 3,5-(CH3)2Ph | | |
| 4029 | 2,4,6-(CH3)3Ph | | |
| 4030 | p-CH3OPh | | |
| 4031 | p-CH3CH2OPh | | |
| 4032 | p-CH3(CH2)2OPh | | |
| 4033 | p-FPh | | |
| 4034 | p-ClPh | | |

TABLE 4-continued

Structure: oxazolidine-2,5-dione with isopropyl group at 4-position and R2-C(=O)- on N

| Compound No. | R2 |
|---|---|
| 4035 | p-BrPh |
| 4036 | p-IPh |
| 4037 | p-PhOPh |
| 4038 | p-PhCH2OPh |
| 4039 | p-NO2Ph |
| 4040 | p-CNPh |
| 4041 | p-CH3SO2Ph |
| 4042 | 2-thiolanyl |
| 4043 | 2-tetrahydrofuranyl |
| 4044 | 2-tetrahydropyranyl |

TABLE 5

Structure: oxazolidine-2,5-dione with isobutyl group at 4-position and R2-C(=O)- on N

| Compound No. | R2 | Compound No. | R2 |
|---|---|---|---|
| 5001 | CH3 | 5045 | 2-thienyl |
| 5002 | CH2CH3 | 5046 | 2-furyl |
| 5003 | (CH2)2CH3 | 5047 | 3,4-dihydro-2H-pyran-3-yl |
| 5004 | CH(CH3)2 | 5048 | indenyl |

TABLE 5-continued
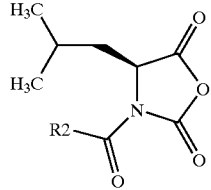
| Compound No. | R2 | Compound No. | R2 |
|---|---|---|---|
| 5005 | (CH2)3CH3 | 5049 | 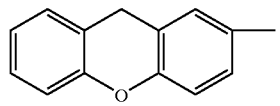 |
| 5006 | CH2CH(CH3)2 | 5050 | 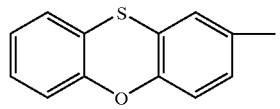 |
| 5007 | CH(CH3)CH2CH3 | 5051 |  |
| 5008 | C(CH3)3 | 5052 | 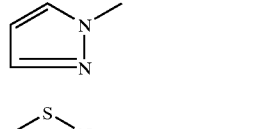 |
| 5009 | (CH2)4CH3 | 5053 | 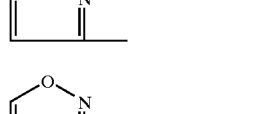 |
| 5010 | (CH2)5CH3 | 5054 |  |
| 5011 | (CH2)6CH3 | 5055 |  |
| 5012 | (CH2)7CH3 | 5056 | 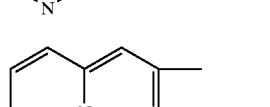 |
| 5013 | (CH2)8CH3 | 5057 | 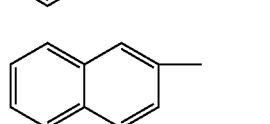 |
| 5014 | cyclopropyl | 5058 | 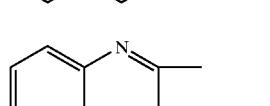 |
| 5015 | cyclobutyl | 5059 | 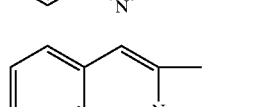 |
| 5016 | cyclohexyl | 5060 |  |

TABLE 5-continued

[Structure: oxazolidine-2,5-dione with isobutyl group at C-4 and R2-C(=O)- on N]

| Compound No. | R2 | Compound No. | R2 |
|---|---|---|---|
| 5017 | Ph | 5061 | [2-quinolinyl] |
| 5018 | PhCH2 | 5062 | [quinuclidinyl] |
| 5019 | Ph(CH2)2 | | |
| 5020 | Ph(CH2)3 | | |
| 5021 | PhO(CH2)2 | | |
| 5022 | PhCH2OCH2CH2 | | |
| 5023 | PhCH2O(C=O)CH2CH2 | | |
| 5024 | o-CH3Ph | | |
| 5025 | m-CH3Ph | | |
| 5026 | p-CH3Ph | | |
| 5027 | 2,4-(CH3)2Ph | | |
| 5028 | 3,5-(CH3)2Ph | | |
| 5029 | 2,4,6-(CH3)3Ph | | |
| 5030 | p-CH3OPh | | |
| 5031 | p-CH3CH2OPh | | |
| 5032 | p-CH3(CH2)2OPh | | |
| 5033 | p-FPh | | |
| 5034 | p-ClPh | | |
| 5035 | p-BrPh | | |
| 5036 | p-IPh | | |
| 5037 | p-PhOPh | | |
| 5038 | p-PhCH2OPh | | |
| 5039 | p-NO2Ph | | |
| 5040 | p-CNPh | | |
| 5041 | p-CH3SO2Ph | | |
| 5042 | [2-tetrahydrothienyl] | | |
| 5043 | [2-tetrahydrofuryl] | | |

TABLE 5-continued
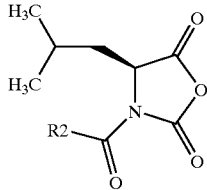
| Compound No. | R2 | Compound No. | R2 |
|---|---|---|---|
| 5044 | 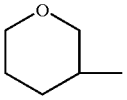 | | |
TABLE 6
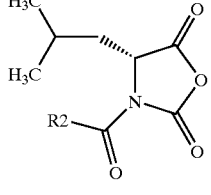
| Compound No. | R2 | Compound No. | R2 |
|---|---|---|---|
| 6001 | CH3 | 6045 | 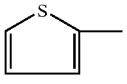 |
| 6002 | CH2CH3 | 6046 | 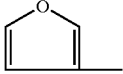 |
| 6003 | (CH2)2CH3 | 6047 | 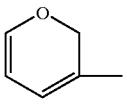 |
| 6004 | CH(CH3)2 | 6048 | 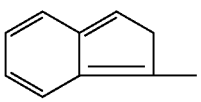 |
| 6005 | (CH2)3CH3 | 6049 | 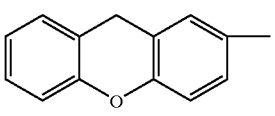 |
| 6006 | CH2CH(CH3)2 | 6050 | 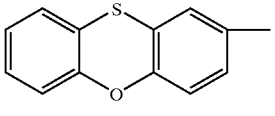 |
| 6007 | CH(CH3)CH2CH3 | 6051 |  |
| 6008 | C(CH3)3 | 6052 | 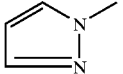 |

TABLE 6-continued
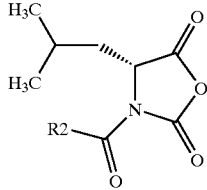
| Compound No. | R2 | Compound No. | R2 |
|---|---|---|---|
| 6009 | (CH2)4CH3 | 6053 | 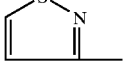 |
| 6010 | (CH2)5CH3 | 6054 | 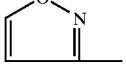 |
| 6011 | (CH2)6CH3 | 6055 | 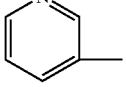 |
| 6012 | (CH2)7CH3 | 6056 | 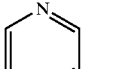 |
| 6013 | (CH2)8CH3 | 6057 | 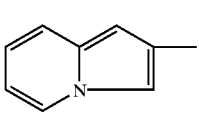 |
| 6014 | cyclopropyl | 6058 | 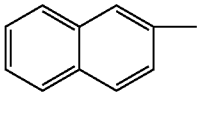 |
| 6015 | cyclobutyl | 6059 | 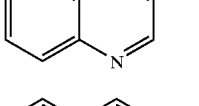 |
| 6016 | cyclohexyl | 6060 | 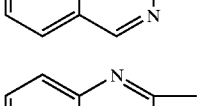 |
| 6017 | Ph | 6061 |  |
| 6018 | PhCH2 | 6062 | 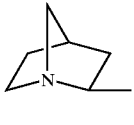 |
| 6019 | Ph(CH2)2 | | |
| 6020 | Ph(CH2)3 | | |
| 6021 | PhO(CH2)2 | | |
| 6022 | PhCH2OCH2CH2 | | |
| 6023 | PhCH2O(C=O)CH2CH2 | | |

TABLE 6-continued
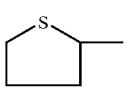
| Compound No. | R2 | Compound No. | R2 |
|---|---|---|---|
| 6024 | o-CH3Ph | | |
| 6025 | m-CH3Ph | | |
| 6026 | p-CH3Ph | | |
| 6027 | 2,4-(CH3)2Ph | | |
| 6028 | 3,5-(CH3)2Ph | | |
| 6029 | 2,4,6-(CH3)3Ph | | |
| 6030 | p-CH3OPh | | |
| 6031 | p-CH3CH2OPh | | |
| 6032 | p-CH3(CH2)2OPh | | |
| 6033 | p-FPh | | |
| 6034 | p-ClPh | | |
| 6035 | p-BrPh | | |
| 6036 | p-IPh | | |
| 6037 | p-PhOPh | | |
| 6038 | p-PhCH2OPh | | |
| 6039 | p-NO2Ph | | |
| 6040 | p-CNPh | | |
| 6041 | p-CH3SO2Ph | | |
| 6042 | 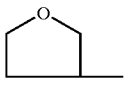 | | |
| 6043 | 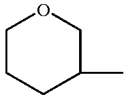 | | |
| 6044 | | | |

TABLE 7
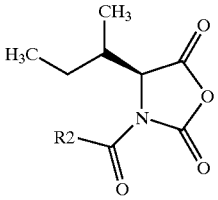
| Compound No. | R2 | Compound No. | R2 |
|---|---|---|---|
| 7001 | CH3 | 7045 | 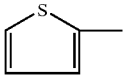 |
| 7002 | CH2CH3 | 7046 | 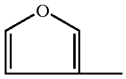 |
| 7003 | (CH2)2CH3 | 7047 | 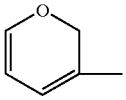 |
| 7004 | CH(CH3)2 | 7048 | 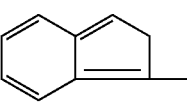 |
| 7005 | (CH2)3CH3 | 7049 | 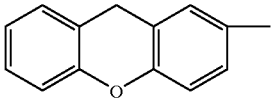 |
| 7006 | CH2CH(CH3)2 | 7050 | 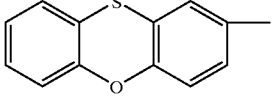 |
| 7007 | CH(CH3)CH2CH3 | 7051 |  |
| 7008 | C(CH3)3 | 7052 | 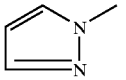 |
| 7009 | (CH2)4CH3 | 7053 | 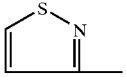 |
| 7010 | (CH2)5CH3 | 7054 | 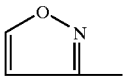 |
| 7011 | (CH2)6CH3 | 7055 | 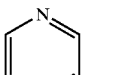 |
| 7012 | (CH2)7CH3 | 7056 | 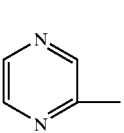 |

TABLE 7-continued

| Compound No. | R2 | Compound No. | R2 |
|---|---|---|---|
| 7013 | (CH2)8CH3 | 7057 | (2-indolizinyl) |
| 7014 | cyclopropyl | 7058 | (2-naphthyl) |
| 7015 | cyclobutyl | 7059 | (2-quinoxalinyl) |
| 7016 | cyclohexyl | 7060 | (3-isoquinolinyl) |
| 7017 | Ph | 7061 | (2-quinolinyl) |
| 7018 | PhCH2 | 7062 | (quinuclidinyl) |
| 7019 | Ph(CH2)2 | | |
| 7020 | Ph(CH2)3 | | |
| 7021 | PhO(CH2)2 | | |
| 7022 | PhCH2OCH2CH2 | | |
| 7023 | PhCH2O(C=O)CH2CH2 | | |
| 7024 | o-CH3Ph | | |
| 7025 | m-CH3Ph | | |
| 7026 | p-CH3Ph | | |
| 7027 | 2,4-(CH3)2Ph | | |
| 7028 | 3,5-(CH3)2Ph | | |
| 7029 | 2,4,6-(CH3)3Ph | | |
| 7030 | p-CH3OPh | | |
| 7031 | p-CH3CH2OPh | | |
| 7032 | p-CH3(CH2)2OPh | | |
| 7033 | p-FPh | | |
| 7034 | p-ClPh | | |

TABLE 7-continued

| Compound No. | R2 | Compound No. | R2 |
|---|---|---|---|
| 7035 | p-BrPh | | |
| 7036 | p-IPh | | |
| 7037 | p-PhOPh | | |
| 7038 | p-PhCH2OPh | | |
| 7039 | p-NO2Ph | | |
| 7040 | p-CNPh | | |
| 7041 | p-CH3SO2Ph | | |
| 7042 | (2-tetrahydrothienyl) | | |
| 7043 | (2-tetrahydrofuryl) | | |
| 7044 | (3-tetrahydropyranyl) | | |

TABLE 8

| Compound No. | R2 | Compound No. | R2 |
|---|---|---|---|
| 8001 | CH3 | 8045 | (2-thienyl) |
| 8002 | CH2CH3 | 8046 | (2-furyl) |
| 8003 | (CH2)2CH3 | 8047 | (3,4-dihydro-2H-pyran-3-yl) |
| 8004 | CH(CH3)2 | 8048 | (indenyl) |

TABLE 8-continued

| Compound No. | R2 | Compound No. | R2 |
|---|---|---|---|
| 8005 | (CH2)3CH3 | 8049 | xanthene-2-yl |
| 8006 | CH2CH(CH3)2 | 8050 | phenoxathiine-2-yl |
| 8007 | CH(CH3)CH2CH3 | 8051 | pyrrolyl-methyl |
| 8008 | C(CH3)3 | 8052 | 1-methylpyrazol-5-yl |
| 8009 | (CH2)4CH3 | 8053 | isothiazolyl |
| 8010 | (CH2)5CH3 | 8054 | isoxazolyl |
| 8011 | (CH2)6CH3 | 8055 | pyridin-3-yl |
| 8012 | (CH2)7CH3 | 8056 | pyrazin-2-yl |
| 8013 | (CH2)8CH3 | 8057 | indolizin-2-yl |
| 8014 | cyclopropyl | 8058 | naphth-2-yl |
| 8015 | cyclobutyl | 8059 | quinoxalin-2-yl |
| 8016 | cyclohexyl | 8060 | isoquinolin-3-yl |

TABLE 8-continued
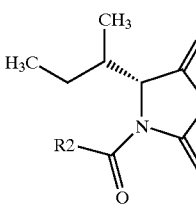
| Compound No. | R2 | Compound No. | R2 |
|---|---|---|---|
| 8017 | Ph | 8061 | 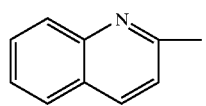 |
| 8018 | PhCH2 | 8062 |  |
| 8019 | Ph(CH2)2 | | |
| 8020 | Ph(CH2)3 | | |
| 8021 | PhO(CH2)2 | | |
| 8022 | PhCH2OCH2CH2 | | |
| 8023 | PhCH2O(C=O)CH2CH2 | | |
| 8024 | o-CH3Ph | | |
| 8025 | m-CH3Ph | | |
| 8026 | p-CH3Ph | | |
| 8027 | 2,4-(CH3)2Ph | | |
| 8028 | 3,5-(CH3)2Ph | | |
| 8029 | 2,4,6-(CH3)3Ph | | |
| 8030 | p-CH3OPh | | |
| 8031 | p-CH3CH2OPh | | |
| 8032 | p-CH3(CH2)2OPh | | |
| 8033 | p-FPh | | |
| 8034 | p-ClPh | | |
| 8035 | p-BrPh | | |
| 8036 | p-IPh | | |
| 8037 | p-PhOPh | | |
| 8038 | p-PhCH2OPh | | |
| 8039 | p-NO2Ph | | |
| 8040 | p-CNPh | | |
| 8041 | p-CH3SO2Ph | | |
| 8042 | 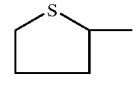 | | |
| 8043 | 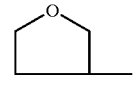 | | |

TABLE 8-continued
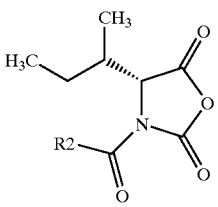
| Compound No. | R2 | Compound No. | R2 |
|---|---|---|---|
| 8044 | 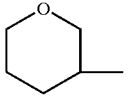 | | |
TABLE 9
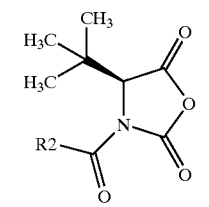
| Compound No. | R2 | Compound No. | R2 |
|---|---|---|---|
| 9001 | CH3 | 9045 | 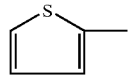 |
| 9002 | CH2CH3 | 9046 | 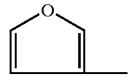 |
| 9003 | (CH2)2CH3 | 9047 | 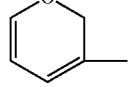 |
| 9004 | CH(CH3)2 | 9048 | 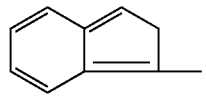 |
| 9005 | (CH2)3CH3 | 9049 | 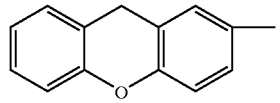 |
| 9006 | CH2CH(CH3)2 | 9050 | 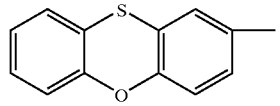 |
| 9007 | CH(CH3)CH2CH3 | 9051 | 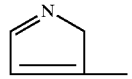 |
| 9008 | C(CH3)3 | 9052 | 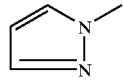 |

TABLE 9-continued
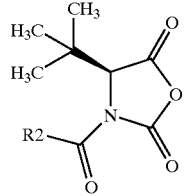
| Compound No. | R2 | Compound No. | R2 |
|---|---|---|---|
| 9009 | (CH2)4CH3 | 9053 | 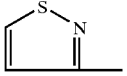 |
| 9010 | (CH2)5CH3 | 9054 | 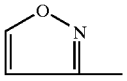 |
| 9011 | (CH2)6CH3 | 9055 | 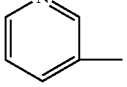 |
| 9012 | (CH2)7CH3 | 9056 | 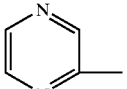 |
| 9013 | (CH2)8CH3 | 9057 | 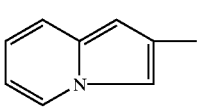 |
| 9014 | cyclopropyl | 9058 | 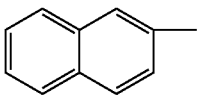 |
| 9015 | cyclobutyl | 9059 | 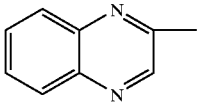 |
| 9016 | cyclohexyl | 9060 | 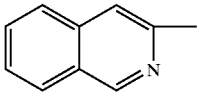 |
| 9017 | Ph | 9061 | 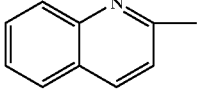 |
| 9018 | PhCH2 | 9062 | 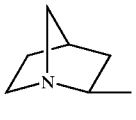 |
| 9019 | Ph(CH2)2 | | |
| 9020 | Ph(CH2)3 | | |
| 9021 | PhO(CH2)2 | | |
| 9022 | PhCH2OCH2CH2 | | |
| 9023 | PhCH2O(C=O)CH2CH2 | | |

TABLE 9-continued

| Compound No. | R2 | Compound No. | R2 |
|---|---|---|---|
| 9024 | o-CH3Ph | | |
| 9025 | m-CH3Ph | | |
| 9026 | p-CH3Ph | | |
| 9027 | 2,4-(CH3)2Ph | | |
| 9028 | 3,5-(CH3)2Ph | | |
| 9029 | 2,4,6-(CH3)3Ph | | |
| 9030 | p-CH3OPh | | |
| 9031 | p-CH3CH2OPh | | |
| 9032 | p-CH3(CH2)2OPh | | |
| 9033 | p-FPh | | |
| 9034 | p-ClPh | | |
| 9035 | p-BrPh | | |
| 9036 | p-IPh | | |
| 9037 | p-PhOPh | | |
| 9038 | p-PhCH2OPh | | |
| 9039 | p-NO2Ph | | |
| 9040 | p-CNPh | | |
| 9041 | p-CH3SO2Ph | | |
| 9042 | (2-tetrahydrothiophenyl) | | |
| 9043 | (tetrahydrofuran-2-yl) | | |
| 9044 | (tetrahydropyran-2-yl) | | |

TABLE 10
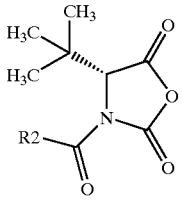
| Compound No. | R2 | Compound No. | R2 |
|---|---|---|---|
| 10001 | CH3 | 10045 | 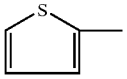 |
| 10002 | CH2CH3 | 10046 | 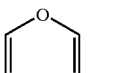 |
| 10003 | (CH2)2CH3 | 10047 | 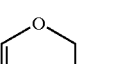 |
| 10004 | CH(CH3)2 | 10048 | 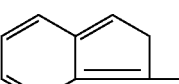 |
| 10005 | (CH2)3CH3 | 10049 | 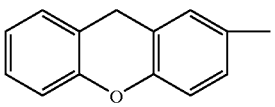 |
| 10006 | CH2CH(CH3)2 | 10050 | 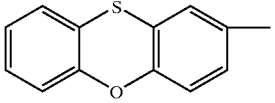 |
| 10007 | CH(CH3)CH2CH3 | 10051 | 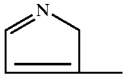 |
| 10008 | C(CH3)3 | 10052 | 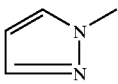 |
| 10009 | (CH2)4CH3 | 10053 | 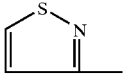 |
| 10010 | (CH2)5CH3 | 10054 | 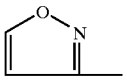 |
| 10011 | (CH2)6CH3 | 10055 | 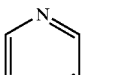 |
| 10012 | (CH2)7CH3 | 10056 | 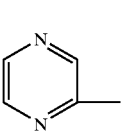 |

TABLE 10-continued
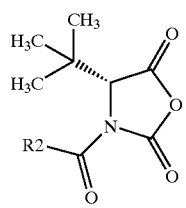
| Compound No. | R2 | Compound No. | R2 |
|---|---|---|---|
| 10013 | (CH2)8CH3 | 10057 | 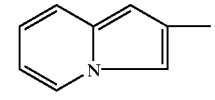 |
| 10014 | cyclopropyl | 10058 | 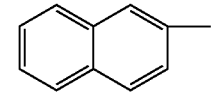 |
| 10015 | cyclobutyl | 10059 | 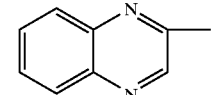 |
| 10016 | cyclohexyl | 10060 | 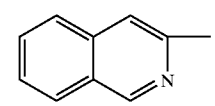 |
| 10017 | Ph | 10061 | 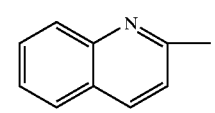 |
| 10018 | PhCH2 | 10062 |  |
| 10019 | Ph(CH2)2 | | |
| 10020 | Ph(CH2)3 | | |
| 10021 | PhO(CH2)2 | | |
| 10022 | PhCH2OCH2CH2 | | |
| 10023 | PhCH2O(C=O)CH2CH2 | | |
| 10024 | o-CH3Ph | | |
| 10025 | m-CH3Ph | | |
| 10026 | p-CH3Ph | | |
| 10027 | 2,4-(CH3)2Ph | | |
| 10028 | 3,5-(CH3)2Ph | | |
| 10029 | 2,4,6-(CH3)3Ph | | |
| 10030 | p-CH3OPh | | |
| 10031 | p-CH3CH2OPh | | |
| 10032 | p-CH3(CH2)2OPh | | |
| 10033 | p-FPh | | |
| 10034 | p-ClPh | | |

TABLE 10-continued

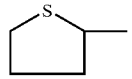

| Compound No. | R2 | Compound No. | R2 |
|---|---|---|---|
| 10035 | p-BrPh | | |
| 10036 | p-IPh | | |
| 10037 | p-PhOPh | | |
| 10038 | p-PhCH2OPh | | |
| 10039 | p-NO2Ph | | |
| 10040 | p-CNPh | | |
| 10041 | p-CH3SO2Ph | | |
| 10042 | 2-tetrahydrothienyl | | |
| 10043 | 2-tetrahydrofuryl | | |
| 10044 | 2-tetrahydropyranyl | | |

TABLE 11

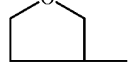

| Compound No. | R2 | Compound No. | R2 |
|---|---|---|---|
| 11001 | CH3 | 11021 | PhO(CH2)2 |
| 11002 | CH2CH3 | 11022 | PhCH2OCH2CH2 |
| 11003 | (CH2)2CH3 | 11023 | PhCH2O(C=O)CH2CH2 |
| 11004 | CH(CH3)2 | 11024 | o-CH3Ph |
| 11005 | (CH2)3CH3 | 11025 | m-CH3Ph |
| 11006 | CH2CH(CH3)2 | 11026 | p-CH3Ph |
| 11007 | CH(CH3)CH2CH3 | 11027 | 2,4-(CH3)2Ph |
| 11008 | C(CH3)3 | 11028 | 3,5-(CH3)2Ph |
| 11009 | (CH2)4CH3 | 11029 | 2,4,6-(CH3)3Ph |
| 11010 | (CH2)5CH3 | 11030 | p-CH3OPh |
| 11011 | (CH2)6CH3 | 11031 | p-CH3CH2OPh |
| 11012 | (CH2)7CH3 | 11032 | p-CH3(CH2)2OPh |
| 11013 | (CH2)8CH3 | 11033 | p-FPh |
| 11014 | cyclopropyl | 11034 | p-ClPh |
| 11015 | cyclobutyl | 11035 | p-BrPh |
| 11016 | cyclohexyl | 11036 | p-IPh |
| 11017 | Ph | 11037 | p-PhOPh |
| 11018 | PhCH2 | 11038 | p-PhCH2OPh |
| 11019 | Ph(CH2)2 | 11039 | p-NO2Ph |
| 11020 | Ph(CH2)3 | 11040 | p-CNPh |

TABLE 11-continued

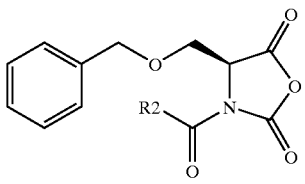

| Compound No. | R2 |
|---|---|
| 11041 | p-CH3SO2Ph |
| 11042 | tetrahydrothiophen-2-yl |
| 11043 | tetrahydrofuran-2-yl |
| 11044 | tetrahydropyran-3-yl |
| 11045 | thiophen-2-yl |
| 11046 | furan-2-yl |
| 11047 | 3,4-dihydro-2H-pyran-3-yl |
| 11048 | 2,3-dihydro-1H-inden-1-yl |
| 11049 | 9H-xanthen-2-yl |
| 11050 | phenoxathiin-2-yl |
| 11051 | 2H-pyrrol-3-yl |
| 11052 | 1-methyl-1H-pyrazol-3-yl |

TABLE 11-continued

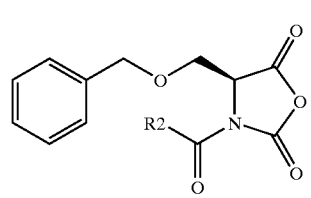

| Compound No. | R2 |
|---|---|
| 11053 | isothiazol-3-yl |
| 11054 | isoxazol-3-yl |
| 11055 | pyridin-3-yl |
| 11056 | pyrazin-2-yl |
| 11057 | indolizin-2-yl |
| 11058 | naphthalen-2-yl |
| 11059 | quinoxalin-2-yl |
| 11060 | isoquinolin-3-yl |
| 11061 | quinolin-2-yl |
| 11062 | quinuclidin-2-yl |

TABLE 12
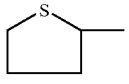
| Compound No. | R2 |
|---|---|
| 12001 | CH3 |
| 12002 | CH2CH3 |
| 12003 | (CH2)2CH3 |
| 12004 | CH(CH3)2 |
| 12005 | (CH2)3CH3 |
| 12006 | CH2CH(CH3)2 |
| 12007 | CH(CH3)CH2CH3 |
| 12008 | C(CH3)3 |
| 12009 | (CH2)4CH3 |
| 12010 | (CH2)5CH3 |
| 12011 | (CH2)6CH3 |
| 12012 | (CH2)7CH3 |
| 12013 | (CH2)8CH3 |
| 12014 | cyclopropyl |
| 12015 | cyclobutyl |
| 12016 | cyclohexyl |
| 12017 | Ph |
| 12018 | PhCH2 |
| 12019 | Ph(CH2)2 |
| 12020 | Ph(CH2)3 |
| 12021 | PhO(CH2)2 |
| 12022 | PhCH2OCH2CH2 |
| 12023 | PhCH2O(C=O)CH2CH2 |
| 12024 | o-CH3Ph |
| 12025 | m-CH3Ph |
| 12026 | p-CH3Ph |
| 12027 | 2,4-(CH3)2Ph |
| 12028 | 3,5-(CH3)2Ph |
| 12029 | 2,4,6-(CH3)3Ph |
| 12030 | p-CH3OPh |
| 12031 | p-CH3CH2OPh |
| 12032 | p-CH3(CH2)2OPh |
| 12033 | p-FPh |
| 12034 | p-ClPh |
| 12035 | p-BrPh |
| 12036 | p-IPh |
| 12037 | p-PhOPh |
| 12038 | p-PhCH2OPh |
| 12039 | p-NO2Ph |
| 12040 | p-CNPh |
| 12041 | p-CH3SO2Ph |
| 12042 | 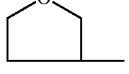 |
| 12043 | 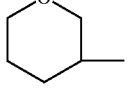 |
| 12044 | 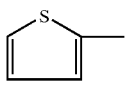 |
| 12045 | 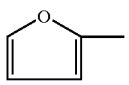 |
| 12046 | 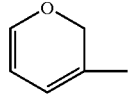 |
TABLE 12-continued
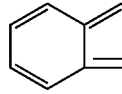
| Compound No. | R2 |
|---|---|
| 12047 | 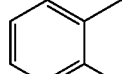 |
| 12048 | 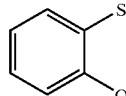 |
| 12049 | 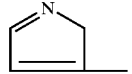 |
| 12050 | 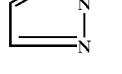 |
| 12051 | 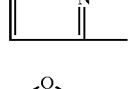 |
| 12052 | 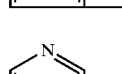 |
| 12053 | 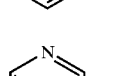 |
| 12054 | 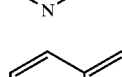 |
| 12055 | 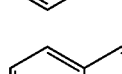 |
| 12056 | 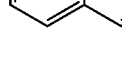 |
| 12057 |  |
| 12058 |  |

TABLE 12-continued
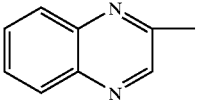
| Compound No. | R2 |
|---|---|
| 12059 | 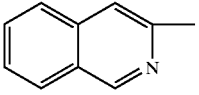 |
| 12060 | 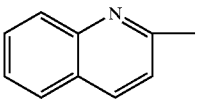 |
| 12061 |  |
| 12062 | 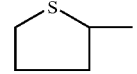 |
TABLE 13
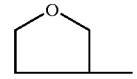
| Compound No. | R2 |
|---|---|
| 13001 | CH3 |
| 13002 | CH2CH3 |
| 13003 | (CH2)2CH3 |
| 13004 | CH(CH3)2 |
| 13005 | (CH2)3CH3 |
| 13006 | CH2CH(CH3)2 |
| 13007 | CH(CH3)CH2CH3 |
| 13008 | C(CH3)3 |
| 13009 | (CH2)4CH3 |
| 13010 | (CH2)5CH3 |
| 13011 | (CH2)6CH3 |
| 13012 | (CH2)7CH3 |
| 13013 | (CH2)8CH3 |
| 13014 | cyclopropyl |
| 13015 | cyclobutyl |
| 13016 | cyclohexyl |
| 13017 | Ph |
| 13018 | PhCH2 |
| 13019 | Ph(CH2)2 |
| 13020 | Ph(CH2)3 |
| 13021 | PhO(CH2)2 |
| 13022 | PhCH2OCH2CH2 |
| 13023 | PhCH2O(C=O)CH2CH2 |
| 13024 | o-CH3Ph |
| 13025 | m-CH3Ph |
| 13026 | p-CH3Ph |
| 13027 | 2,4-(CH3)2Ph |
| 13028 | 3,5-(CH3)2Ph |
TABLE 13-continued
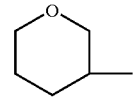
| Compound No. | R2 |
|---|---|
| 13029 | 2,4,6-(CH3)3Ph |
| 13030 | p-CH3OPh |
| 13031 | p-CH3CH2OPh |
| 13032 | p-CH3(CH2)2OPh |
| 13033 | p-FPh |
| 13034 | p-ClPh |
| 13035 | p-BrPh |
| 13036 | p-IPh |
| 13037 | p-PhOPh |
| 13038 | p-PhCH2OPh |
| 13039 | p-NO2Ph |
| 13040 | p-CNPh |
| 13041 | p-CH3SO2Ph |
| 13042 | 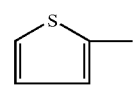 |
| 13043 | 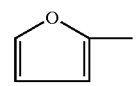 |
| 13044 | 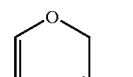 |
| 13045 | 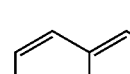 |
| 13046 | 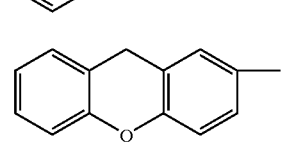 |
| 13047 | 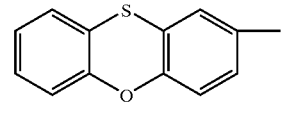 |
| 13048 |  |
| 13049 |  |
| 13050 |  |
| 13051 |  |

TABLE 13-continued
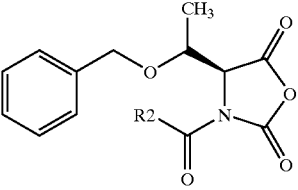
| Compound No. | R2 |
|---|---|
| 13052 | 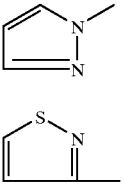 |
| 13053 | 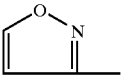 |
| 13054 | 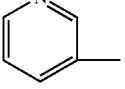 |
| 13055 | 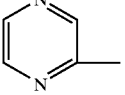 |
| 13056 | 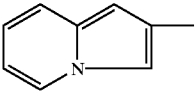 |
| 13057 | 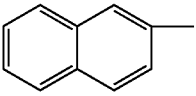 |
| 13058 | 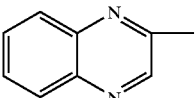 |
| 13059 | 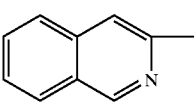 |
| 13060 | 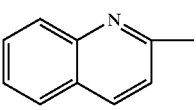 |
| 13061 |  |
| 13062 | 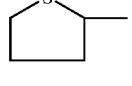 |
TABLE 14
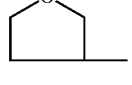
| Compound No. | R2 |
|---|---|
| 14001 | CH3 |
| 14002 | CH2CH3 |
| 14003 | (CH2)2CH3 |
| 14004 | CH(CH3)2 |
| 14005 | (CH2)3CH3 |
| 14006 | CH2CH(CH3)2 |
| 14007 | CH(CH3)CH2CH3 |
| 14008 | C(CH3)3 |
| 14009 | (CH2)4CH3 |
| 14010 | (CH2)5CH3 |
| 14011 | (CH2)6CH3 |
| 14012 | (CH2)7CH3 |
| 14013 | (CH2)8CH3 |
| 14014 | cyclopropyl |
| 14015 | cyclobutyl |
| 14016 | cyclohexyl |
| 14017 | Ph |
| 14018 | PhCH2 |
| 14019 | Ph(CH2)2 |
| 14020 | Ph(CH2)3 |
| 14021 | PhO(CH2)2 |
| 14022 | PhCH2OCH2CH2 |
| 14023 | PhCH2O(C=O)CH2CH2 |
| 14024 | o-CH3Ph |
| 14025 | m-CH3Ph |
| 14026 | p-CH3Ph |
| 14027 | 2,4-(CH3)2Ph |
| 14028 | 3,5-(CH3)2Ph |
| 14029 | 2,4,6-(CH3)3Ph |
| 14030 | p-CH3OPh |
| 14031 | p-CH3CH2OPh |
| 14032 | p-CH3(CH2)2OPh |
| 14033 | p-FPh |
| 14034 | p-ClPh |
| 14035 | p-BrPh |
| 14036 | p-IPh |
| 14037 | p-PhOPh |
| 14038 | p-PhCH2OPh |
| 14039 | p-NO2Ph |
| 14040 | p-CNPh |
| 14041 | p-CH3SO2Ph |
| 14042 | 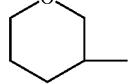 |
| 14043 | 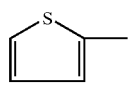 |
| 14044 | 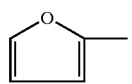 |
| 14045 |  |
| 14046 |  |

TABLE 14-continued

[Structure: benzyl ether with CH3 substituent on oxazolidine-2,5-dione with R2-C(=O)-N]

| Compound No. | R2 |
|---|---|
| 14047 | (2H-pyran-3-yl) |
| 14048 | (indene) |
| 14049 | (xanthene-2-yl) |
| 14050 | (phenoxathiin-2-yl) |
| 14051 | (pyrrole) |
| 14052 | (N-methylpyrazol-3-yl) |
| 14053 | (isothiazol-3-yl) |
| 14054 | (isoxazol-3-yl) |
| 14055 | (pyridin-3-yl) |
| 14056 | (pyrazin-2-yl) |
| 14057 | (indolizin-2-yl) |
| 14058 | (naphthalen-2-yl) |

TABLE 14-continued

[Structure: benzyl ether with CH3 substituent on oxazolidine-2,5-dione with R2-C(=O)-N]

| Compound No. | R2 |
|---|---|
| 14059 | (quinoxalin-2-yl) |
| 14060 | (isoquinolin-3-yl) |
| 14061 | (quinolin-2-yl) |
| 14062 | (quinuclidin-2-yl) |

TABLE 15

[Structure: benzyl ester with CH2 linker on oxazolidine-2,5-dione with R2-C(=O)-N]

| Compound No. | R2 |
|---|---|
| 15001 | CH3 |
| 15002 | CH2CH3 |
| 15003 | (CH2)2CH3 |
| 15004 | CH(CH3)2 |
| 15005 | (CH2)3CH3 |
| 15006 | CH2CH(CH3)2 |
| 15007 | CH(CH3)CH2CH3 |
| 15008 | C(CH3)3 |
| 15009 | (CH2)4CH3 |
| 15010 | (CH2)5CH3 |
| 15011 | (CH2)6CH3 |
| 15012 | (CH2)7CH3 |
| 15013 | (CH2)8CH3 |
| 15014 | cyclopropyl |
| 15015 | cyclobutyl |
| 15016 | cyclohexyl |
| 15017 | Ph |
| 15018 | PhCH2 |
| 15019 | Ph(CH2)2 |
| 15020 | Ph(CH2)3 |
| 15021 | PhO(CH2)2 |
| 15022 | PhCH2OCH2CH2 |
| 15023 | PhCH2O(C=O)CH2CH2 |
| 15024 | o-CH3Ph |
| 15025 | m-CH3Ph |
| 15026 | p-CH3Ph |
| 15027 | 2,4-(CH3)2Ph |

TABLE 15-continued

| Compound No. | R2 |
|---|---|
| 15028 | 3,5-(CH3)2Ph |
| 15029 | 2,4,6-(CH3)3Ph |
| 15030 | p-CH3OPh |
| 15031 | p-CH3CH2OPh |
| 15032 | p-CH3(CH2)2OPh |
| 15033 | p-FPh |
| 15034 | p-ClPh |
| 15035 | p-BrPh |
| 15036 | p-IPh |
| 15037 | p-PhOPh |
| 15038 | p-PhCH2OPh |
| 15039 | p-NO2Ph |
| 15040 | p-CNPh |
| 15041 | p-CH3SO2Ph |
| 15042 | tetrahydrothiophen-2-yl |
| 15043 | tetrahydrofuran-2-yl |
| 15044 | tetrahydropyran-3-yl |
| 15045 | thiophen-2-yl |
| 15046 | furan-2-yl |
| 15047 | 3,4-dihydro-2H-pyran-3-yl |
| 15048 | indene-yl |
| 15049 | xanthene-2-yl |
| 15050 | phenoxathiine-yl |
| 15051 | pyrrol-3-yl |
| 15052 | 1-methylpyrazol-3-yl |
| 15053 | isothiazol-3-yl |
| 15054 | isoxazol-3-yl |
| 15055 | pyridin-3-yl |
| 15056 | pyrazin-2-yl |
| 15057 | indolizin-2-yl |
| 15058 | naphthalen-2-yl |
| 15059 | quinoxalin-2-yl |
| 15060 | isoquinolin-3-yl |
| 15061 | quinolin-2-yl |
| 15062 | 1-azabicyclo[2.2.1]heptan-yl |

TABLE 16
| Compound No. | R2 |
|---|---|
| 16001 | CH3 |
| 16002 | CH2CH3 |
| 16003 | (CH2)2CH3 |
| 16004 | CH(CH3)2 |
| 16005 | (CH2)3CH3 |
| 16006 | CH2CH(CH3)2 |
| 16007 | CH(CH3)CH2CH3 |
| 16008 | C(CH3)3 |
| 16009 | (CH2)4CH3 |
| 16010 | (CH2)5CH3 |
| 16011 | (CH2)6CH3 |
| 16012 | (CH2)7CH3 |
| 16013 | (CH2)8CH3 |
| 16014 | cyclopropyl |
| 16015 | cyclobutyl |
| 16016 | cyclohexyl |
| 16017 | Ph |
| 16018 | PhCH2 |
| 16019 | Ph(CH2)2 |
| 16020 | Ph(CH2)3 |
| 16021 | PhO(CH2)2 |
| 16022 | PhCH2OCH2CH2 |
| 16023 | PhCH2O(C=O)CH2CH2 |
| 16024 | o-CH3Ph |
| 16025 | m-CH3Ph |
| 16026 | p-CH3Ph |
| 16027 | 2,4-(CH3)2Ph |
| 16028 | 3,5-(CH3)2Ph |
| 16029 | 2,4,6-(CH3)3Ph |
| 16030 | p-CH3OPh |
| 16031 | p-CH3CH2OPh |
| 16032 | p-CH3(CH2)2OPh |
| 16033 | p-FPh |
| 16034 | p-ClPh |
| 16035 | p-BrPh |
| 16036 | p-IPh |
| 16037 | p-PhOPh |
| 16038 | p-PhCH2OPh |
| 16039 | p-NO2Ph |
| 16040 | p-CNPh |
| 16041 | p-CH3SO2Ph |
| 16042 | 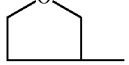 |
| 16043 | 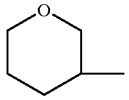 |
| 16044 | 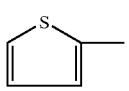 |
| 16045 | 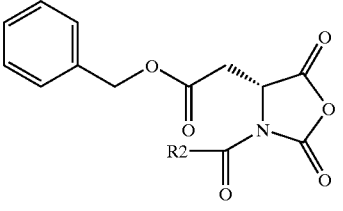 |
TABLE 16-continued
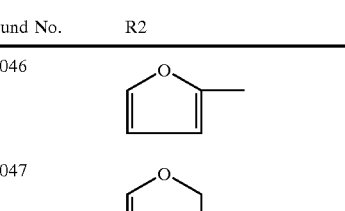
| Compound No. | R2 |
|---|---|
| 16046 | 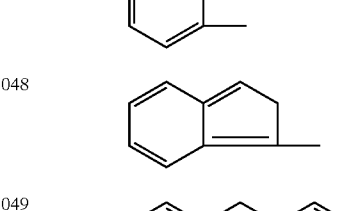 |
| 16047 | 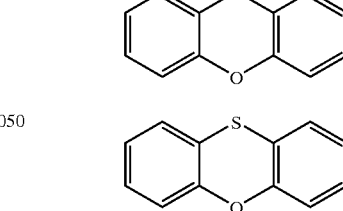 |
| 16048 | 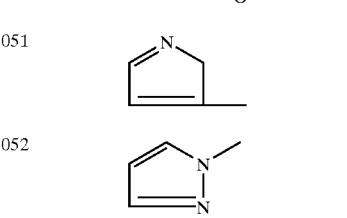 |
| 16049 | 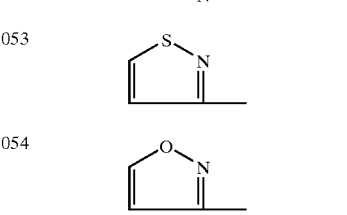 |
| 16050 | 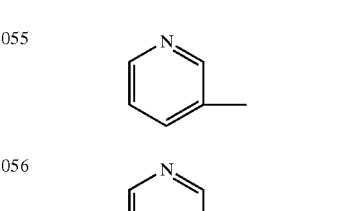 |
| 16051 | 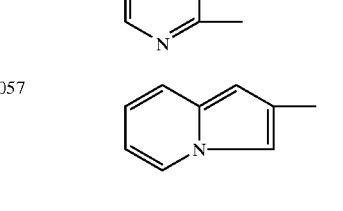 |
| 16052 | 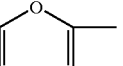 |
| 16053 | 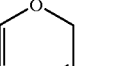 |
| 16054 | 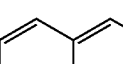 |
| 16055 | 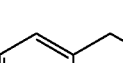 |
| 16056 | 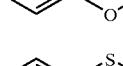 |
| 16057 | 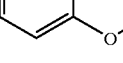 |

TABLE 16-continued
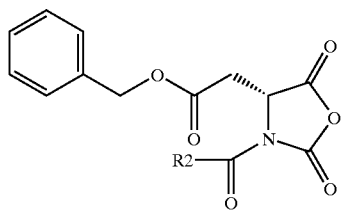
| Compound No. | R2 |
|---|---|
| 16058 | 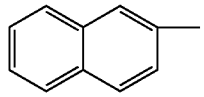 |
| 16059 | 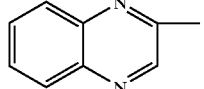 |
| 16060 | 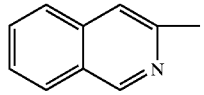 |
| 16061 | 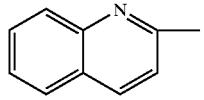 |
| 16062 | 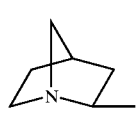 |
TABLE 17
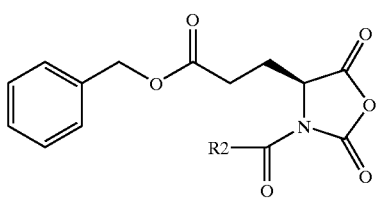
| Compound No. | R2 |
|---|---|
| 17001 | CH3 |
| 17002 | CH2CH3 |
| 17003 | (CH2)2CH3 |
| 17004 | CH(CH3)2 |
| 17005 | (CH2)3CH3 |
| 17006 | CH2CH(CH3)2 |
| 17007 | CH(CH3)CH2CH3 |
| 17008 | C(CH3)3 |
| 17009 | (CH2)4CH3 |
| 17010 | (CH2)5CH3 |
| 17011 | (CH2)6CH3 |
| 17012 | (CH2)7CH3 |
| 17013 | (CH2)8CH3 |
| 17014 | cyclopropyl |
| 17015 | cyclobutyl |
| 17016 | cyclohexyl |
| 17017 | Ph |
| 17018 | PhCH2 |
| 17019 | Ph(CH2)2 |
| 17020 | Ph(CH2)3 |
| 17021 | PhO(CH2)2 |
TABLE 17-continued
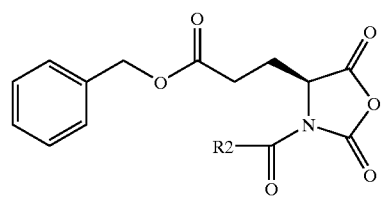
| Compound No. | R2 |
|---|---|
| 17022 | PhCH2OCH2CH2 |
| 17023 | PhCH2O(C=O)CH2CH2 |
| 17024 | o-CH3Ph |
| 17025 | m-CH3Ph |
| 17026 | p-CH3Ph |
| 17027 | 2,4-(CH3)2Ph |
| 17028 | 3,5-(CH3)2Ph |
| 17029 | 2,4,6-(CH3)3Ph |
| 17030 | p-CH3OPh |
| 17031 | p-CH3CH2OPh |
| 17032 | p-CH3(CH2)2OPh |
| 17033 | p-FPh |
| 17034 | p-ClPh |
| 17035 | p-BrPh |
| 17036 | p-IPh |
| 17037 | p-PhOPh |
| 17038 | p-PhCH2OPh |
| 17039 | p-NO2Ph |
| 17040 | p-CNPh |
| 17041 | p-CH3SO2Ph |
| 17042 | 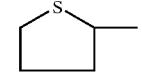 |
| 17043 | 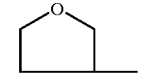 |
| 17044 | 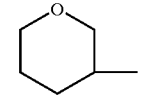 |
| 17045 | 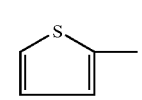 |
| 17046 | 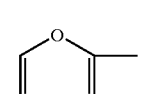 |
| 17047 | 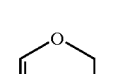 |
| 17048 | 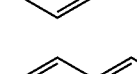 |
| 17049 | 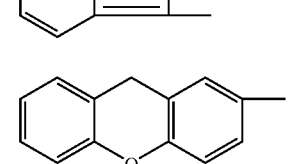 |

TABLE 17-continued
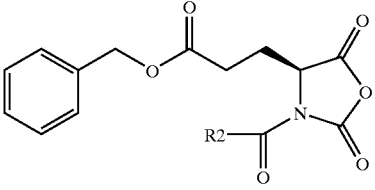
| Compound No. | R2 |
|---|---|
| 17050 | 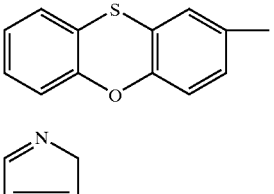 |
| 17051 | 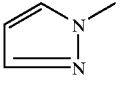 |
| 17052 |  |
| 17053 | 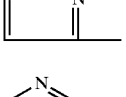 |
| 17054 | 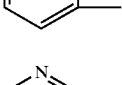 |
| 17055 | 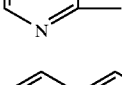 |
| 17056 | 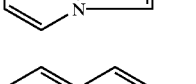 |
| 17057 | 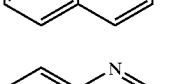 |
| 17058 | 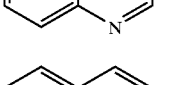 |
| 17059 | 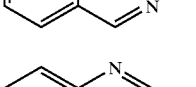 |
| 17060 | 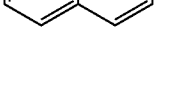 |
| 17061 | 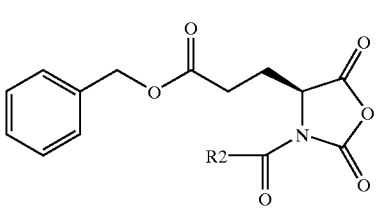 |
TABLE 17-continued
| Compound No. | R2 |
|---|---|
| 17062 | 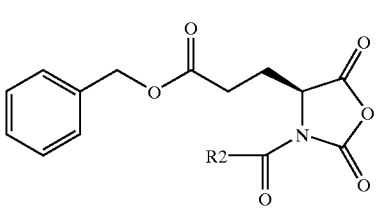 |
TABLE 18
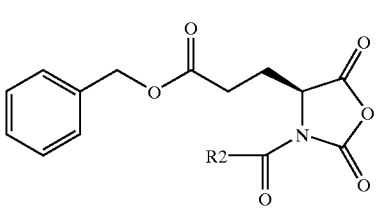
| Compound No. | R2 |
|---|---|
| 18001 | CH3 |
| 18002 | CH2CH3 |
| 18003 | (CH2)2CH3 |
| 18004 | CH(CH3)2 |
| 18005 | (CH2)3CH3 |
| 18006 | CH2CH(CH3)2 |
| 18007 | CH(CH3)CH2CH3 |
| 18008 | C(CH3)3 |
| 18009 | (CH2)4CH3 |
| 18010 | (CH2)5CH3 |
| 18011 | (CH2)6CH3 |
| 18012 | (CH2)7CH3 |
| 18013 | (CH2)8CH3 |
| 18014 | cyclopropyl |
| 18015 | cyclobutyl |
| 18016 | cyclohexyl |
| 18017 | Ph |
| 18018 | PhCH2 |
| 18019 | Ph(CH2)2 |
| 18020 | Ph(CH2)3 |
| 18021 | PhO(CH2)2 |
| 18022 | PhCH2OCH2CH2 |
| 18023 | PhCH2O(C=O)CH2CH2 |
| 18024 | o-CH3Ph |
| 18025 | m-CH3Ph |
| 18026 | p-CH3Ph |
| 18027 | 2,4-(CH3)2Ph |
| 18028 | 3,5-(CH3)2Ph |
| 18029 | 2,4,6-(CH3)3Ph |
| 18030 | p-CH3OPh |
| 18031 | p-CH3CH2OPh |
| 18032 | p-CH3(CH2)2OPh |
| 18033 | p-FPh |
| 18034 | p-ClPh |
| 18035 | p-BrPh |
| 18036 | p-IPh |
| 18037 | p-PhOPh |
| 18038 | p-PhCH2OPh |

TABLE 18-continued
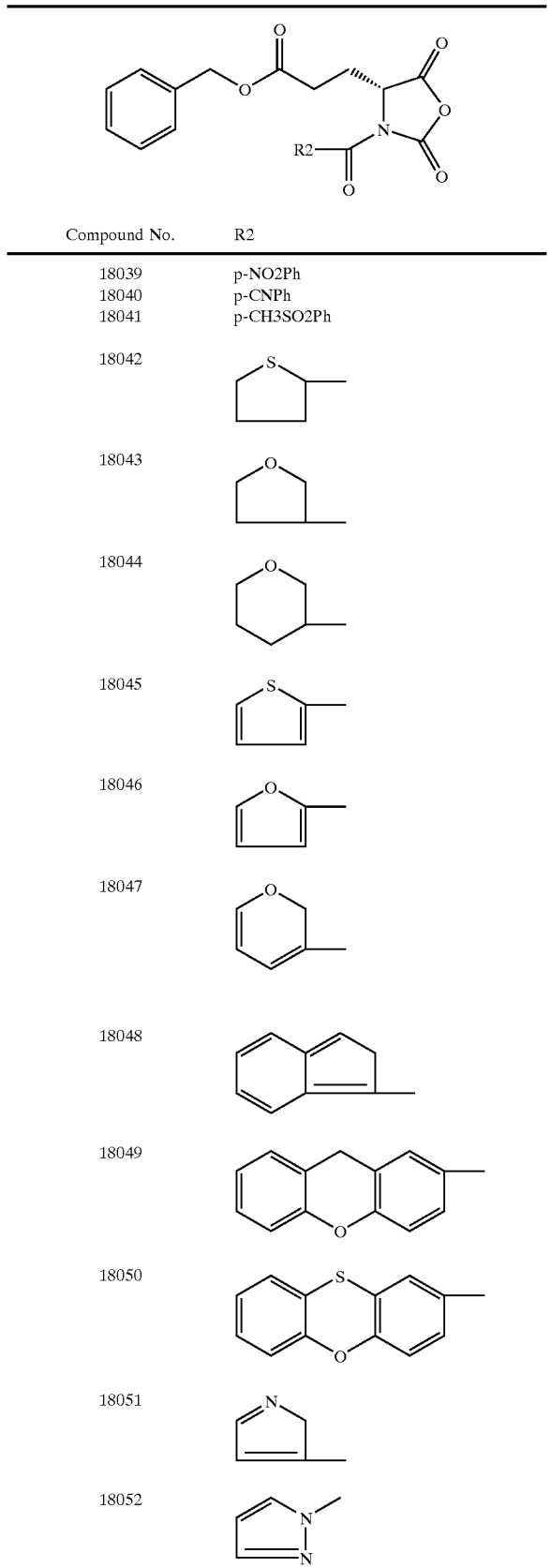
| Compound No. | R2 |
|---|---|
| 18039 | p-NO2Ph |
| 18040 | p-CNPh |
| 18041 | p-CH3SO2Ph |
| 18042 | |
| 18043 | |
| 18044 | |
| 18045 | |
| 18046 | |
| 18047 | |
| 18048 | |
| 18049 | |
| 18050 | |
| 18051 | |
| 18052 | |
TABLE 18-continued
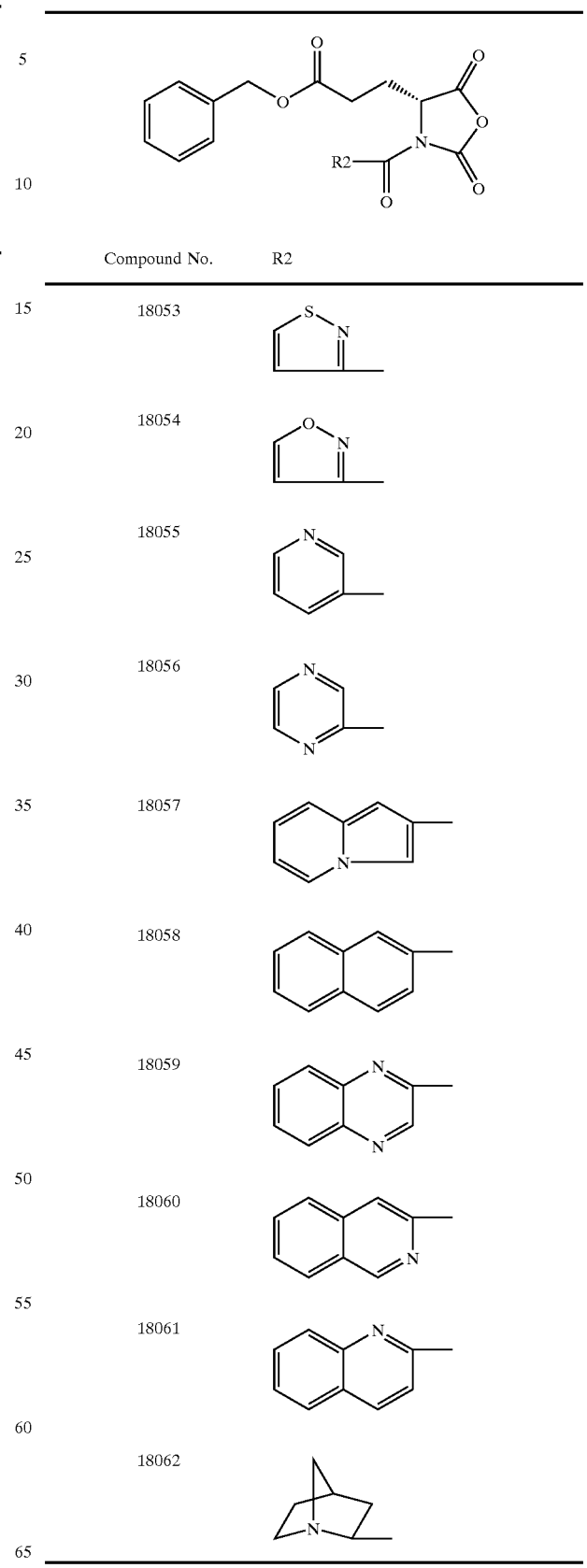
| Compound No. | R2 |
|---|---|
| 18053 | |
| 18054 | |
| 18055 | |
| 18056 | |
| 18057 | |
| 18058 | |
| 18059 | |
| 18060 | |
| 18061 | |
| 18062 | |

TABLE 19
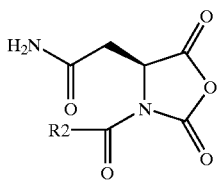
| Compound No. | R2 |
|---|---|
| 19001 | CH3 |
| 19002 | CH2CH3 |
| 19003 | (CH2)2CH3 |
| 19004 | CH(CH3)2 |
| 19005 | (CH2)3CH3 |
| 19006 | CH2CH(CH3)2 |
| 19007 | CH(CH3)CH2CH3 |
| 19008 | C(CH3)3 |
| 19009 | (CH2)4CH3 |
| 19010 | (CH2)5CH3 |
| 19011 | (CH2)6CH3 |
| 19012 | (CH2)7CH3 |
| 19013 | (CH2)8CH3 |
| 19014 | cyclopropyl |
| 19015 | cyclobutyl |
| 19016 | cyclohexyl |
| 19017 | Ph |
| 19018 | PhCH2 |
| 19019 | Ph(CH2)2 |
| 19020 | Ph(CH2)3 |
| 19021 | PhO(CH2)2 |
| 19022 | PhCH2OCH2CH2 |
| 19023 | PhCH2O(C=O)CH2CH2 |
| 19024 | o-CH3Ph |
| 19025 | m-CH3Ph |
| 19026 | p-CH3Ph |
| 19027 | 2,4-(CH3)2Ph |
| 19028 | 3,5-(CH3)2Ph |
| 19029 | 2,4,6-(CH3)3Ph |
| 19030 | p-CH3OPh |
| 19031 | p-CH3CH2OPh |
| 19032 | p-CH3(CH2)2OPh |
| 19033 | p-FPh |
| 19034 | p-ClPh |
| 19035 | p-BrPh |
| 19036 | p-IPh |
| 19037 | p-PhOPh |
| 19038 | p-PhCH2OPh |
| 19039 | p-NO2Ph |
| 19040 | p-CNPh |
| 19041 | p-CH3SO2Ph |
| 19042 | 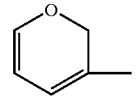 |
| 19043 | 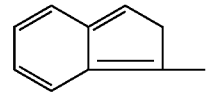 |
| 19044 | 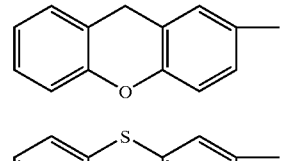 |
| 19045 | 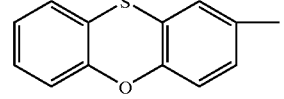 |
| 19046 | 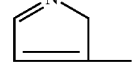 |
TABLE 19-continued
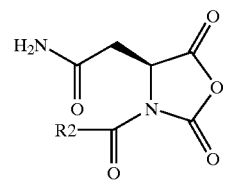
| Compound No. | R2 |
|---|---|
| 19047 | 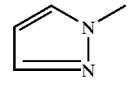 |
| 19048 | 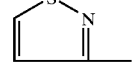 |
| 19049 | 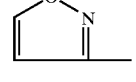 |
| 19050 | 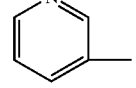 |
| 19051 | 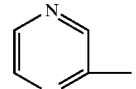 |
| 19052 | 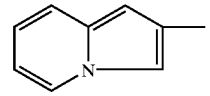 |
| 19053 | 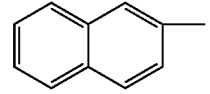 |
| 19054 | 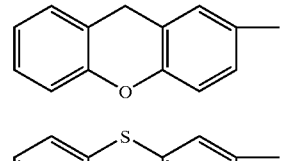 |
| 19055 | 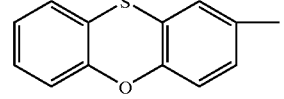 |
| 19056 | 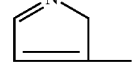 |
| 19057 | 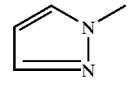 |
| 19058 | 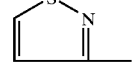 |

TABLE 19-continued
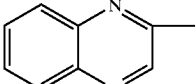
| Compound No. | R2 |
|---|---|
| 19059 | 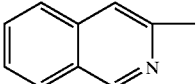 |
| 19060 | 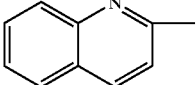 |
| 19061 |  |
| 19062 | 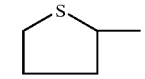 |
TABLE 20
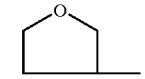
| Compound No. | R2 |
|---|---|
| 20001 | CH3 |
| 20002 | CH2CH3 |
| 20003 | (CH2)2CH3 |
| 20004 | CH(CH3)2 |
| 20005 | (CH2)3CH3 |
| 20006 | CH2CH(CH3)2 |
| 20007 | CH(CH3)CH2CH3 |
| 20008 | C(CH3)3 |
| 20009 | (CH2)4CH3 |
| 20010 | (CH2)5CH3 |
| 20011 | (CH2)6CH3 |
| 20012 | (CH2)7CH3 |
| 20013 | (CH2)8CH3 |
| 20014 | cyclopropyl |
| 20015 | cyclobutyl |
| 20016 | cyclohexyl |
| 20017 | Ph |
| 20018 | PhCH2 |
| 20019 | Ph(CH2)2 |
| 20020 | Ph(CH2)3 |
| 20021 | PhO(CH2)2 |
| 20022 | PhCH2OCH2CH2 |
| 20023 | PhCH2O(C=O)CH2CH2 |
| 20024 | o-CH3Ph |
| 20025 | m-CH3Ph |
| 20026 | p-CH3Ph |
| 20027 | 2,4-(CH3)2Ph |
| 20028 | 3,5-(CH3)2Ph |
TABLE 20-continued
| Compound No. | R2 |
|---|---|
| 20029 | 2,4,6-(CH3)3Ph |
| 20030 | p-CH3OPh |
| 20031 | p-CH3CH2OPh |
| 20032 | p-CH3(CH2)2OPh |
| 20033 | p-FPh |
| 20034 | p-ClPh |
| 20035 | p-BrPh |
| 20036 | p-IPh |
| 20037 | p-PhOPh |
| 20038 | p-PhCH2OPh |
| 20039 | p-NO2Ph |
| 20040 | p-CNPh |
| 20041 | p-CH3SO2Ph |
| 20042 | 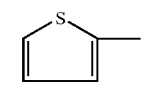 |
| 20043 | 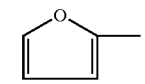 |
| 20044 | 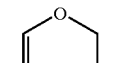 |
| 20045 | 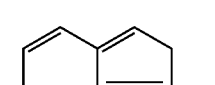 |
| 20046 | 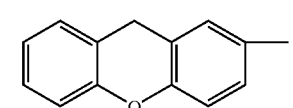 |
| 20047 | 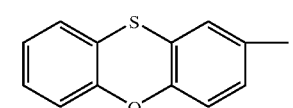 |
| 20048 | 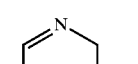 |
| 20049 | 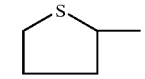 |
| 20050 | 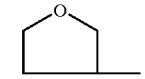 |
| 20051 |  |

TABLE 20-continued

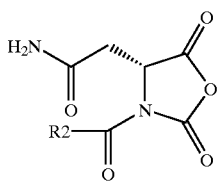

| Compound No. | R2 |
|---|---|
| 20052 | 1-methylpyrazol-3-yl |
| 20053 | isothiazol-3-yl |
| 20054 | isoxazol-3-yl |
| 20055 | pyridin-3-yl |
| 20056 | pyrazin-2-yl |
| 20057 | indolizin-2-yl |
| 20058 | naphthalen-2-yl |
| 20059 | quinoxalin-2-yl |
| 20060 | isoquinolin-3-yl |
| 20061 | quinolin-2-yl |
| 20062 | quinuclidin-2-yl |

TABLE 21

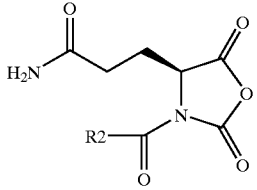

| Compound No. | R2 |
|---|---|
| 21001 | CH3 |
| 21002 | CH2CH3 |
| 21003 | (CH2)2CH3 |
| 21004 | CH(CH3)2 |
| 21005 | (CH2)3CH3 |
| 21006 | CH2CH(CH3)2 |
| 21007 | CH(CH3)CH2CH3 |
| 21008 | C(CH3)3 |
| 21009 | (CH2)4CH3 |
| 21010 | (CH2)5CH3 |
| 21011 | (CH2)6CH3 |
| 21012 | (CH2)7CH3 |
| 21013 | (CH2)8CH3 |
| 21014 | cyclopropyl |
| 21015 | cyclobutyl |
| 21016 | cyclohexyl |
| 21017 | Ph |
| 21018 | PhCH2 |
| 21019 | Ph(CH2)2 |
| 21020 | Ph(CH2)3 |
| 21021 | PhO(CH2)2 |
| 21022 | PhCH2OCH2CH2 |
| 21023 | PhCH2O(C=O)CH2CH2 |
| 21024 | o-CH3Ph |
| 21025 | m-CH3Ph |
| 21026 | p-CH3Ph |
| 21027 | 2,4-(CH3)2Ph |
| 21028 | 3,5-(CH3)2Ph |
| 21029 | 2,4,6-(CH3)3Ph |
| 21030 | p-CH3OPh |
| 21031 | p-CH3CH2OPh |
| 21032 | p-CH3(CH2)2OPh |
| 21033 | p-FPh |
| 21034 | p-ClPh |
| 21035 | p-BrPh |
| 21036 | p-IPh |
| 21037 | p-PhOPh |
| 21038 | p-PhCH2OPh |
| 21039 | p-NO2Ph |
| 21040 | p-CNPh |
| 21041 | p-CH3SO2Ph |
| 21042 | 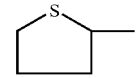 |
| 21043 | 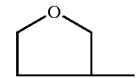 |
| 21044 | 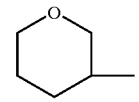 |
| 21045 | 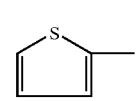 |
| 21046 | 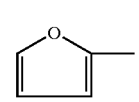 |

TABLE 21-continued
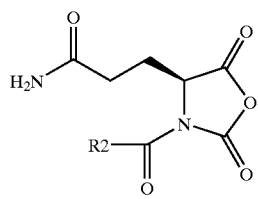
| Compound No. | R2 |
|---|---|
| 21047 | |
| 21048 | |
| 21049 | |
| 21050 | |
| 21051 | |
| 21052 | |
| 21053 | |
| 21054 | |
| 21055 | |
| 21056 | |
| 21057 | |
| 21058 | |
TABLE 21-continued
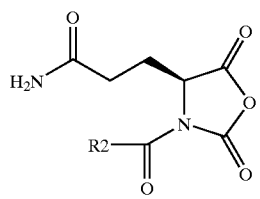
| Compound No. | R2 |
|---|---|
| 21059 | |
| 21060 | |
| 21061 | |
| 21062 | |
TABLE 22
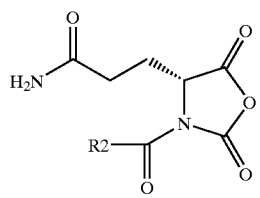
| Compound No. | R2 |
|---|---|
| 22001 | CH3 |
| 22002 | CH2CH3 |
| 22003 | (CH2)2CH3 |
| 22004 | CH(CH3)2 |
| 22005 | (CH2)3CH3 |
| 22006 | CH2CH(CH3)2 |
| 22007 | CH(CH3)CH2CH3 |
| 22008 | C(CH3)3 |
| 22009 | (CH2)4CH3 |
| 22010 | (CH2)5CH3 |
| 22011 | (CH2)6CH3 |
| 22012 | (CH2)7CH3 |
| 22013 | (CH2)8CH3 |
| 22014 | cyclopropyl |
| 22015 | cyclobutyl |
| 22016 | cyclohexyl |
| 22017 | Ph |
| 22018 | PhCH2 |
| 22019 | Ph(CH2)2 |
| 22020 | Ph(CH2)3 |
| 22021 | PhO(CH2)2 |
| 22022 | PhCH2OCH2CH2 |
| 22023 | PhCH2O(C=O)CH2CH2 |
| 22024 | o-CH3Ph |
| 22025 | m-CH3Ph |
| 22026 | p-CH3Ph |
| 22027 | 2,4-(CH3)2Ph |

TABLE 22-continued

| Compound No. | R2 |
|---|---|
| 22028 | 3,5-(CH3)2Ph |
| 22029 | 2,4,6-(CH3)3Ph |
| 22030 | p-CH3OPh |
| 22031 | p-CH3CH2OPh |
| 22032 | p-CH3(CH2)2OPh |
| 22033 | p-FPh |
| 22034 | p-ClPh |
| 22035 | p-BrPh |
| 22036 | p-IPh |
| 22037 | p-PhOPh |
| 22038 | p-PhCH2OPh |
| 22039 | p-NO2Ph |
| 22040 | p-CNPh |
| 22041 | p-CH3SO2Ph |
| 22042 | (tetrahydrothiophen-2-yl) |
| 22043 | (tetrahydrofuran-2-yl) |
| 22044 | (tetrahydropyran-2-yl) |
| 22045 | (thiophen-2-yl) |
| 22046 | (furan-2-yl) |
| 22047 | (2H-pyran-3-yl) |
| 22048 | (1H-inden-2-yl) |
| 22049 | (9H-xanthen-2-yl) |
| 22050 | (phenoxathiin-2-yl) |
| 22051 | (1H-pyrrol-2-yl) |
| 22052 | (1-methyl-1H-pyrazol-3-yl) |
| 22053 | (isothiazol-3-yl) |
| 22054 | (isoxazol-3-yl) |
| 22055 | (pyridin-3-yl) |
| 22056 | (pyrazin-2-yl) |
| 22057 | (indolizin-2-yl) |
| 22058 | (naphthalen-2-yl) |
| 22059 | (quinoxalin-2-yl) |
| 22060 | (isoquinolin-3-yl) |
| 22061 | (quinolin-2-yl) |
| 22062 | (1-azabicyclo[2.2.1]heptan-2-yl) |

TABLE 23

[Structure: BocNH-(CH2)4-C(H)(C=O)-N(C(=O)R2)-O-C(=O) oxazolidinedione]

| Compound No. | R2 |
|---|---|
| 23001 | CH3 |
| 23002 | CH2CH3 |
| 23003 | (CH2)2CH3 |
| 23004 | CH(CH3)2 |
| 23005 | (CH2)3CH3 |
| 23006 | CH2CH(CH3)2 |
| 23007 | CH(CH3)CH2CH3 |
| 23008 | C(CH3)3 |
| 23009 | (CH2)4CH3 |
| 23010 | (CH2)5CH3 |
| 23011 | (CH2)6CH3 |
| 23012 | (CH2)7CH3 |
| 23013 | (CH2)8CH3 |
| 23014 | cyclopropyl |
| 23015 | cyclobutyl |
| 23016 | cyclohexyl |
| 23017 | Ph |
| 23018 | PhCH2 |
| 23019 | Ph(CH2)2 |
| 23020 | Ph(CH2)3 |
| 23021 | PhO(CH2)2 |
| 23022 | PhCH2OCH2CH2 |
| 23023 | PhCH2O(C=O)CH2CH2 |
| 23024 | o-CH3Ph |
| 23025 | m-CH3Ph |
| 23026 | p-CH3Ph |
| 23027 | 2,4-(CH3)2Ph |
| 23028 | 3,5-(CH3)2Ph |
| 23029 | 2,4,6-(CH3)3Ph |
| 23030 | p-CH3OPh |
| 23031 | p-CH3CH2OPh |
| 23032 | p-CH3(CH2)2OPh |
| 23033 | p-FPh |
| 23034 | p-ClPh |
| 23035 | p-BrPh |
| 23036 | p-IPh |
| 23037 | p-PhOPh |
| 23038 | p-PhCH2OPh |
| 23039 | p-NO2Ph |
| 23040 | p-CNPh |
| 23041 | p-CH3SO2Ph |
| 23042 | tetrahydrothiophen-2-yl |
| 23043 | tetrahydrofuran-2-yl |
| 23044 | tetrahydropyran-2-yl |
| 23045 | thiophen-2-yl |
| 23046 | furan-2-yl |
| 23047 | 2H-pyran-3-yl |
| 23048 | indene-yl |
| 23049 | xanthene-yl |
| 23050 | phenoxathiin-yl |
| 23051 | pyrrole-yl |
| 23052 | N-methylpyrazol-yl |
| 23053 | isothiazol-yl |
| 23054 | isoxazol-yl |
| 23055 | pyridin-3-yl |
| 23056 | pyrazin-2-yl |
| 23057 | indolizin-yl |
| 23058 | naphthalen-2-yl |

TABLE 23-continued
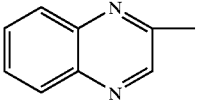
| Compound No. | R2 |
|---|---|
| 23059 | 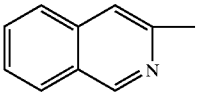 |
| 23060 | 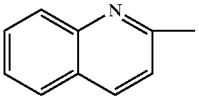 |
| 23061 | 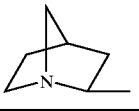 |
| 23062 | 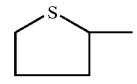 |
TABLE 24
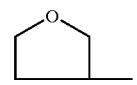
| Compound No. | R2 |
|---|---|
| 24001 | CH3 |
| 24002 | CH2CH3 |
| 24003 | (CH2)2CH3 |
| 24004 | CH(CH3)2 |
| 24005 | (CH2)3CH3 |
| 24006 | CH2CH(CH3)2 |
| 24007 | CH(CH3)CH2CH3 |
| 24008 | C(CH3)3 |
| 24009 | (CH2)4CH3 |
| 24010 | (CH2)5CH3 |
| 24011 | (CH2)6CH3 |
| 24012 | (CH2)7CH3 |
| 24013 | (CH2)8CH3 |
| 24014 | cyclopropyl |
| 24015 | cyclobutyl |
| 24016 | cyclohexyl |
| 24017 | Ph |
| 24018 | PhCH2 |
| 24019 | Ph(CH2)2 |
| 24020 | Ph(CH2)3 |
| 24021 | PhO(CH2)2 |
| 24022 | PhCH2OCH2CH2 |
| 24023 | PhCH2O(C=O)CH2CH2 |
| 24024 | o-CH3Ph |
| 24025 | m-CH3Ph |
| 24026 | p-CH3Ph |
| 24027 | 2,4-(CH3)2Ph |
| 24028 | 3,5-(CH3)2Ph |
TABLE 24-continued
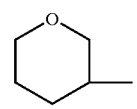
| Compound No. | R2 |
|---|---|
| 24029 | 2,4,6-(CH3)3Ph |
| 24030 | p-CH3OPh |
| 24031 | p-CH3CH2OPh |
| 24032 | p-CH3(CH2)2OPh |
| 24033 | p-FPh |
| 24034 | p-ClPh |
| 24035 | p-BrPh |
| 24036 | p-IPh |
| 24037 | p-PhOPh |
| 24038 | p-PhCH2OPh |
| 24039 | p-NO2Ph |
| 24040 | p-CNPh |
| 24041 | p-CH3SO2Ph |
| 24042 | 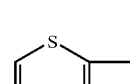 |
| 24043 | 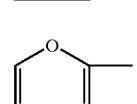 |
| 24044 | 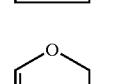 |
| 24045 | 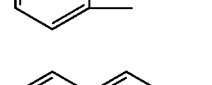 |
| 24046 | 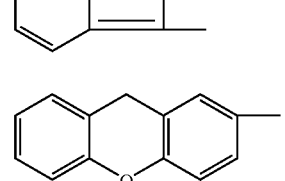 |
| 24047 | 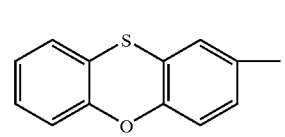 |
| 24048 |  |
| 24049 |  |
| 24050 |  |

TABLE 24-continued
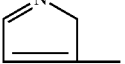
| Compound No. | R2 |
|---|---|
| 24051 | 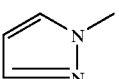 |
| 24052 | 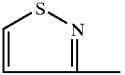 |
| 24053 | 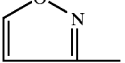 |
| 24054 | 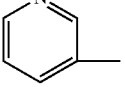 |
| 24055 | 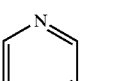 |
| 24056 | 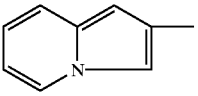 |
| 24057 | 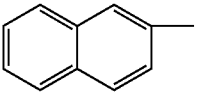 |
| 24058 | 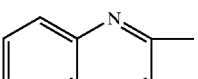 |
| 24059 | 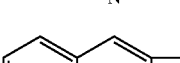 |
| 24060 | 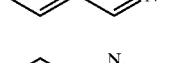 |
| 24061 |  |
| 24062 | 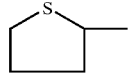 |
TABLE 25
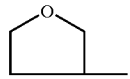
| Compound No. | R2 |
|---|---|
| 25001 | CH3 |
| 25002 | CH2CH3 |
| 25003 | (CH2)2CH3 |
| 25004 | CH(CH3)2 |
| 25005 | (CH2)3CH3 |
| 25006 | CH2CH(CH3)2 |
| 25007 | CH(CH3)CH2CH3 |
| 25008 | C(CH3)3 |
| 25009 | (CH2)4CH3 |
| 25010 | (CH2)5CH3 |
| 25011 | (CH2)6CH3 |
| 25012 | (CH2)7CH3 |
| 25013 | (CH2)8CH3 |
| 25014 | cyclopropyl |
| 25015 | cyclobutyl |
| 25016 | cyclohexyl |
| 25017 | Ph |
| 25018 | PhCH2 |
| 25019 | Ph(CH2)2 |
| 25020 | Ph(CH2)3 |
| 25021 | PhO(CH2)2 |
| 25022 | PhCH2OCH2CH2 |
| 25023 | PhCH2O(C=O)CH2CH2 |
| 25024 | o-CH3Ph |
| 25025 | m-CH3Ph |
| 25026 | p-CH3Ph |
| 25027 | 2,4-(CH3)2Ph |
| 25028 | 3,5-(CH3)2Ph |
| 25029 | 2,4,6-(CH3)3Ph |
| 25030 | p-CH3OPh |
| 25031 | p-CH3CH2OPh |
| 25032 | p-CH3(CH2)2OPh |
| 25033 | p-FPh |
| 25034 | p-ClPh |
| 25035 | p-BrPh |
| 25036 | p-IPh |
| 25037 | p-PhOPh |
| 25038 | p-PhCH2OPh |
| 25039 | p-NO2Ph |
| 25040 | p-CNPh |
| 25041 | p-CH3SO2Ph |
| 25042 | 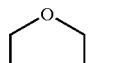 |
| 25043 | 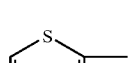 |
| 25044 |  |
| 25045 |  |

TABLE 25-continued
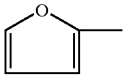
| Compound No. | R2 |
|---|---|
| 25046 | 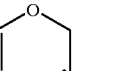 |
| 25047 | 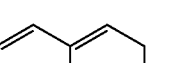 |
| 25048 | 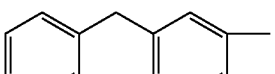 |
| 25049 | 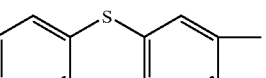 |
| 25050 | 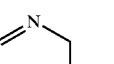 |
| 25051 | 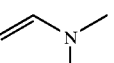 |
| 25052 | 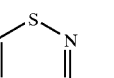 |
| 25053 | 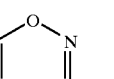 |
| 25054 | 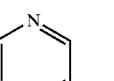 |
| 25055 | 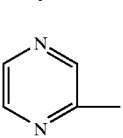 |
| 25056 |  |
| 25057 | 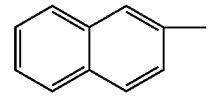 |
TABLE 25-continued
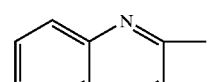
| Compound No. | R2 |
|---|---|
| 25058 | 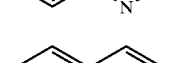 |
| 25059 | 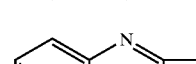 |
| 25060 |  |
| 25061 | 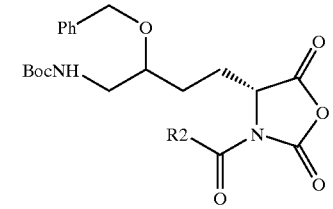 |
| 25062 | |
TABLE 26
| Compound No. | R2 |
|---|---|
| 26001 | CH3 |
| 26002 | CH2CH3 |
| 26003 | (CH2)2CH3 |
| 26004 | CH(CH3)2 |
| 26005 | (CH2)3CH3 |
| 26006 | CH2CH(CH3)2 |
| 26007 | CH(CH3)CH2CH3 |
| 26008 | C(CH3)3 |
| 26009 | (CH2)4CH3 |
| 26010 | (CH2)5CH3 |
| 26011 | (CH2)6CH3 |
| 26012 | (CH2)7CH3 |
| 26013 | (CH2)8CH3 |
| 26014 | cyclopropyl |
| 26015 | cyclobutyl |
| 26016 | cyclohexyl |
| 26017 | Ph |
| 26018 | PhCH2 |
| 26019 | Ph(CH2)2 |
| 26020 | Ph(CH2)3 |

TABLE 26-continued

[Structure: BocNH-CH2-CH(OCH2Ph)-CH2-CH2-[(S)-oxazolidine-2,5-dione with N-C(=O)-R2]]

| Compound No. | R2 |
|---|---|
| 26021 | PhO(CH2)2 |
| 26022 | PhCH2OCH2CH2 |
| 26023 | PhCH2O(C=O)CH2CH2 |
| 26024 | o-CH3Ph |
| 26025 | m-CH3Ph |
| 26026 | p-CH3Ph |
| 26027 | 2,4-(CH3)2Ph |
| 26028 | 3,5-(CH3)2Ph |
| 26029 | 2,4,6-(CH3)3Ph |
| 26030 | p-CH3OPh |
| 26031 | p-CH3CH2OPh |
| 26032 | p-CH3(CH2)2OPh |
| 26033 | p-FPh |
| 26034 | p-ClPh |
| 26035 | p-BrPh |
| 26036 | p-IPh |
| 26037 | p-PhOPh |
| 26038 | p-PhCH2OPh |
| 26039 | p-NO2Ph |
| 26040 | p-CNPh |
| 26041 | p-CH3SO2Ph |
| 26042 | tetrahydrothiophen-2-yl |
| 26043 | tetrahydrofuran-2-yl |
| 26044 | tetrahydropyran-3-yl |
| 26045 | thiophen-2-yl |
| 26046 | furan-2-yl |
| 26047 | 2H-pyran-3-yl |
| 26048 | indene |
| 26049 | xanthene |
| 26050 | phenoxathiine |
| 26051 | pyridin-3-yl |
| 26052 | 1-methylpyrazol-3-yl |
| 26053 | isothiazol-3-yl |
| 26054 | isoxazol-3-yl |
| 26055 | pyridin-3-yl |
| 26056 | pyrazin-2-yl |
| 26057 | indolizin-2-yl |
| 26058 | naphthalen-2-yl |
| 26059 | quinoxalin-2-yl |
| 26060 | isoquinolin-3-yl |
| 26061 | quinolin-2-yl |

TABLE 26-continued

| Compound No. | R2 |
|---|---|
| 26062 | (quinuclidine) |

TABLE 27

(structure with NHBoc, NBoc, NBoc guanidine-propyl oxazolidinedione with R2-C(=O)-N)

| Compound No. | R2 |
|---|---|
| 27001 | CH3 |
| 27002 | CH2CH3 |
| 27003 | (CH2)2CH3 |
| 27004 | CH(CH3)2 |
| 27005 | (CH2)3CH3 |
| 27006 | CH2CH(CH3)2 |
| 27007 | CH(CH3)CH2CH3 |
| 27008 | C(CH3)3 |
| 27009 | (CH2)4CH3 |
| 27010 | (CH2)5CH3 |
| 27011 | (CH2)6CH3 |
| 27012 | (CH2)7CH3 |
| 27013 | (CH2)8CH3 |
| 27014 | cyclopropyl |
| 27015 | cyclobutyl |
| 27016 | cyclohexyl |
| 27017 | Ph |
| 27018 | PhCH2 |
| 27019 | Ph(CH2)2 |
| 27020 | Ph(CH2)3 |
| 27021 | PhO(CH2)2 |
| 27022 | PhCH2OCH2CH2 |
| 27023 | PhCH2O(C=O)CH2CH2 |
| 27024 | o-CH3Ph |
| 27025 | m-CH3Ph |
| 27026 | p-CH3Ph |
| 27027 | 2,4-(CH3)2Ph |
| 27028 | 3,5-(CH3)2Ph |
| 27029 | 2,4,6-(CH3)3Ph |
| 27030 | p-CH3OPh |
| 27031 | p-CH3CH2OPh |
| 27032 | p-CH3(CH2)2OPh |
| 27033 | p-FPh |
| 27034 | p-ClPh |
| 27035 | p-BrPh |
| 27036 | p-IPh |
| 27037 | p-PhOPh |
| 27038 | p-PhCH2OPh |
| 27039 | p-NO2Ph |
| 27040 | p-CNPh |
| 27041 | p-CH3SO2Ph |

TABLE 27-continued (same structure)

| Compound No. | R2 |
|---|---|
| 27042 | tetrahydrothiophen-2-yl |
| 27043 | tetrahydrofuran-3-yl |
| 27044 | tetrahydropyran-3-yl |
| 27045 | thiophen-2-yl |
| 27046 | furan-2-yl |
| 27047 | 3,6-dihydro-2H-pyran-3-yl |
| 27048 | indan-2-yl |
| 27049 | xanthenyl |
| 27050 | phenoxathiinyl |
| 27051 | 2H-pyrrol-3-yl |
| 27052 | 1-methylpyrazol-3-yl |

TABLE 27-continued
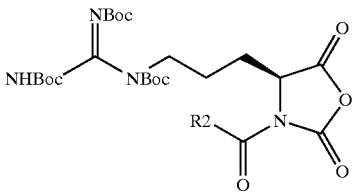
| Compound No. | R2 |
|---|---|
| 27053 | 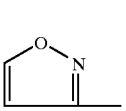 |
| 27054 | 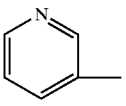 |
| 27055 | 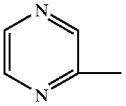 |
| 27056 | 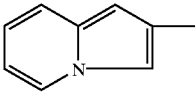 |
| 27057 | 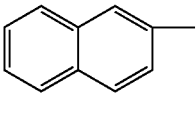 |
| 27058 | 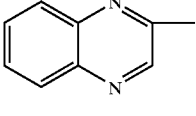 |
| 27059 | 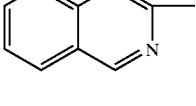 |
| 27060 | 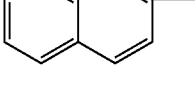 |
| 27061 | 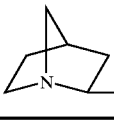 |
| 27062 | 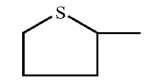 |
TABLE 28
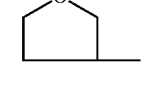
| Compound No. | R2 |
|---|---|
| 28001 | CH3 |
| 28002 | CH2CH3 |
| 28003 | (CH2)2CH3 |
| 28004 | CH(CH3)2 |
| 28005 | (CH2)3CH3 |
| 28006 | CH2CH(CH3)2 |
| 28007 | CH(CH3)CH2CH3 |
| 28008 | C(CH3)3 |
| 28009 | (CH2)4CH3 |
| 28010 | (CH2)5CH3 |
| 28011 | (CH2)6CH3 |
| 28012 | (CH2)7CH3 |
| 28013 | (CH2)8CH3 |
| 28014 | cyclopropyl |
| 28015 | cyclobutyl |
| 28016 | cyclohexyl |
| 28017 | Ph |
| 28018 | PhCH2 |
| 28019 | Ph(CH2)2 |
| 28020 | Ph(CH2)3 |
| 28021 | PhO(CH2)2 |
| 28022 | PhCH2OCH2CH2 |
| 28023 | PhCH2O(C=O)CH2CH2 |
| 28024 | o-CH3Ph |
| 28025 | m-CH3Ph |
| 28026 | p-CH3Ph |
| 28027 | 2,4-(CH3)2Ph |
| 28028 | 3,5-(CH3)2Ph |
| 28029 | 2,4,6-(CH3)3Ph |
| 28030 | p-CH3OPh |
| 28031 | p-CH3CH2OPh |
| 28032 | p-CH3(CH2)2OPh |
| 28033 | p-FPh |
| 28034 | p-ClPh |
| 28035 | p-BrPh |
| 28036 | p-IPh |
| 28037 | p-PhOPh |
| 28038 | p-PhCH2OPh |
| 28039 | p-NO2Ph |
| 28040 | p-CNPh |
| 28041 | p-CH3SO2Ph |
| 28042 | 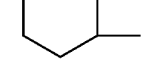 |
| 28043 | |
| 28044 | 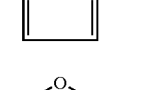 |
| 28045 | |
| 28046 |  |

TABLE 28-continued

[Structure: NHBoc-N(Boc)=NBoc-propyl-oxazolidinedione with R2-C(=O)- on N]

| Compound No. | R2 |
|---|---|
| 28047 | [2H-pyran-3-yl] |
| 28048 | [indene] |
| 28049 | [xanthene-2-yl] |
| 28050 | [phenoxathiine] |
| 28051 | [pyrrole] |
| 28052 | [N-methylpyrazole] |
| 28053 | [isothiazole] |
| 28054 | [isoxazole] |
| 28055 | [pyridin-3-yl] |
| 28056 | [pyrazin-2-yl] |
| 28057 | [indolizine] |
| 28058 | [naphthalen-2-yl] |

TABLE 28-continued

[Structure: NHBoc-N(Boc)=NBoc-propyl-oxazolidinedione with R2-C(=O)- on N]

| Compound No. | R2 |
|---|---|
| 28059 | [quinoxalin-2-yl] |
| 28060 | [isoquinolin-3-yl] |
| 28061 | [quinolin-2-yl] |
| 28062 | [quinuclidine] |

TABLE 29

[Structure: H3C-S-CH2-oxazolidinedione with R2-C(=O)- on N]

| Compound No. | R2 |
|---|---|
| 29001 | CH3 |
| 29002 | CH2CH3 |
| 29003 | (CH2)2CH3 |
| 29004 | CH(CH3)2 |
| 29005 | (CH2)3CH3 |
| 29006 | CH2CH(CH3)2 |
| 29007 | CH(CH3)CH2CH3 |
| 29008 | C(CH3)3 |
| 29009 | (CH2)4CH3 |
| 29010 | (CH2)5CH3 |
| 29011 | (CH2)6CH3 |
| 29012 | (CH2)7CH3 |
| 29013 | (CH2)8CH3 |
| 29014 | cyclopropyl |
| 29015 | cyclobutyl |
| 29016 | cyclohexyl |
| 29017 | Ph |
| 29018 | PhCH2 |
| 29019 | Ph(CH2)2 |
| 29020 | Ph(CH2)3 |
| 29021 | PhO(CH2)2 |
| 29022 | PhCH2OCH2CH2 |
| 29023 | PhCH2O(C=O)CH2CH2 |
| 29024 | o-CH3Ph |
| 29025 | m-CH3Ph |
| 29026 | p-CH3Ph |
| 29027 | 2,4-(CH3)2Ph |
| 29028 | 3,5-(CH3)2Ph |

TABLE 29-continued

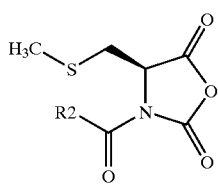

| Compound No. | R2 |
|---|---|
| 29029 | 2,4,6-(CH3)3Ph |
| 29030 | p-CH3OPh |
| 29031 | p-CH3CH2OPh |
| 29032 | p-CH3(CH2)2OPh |
| 29033 | p-FPh |
| 29034 | p-ClPh |
| 29035 | p-BrPh |
| 29036 | p-IPh |
| 29037 | p-PhOPh |
| 29038 | p-PhCH2OPh |
| 29039 | p-NO2Ph |
| 29040 | p-CNPh |
| 29041 | p-CH3SO2Ph |
| 29042 | tetrahydrothiophen-2-yl |
| 29043 | tetrahydrofuran-2-yl |
| 29044 | tetrahydropyran-3-yl |
| 29045 | thiophen-2-yl |
| 29046 | furan-2-yl |
| 29047 | 3,4-dihydro-2H-pyran-3-yl |
| 29048 | indenyl |
| 29049 | xanthen-2-yl |
| 29050 | phenoxathiin-2-yl |
| 29051 | dihydropyridinyl |

TABLE 29-continued

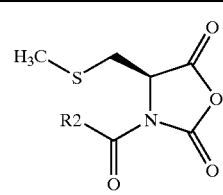

| Compound No. | R2 |
|---|---|
| 29052 | 1-methylpyrazol-3-yl |
| 29053 | isothiazol-3-yl |
| 29054 | isoxazol-3-yl |
| 29055 | pyridin-3-yl |
| 29056 | pyrazin-2-yl |
| 29057 | indolizin-2-yl |
| 29058 | naphth-2-yl |
| 29059 | quinoxalin-2-yl |
| 29060 | isoquinolin-3-yl |
| 29061 | quinolin-2-yl |
| 29062 | quinuclidinyl |

TABLE 30

| Compound No. | R2 |
|---|---|
| 30001 | CH3 |
| 30002 | CH2CH3 |
| 30003 | (CH2)2CH3 |
| 30004 | CH(CH3)2 |
| 30005 | (CH2)3CH3 |
| 30006 | CH2CH(CH3)2 |
| 30007 | CH(CH3)CH2CH3 |
| 30008 | C(CH3)3 |
| 30009 | (CH2)4CH3 |
| 30010 | (CH2)5CH3 |
| 30011 | (CH2)6CH3 |
| 30012 | (CH2)7CH3 |
| 30013 | (CH2)8CH3 |
| 30014 | cyclopropyl |
| 30015 | cyclobutyl |
| 30016 | cyclohexyl |
| 30017 | Ph |
| 30018 | PhCH2 |
| 30019 | Ph(CH2)2 |
| 30020 | Ph(CH2)3 |
| 30021 | PhO(CH2)2 |
| 30022 | PhCH2OCH2CH2 |
| 30023 | PhCH2O(C=O)CH2CH2 |
| 30024 | o-CH3Ph |
| 30025 | m-CH3Ph |
| 30026 | p-CH3Ph |
| 30027 | 2,4-(CH3)2Ph |
| 30028 | 3,5-(CH3)2Ph |
| 30029 | 2,4,6-(CH3)3Ph |
| 30030 | p-CH3OPh |
| 30031 | p-CH3CH2OPh |
| 30032 | p-CH3(CH2)2OPh |
| 30033 | p-FPh |
| 30034 | p-ClPh |
| 30035 | p-BrPh |
| 30036 | p-IPh |
| 30037 | p-PhOPh |
| 30038 | p-PhCH2OPh |
| 30039 | p-NO2Ph |
| 30040 | p-CNPh |
| 30041 | p-CH3SO2Ph |
| 30042 | (tetrahydrothiophen-2-yl) |
| 30043 | (tetrahydrofuran-2-yl) |
| 30044 | (tetrahydropyran-2-yl) |
| 30045 | (thiophen-2-yl) |
| 30046 | (furan-2-yl) |
| 30047 | (2H-pyran-3-yl) |
| 30048 | (1H-indene-2-yl) |
| 30049 | (9H-xanthen-2-yl) |
| 30050 | (phenoxathiin-2-yl) |
| 30051 | (2H-pyrrol-3-yl) |
| 30052 | (1-methyl-1H-pyrazol-3-yl) |
| 30053 | (isothiazol-3-yl) |
| 30054 | (isoxazol-3-yl) |
| 30055 | (pyridin-3-yl) |
| 30056 | (pyrazin-2-yl) |
| 30057 | (indolizin-2-yl) |
| 30058 | (naphthalen-2-yl) |

TABLE 30-continued
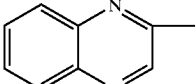
| Compound No. | R2 |
|---|---|
| 30059 | 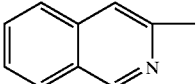 |
| 30060 | 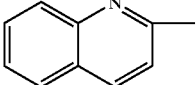 |
| 30061 |  |
| 30062 | 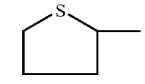 |
TABLE 31
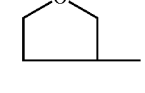
| Compound No. | R2 |
|---|---|
| 31001 | CH3 |
| 31002 | CH2CH3 |
| 31003 | (CH2)2CH3 |
| 31004 | CH(CH3)2 |
| 31005 | (CH2)3CH3 |
| 31006 | CH2CH(CH3)2 |
| 31007 | CH(CH3)CH2CH3 |
| 31008 | C(CH3)3 |
| 31009 | (CH2)4CH3 |
| 31010 | (CH2)5CH3 |
| 31011 | (CH2)6CH3 |
| 31012 | (CH2)7CH3 |
| 31013 | (CH2)8CH3 |
| 31014 | cyclopropyl |
| 31015 | cyclobutyl |
| 31016 | cyclohexyl |
| 31017 | Ph |
| 31018 | PhCH2 |
| 31019 | Ph(CH2)2 |
| 31020 | Ph(CH2)3 |
| 31021 | PhO(CH2)2 |
| 31022 | PhCH2OCH2CH2 |
| 31023 | PhCH2O(C=O)CH2CH2 |
| 31024 | o-CH3Ph |
| 31025 | m-CH3Ph |
| 31026 | p-CH3Ph |
| 31027 | 2,4-(CH3)2Ph |
TABLE 31-continued
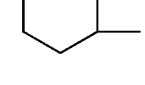
| Compound No. | R2 |
|---|---|
| 31028 | 3,5-(CH3)2Ph |
| 31029 | 2,4,6-(CH3)3Ph |
| 31030 | p-CH3OPh |
| 31031 | p-CH3CH2OPh |
| 31032 | p-CH3(CH2)2OPh |
| 31033 | p-FPh |
| 31034 | p-ClPh |
| 31035 | p-BrPh |
| 31036 | p-IPh |
| 31037 | p-PhOPh |
| 31038 | p-PhCH2OPh |
| 31039 | p-NO2Ph |
| 31040 | p-CNPh |
| 31041 | p-CH3SO2Ph |
| 31042 | 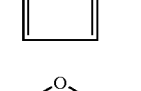 |
| 31043 | 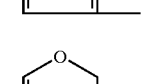 |
| 31044 | 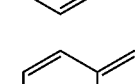 |
| 31045 | 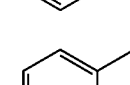 |
| 31046 | |
| 31047 | |
| 31048 | 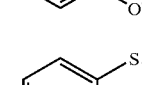 |
| 31049 | |
| 31050 | 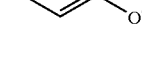 |

TABLE 31-continued

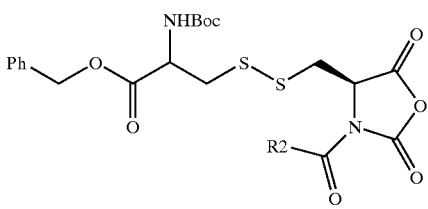

| Compound No. | R2 |
|---|---|
| 31051 | pyridyl |
| 31052 | N-methylpyrazolyl |
| 31053 | isothiazolyl |
| 31054 | isoxazolyl |
| 31055 | pyridyl |
| 31056 | pyrazinyl |
| 31057 | indolizinyl |
| 31058 | naphthyl |
| 31059 | quinoxalinyl |
| 31060 | isoquinolinyl |
| 31061 | quinolinyl |
| 31062 | quinuclidinyl |

TABLE 32

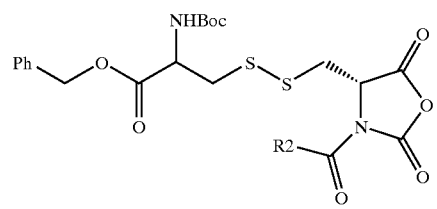

| Compound No. | R2 |
|---|---|
| 32001 | CH3 |
| 32002 | CH2CH3 |
| 32003 | (CH2)2CH3 |
| 32004 | CH(CH3)2 |
| 32005 | (CH2)3CH3 |
| 32006 | CH2CH(CH3)2 |
| 32007 | CH(CH3)CH2CH3 |
| 32008 | C(CH3)3 |
| 32009 | (CH2)4CH3 |
| 32010 | (CH2)5CH3 |
| 32011 | (CH2)6CH3 |
| 32012 | (CH2)7CH3 |
| 32013 | (CH2)8CH3 |
| 32014 | cyclopropyl |
| 32015 | cyclobutyl |
| 32016 | cyclohexyl |
| 32017 | Ph |
| 32018 | PhCH2 |
| 32019 | Ph(CH2)2 |
| 32020 | Ph(CH2)3 |
| 32021 | PhO(CH2)2 |
| 32022 | PhCH2OCH2CH2 |
| 32023 | PhCH2O(C=O)CH2CH2 |
| 32024 | o-CH3Ph |
| 32025 | m-CH3Ph |
| 32026 | p-CH3Ph |
| 32027 | 2,4-(CH3)2Ph |
| 32028 | 3,5-(CH3)2Ph |
| 32029 | 2,4,6-(CH3)3Ph |
| 32030 | p-CH3OPh |
| 32031 | p-CH3CH2OPh |
| 32032 | p-CH3(CH2)2OPh |
| 32033 | p-FPh |
| 32034 | p-ClPh |
| 32035 | p-BrPh |
| 32036 | p-IPh |
| 32037 | p-PhOPh |
| 32038 | p-PhCH2OPh |
| 32039 | p-NO2Ph |
| 32040 | p-CNPh |
| 32041 | p-CH3SO2Ph |
| 32042 | tetrahydrothienyl |
| 32043 | tetrahydrofuranyl |
| 32044 | tetrahydropyranyl |
| 32045 | thienyl |
| 32046 | furyl |

TABLE 32-continued
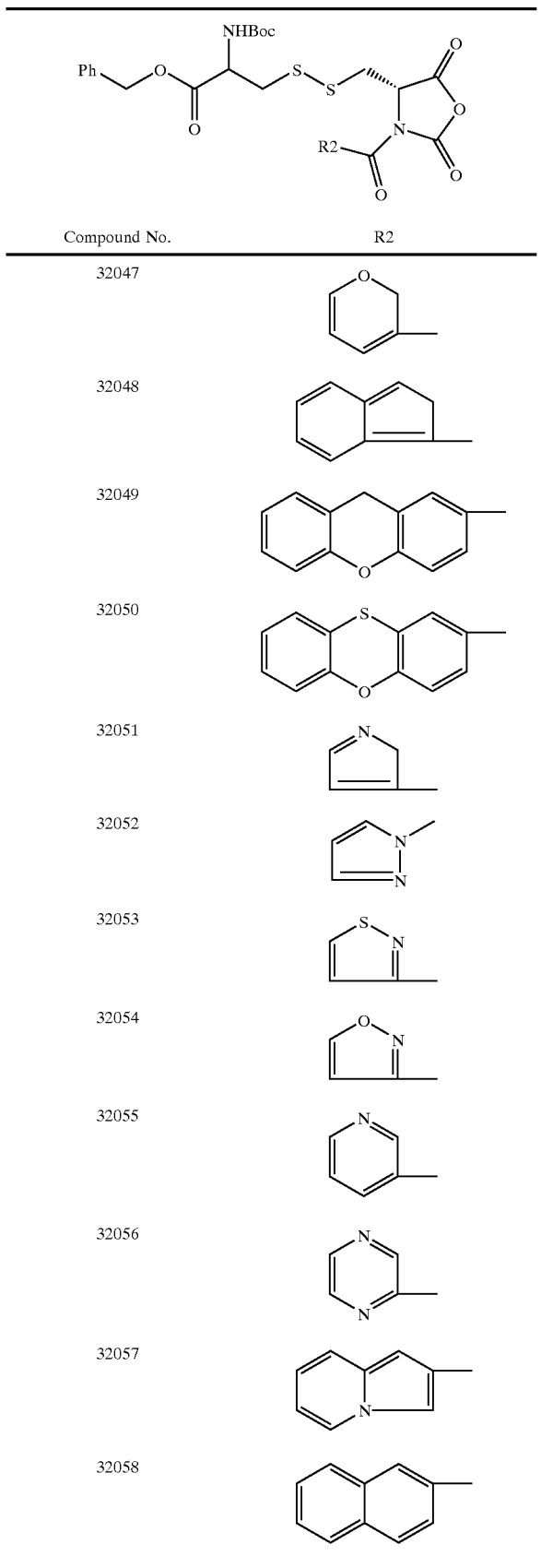
| Compound No. | R2 |
|---|---|
| 32047 | |
| 32048 | |
| 32049 | |
| 32050 | |
| 32051 | |
| 32052 | |
| 32053 | |
| 32054 | |
| 32055 | |
| 32056 | |
| 32057 | |
| 32058 | |
TABLE 32-continued
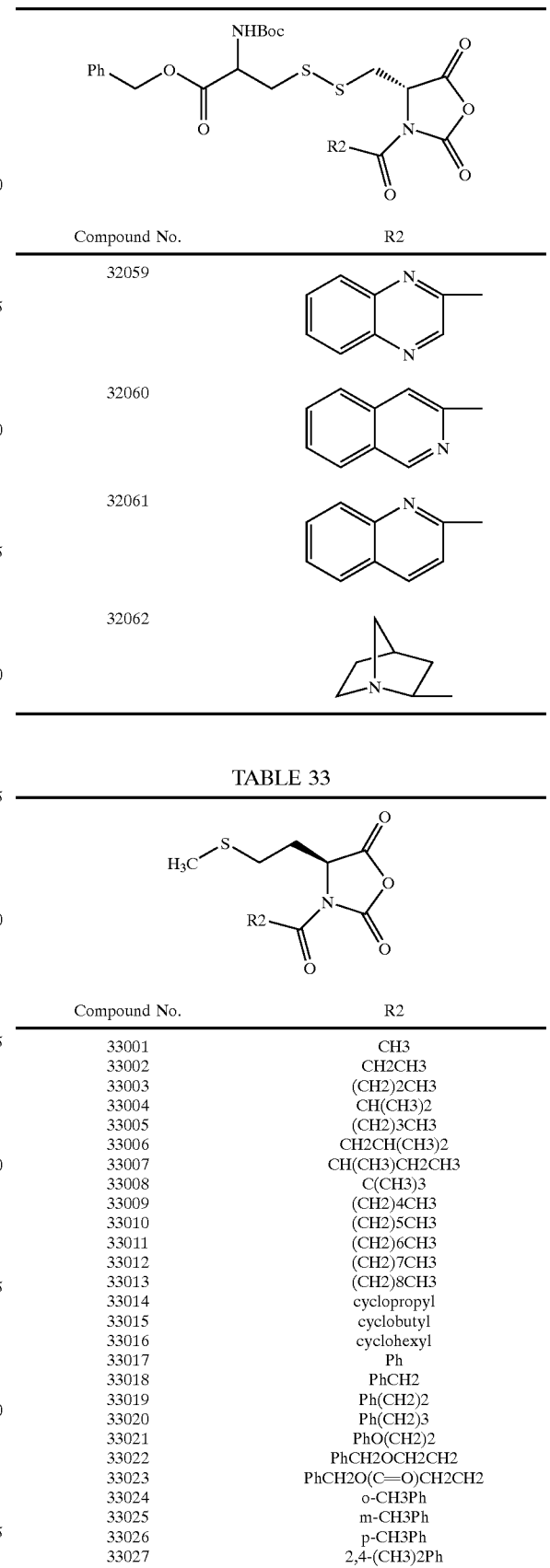
| Compound No. | R2 |
|---|---|
| 32059 | |
| 32060 | |
| 32061 | |
| 32062 | |
TABLE 33
| Compound No. | R2 |
|---|---|
| 33001 | CH3 |
| 33002 | CH2CH3 |
| 33003 | (CH2)2CH3 |
| 33004 | CH(CH3)2 |
| 33005 | (CH2)3CH3 |
| 33006 | CH2CH(CH3)2 |
| 33007 | CH(CH3)CH2CH3 |
| 33008 | C(CH3)3 |
| 33009 | (CH2)4CH3 |
| 33010 | (CH2)5CH3 |
| 33011 | (CH2)6CH3 |
| 33012 | (CH2)7CH3 |
| 33013 | (CH2)8CH3 |
| 33014 | cyclopropyl |
| 33015 | cyclobutyl |
| 33016 | cyclohexyl |
| 33017 | Ph |
| 33018 | PhCH2 |
| 33019 | Ph(CH2)2 |
| 33020 | Ph(CH2)3 |
| 33021 | PhO(CH2)2 |
| 33022 | PhCH2OCH2CH2 |
| 33023 | PhCH2O(C=O)CH2CH2 |
| 33024 | o-CH3Ph |
| 33025 | m-CH3Ph |
| 33026 | p-CH3Ph |
| 33027 | 2,4-(CH3)2Ph |

TABLE 33-continued
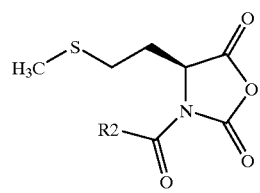
| Compound No. | R2 |
|---|---|
| 33028 | 3,5-(CH3)2Ph |
| 33029 | 2,4,6-(CH3)3Ph |
| 33030 | p-CH3OPh |
| 33031 | p-CH3CH2OPh |
| 33032 | p-CH3(CH2)2OPh |
| 33033 | p-FPh |
| 33034 | p-ClPh |
| 33035 | p-BrPh |
| 33036 | p-IPh |
| 33037 | p-PhOPh |
| 33038 | p-PhCH2OPh |
| 33039 | p-NO2Ph |
| 33040 | p-CNPh |
| 33041 | p-CH3SO2Ph |
| 33042 | 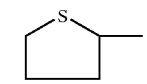 |
| 33043 | 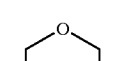 |
| 33044 | 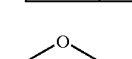 |
| 33045 | 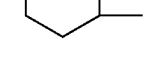 |
| 33046 | 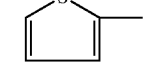 |
| 33047 | 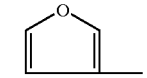 |
| 33048 | 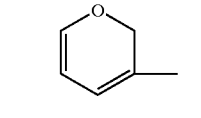 |
| 33049 | 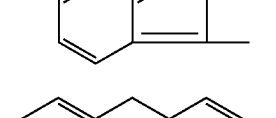 |
| 33050 | 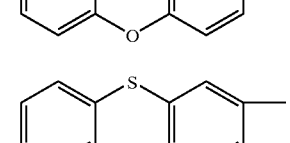 |
| 33051 | 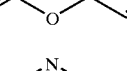 |
TABLE 33-continued
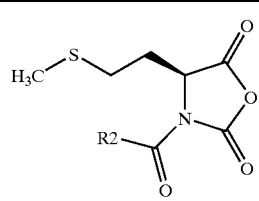
| Compound No. | R2 |
|---|---|
| 33052 | 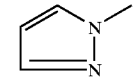 |
| 33053 | 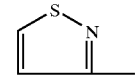 |
| 33054 | 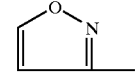 |
| 33055 | 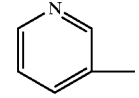 |
| 33056 | 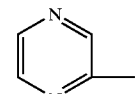 |
| 33057 | 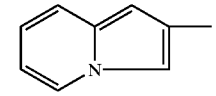 |
| 33058 | 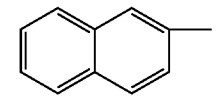 |
| 33059 | 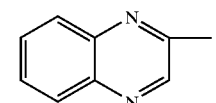 |
| 33060 | 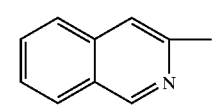 |
| 33061 | 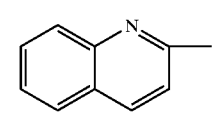 |
| 33062 |  |

TABLE 34
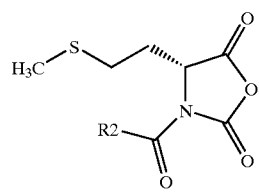
| Compound No. | R2 |
|---|---|
| 34001 | CH3 |
| 34002 | CH2CH3 |
| 34003 | (CH2)2CH3 |
| 34004 | CH(CH3)2 |
| 34005 | (CH2)3CH3 |
| 34006 | CH2CH(CH3)2 |
| 34007 | CH(CH3)CH2CH3 |
| 34008 | C(CH3)3 |
| 34009 | (CH2)4CH3 |
| 34010 | (CH2)5CH3 |
| 34011 | (CH2)6CH3 |
| 34012 | (CH2)7CH3 |
| 34013 | (CH2)8CH3 |
| 34014 | cyclopropyl |
| 34015 | cyclobutyl |
| 34016 | cyclohexyl |
| 34017 | Ph |
| 34018 | PhCH2 |
| 34019 | Ph(CH2)2 |
| 34020 | Ph(CH2)3 |
| 34021 | PhO(CH2)2 |
| 34022 | PhCH2OCH2CH2 |
| 34023 | PhCH2O(C=O)CH2CH2 |
| 34024 | o-CH3Ph |
| 34025 | m-CH3Ph |
| 34026 | p-CH3Ph |
| 34027 | 2,4-(CH3)2Ph |
| 34028 | 3,5-(CH3)2Ph |
| 34029 | 2,4,6-(CH3)3Ph |
| 34030 | p-CH3OPh |
| 34031 | p-CH3CH2OPh |
| 34032 | p-CH3(CH2)2OPh |
| 34033 | p-FPh |
| 34034 | p-ClPh |
| 34035 | p-BrPh |
| 34036 | p-IPh |
| 34037 | p-PhOPh |
| 34038 | p-PhCH2OPh |
| 34039 | p-NO2Ph |
| 34040 | p-CNPh |
| 34041 | p-CH3SO2Ph |
| 34042 | 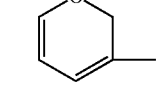 |
| 34043 | 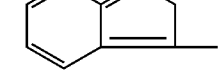 |
| 34044 | 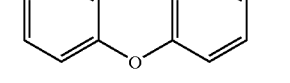 |
| 34045 | 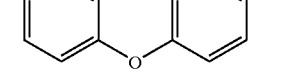 |
| 34046 | 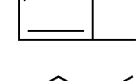 |
TABLE 34-continued
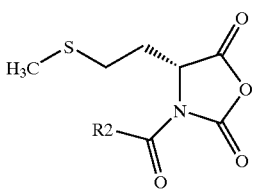
| Compound No. | R2 |
|---|---|
| 34047 | 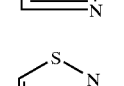 |
| 34048 | 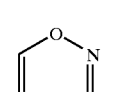 |
| 34049 | 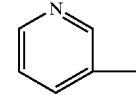 |
| 34050 | 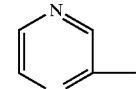 |
| 34051 | 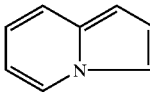 |
| 34052 | 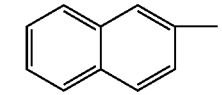 |
| 34053 |  |
| 34054 |  |
| 34055 |  |
| 34056 |  |
| 34057 |  |
| 34058 |  |

TABLE 34-continued
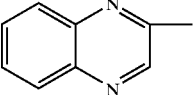
| Compound No. | R2 |
|---|---|
| 34059 | 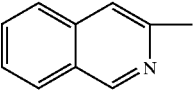 |
| 34060 | 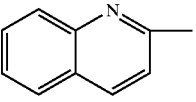 |
| 34061 |  |
| 34062 | 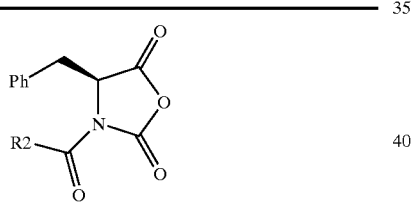 |
TABLE 35
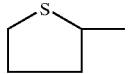
| Compound No. | R2 |
|---|---|
| 35001 | CH3 |
| 35002 | CH2CH3 |
| 35003 | (CH2)2CH3 |
| 35004 | CH(CH3)2 |
| 35005 | (CH2)3CH3 |
| 35006 | CH2CH(CH3)2 |
| 35007 | CH(CH3)CH2CH3 |
| 35008 | C(CH3)3 |
| 35009 | (CH2)4CH3 |
| 35010 | (CH2)5CH3 |
| 35011 | (CH2)6CH3 |
| 35012 | (CH2)7CH3 |
| 35013 | (CH2)8CH3 |
| 35014 | cyclopropyl |
| 35015 | cyclobutyl |
| 35016 | cyclohexyl |
| 35017 | Ph |
| 35018 | PhCH2 |
| 35019 | Ph(CH2)2 |
| 35020 | Ph(CH2)3 |
| 35021 | PhO(CH2)2 |
| 35022 | PhCH2OCH2CH2 |
| 35023 | PhCH2O(C=O)CH2CH2 |
| 35024 | o-CH3Ph |
| 35025 | m-CH3Ph |
| 35026 | p-CH3Ph |
| 35027 | 2,4-(CH3)2Ph |
TABLE 35-continued
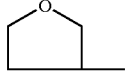
| Compound No. | R2 |
|---|---|
| 35028 | 3,5-(CH3)2Ph |
| 35029 | 2,4,6-(CH3)3Ph |
| 35030 | p-CH3OPh |
| 35031 | p-CH3CH2OPh |
| 35032 | p-CH3(CH2)2OPh |
| 35033 | p-FPh |
| 35034 | p-ClPh |
| 35035 | p-BrPh |
| 35036 | p-IPh |
| 35037 | p-PhOPh |
| 35038 | p-PhCH2OPh |
| 35039 | p-NO2Ph |
| 35040 | p-CNPh |
| 35041 | p-CH3SO2Ph |
| 35042 | 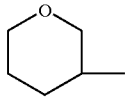 |
| 35043 | 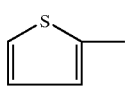 |
| 35044 | 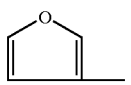 |
| 35045 | 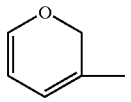 |
| 35046 | 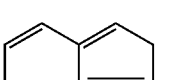 |
| 35047 | 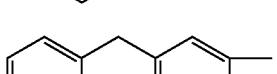 |
| 35048 | 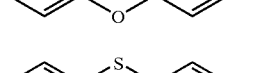 |
| 35049 | 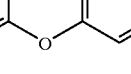 |
| 35050 |  |
| 35051 |  |

TABLE 35-continued
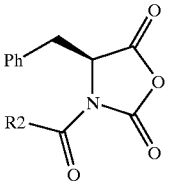
| Compound No. | R2 |
|---|---|
| 35052 | 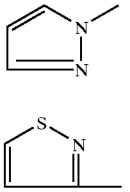 |
| 35053 | 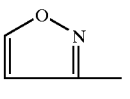 |
| 35054 | 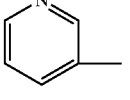 |
| 35055 | 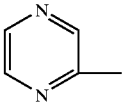 |
| 35056 | 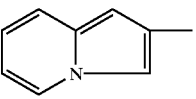 |
| 35057 | 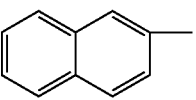 |
| 35058 | 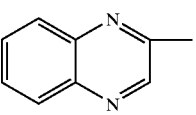 |
| 35059 | 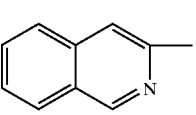 |
| 35060 | 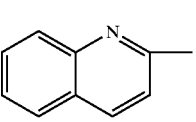 |
| 35061 |  |
| 35062 |  |
TABLE 36
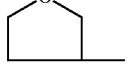
| Compound No. | R2 |
|---|---|
| 36001 | CH3 |
| 36002 | CH2CH3 |
| 36003 | (CH2)2CH3 |
| 36004 | CH(CH3)2 |
| 36005 | (CH2)3CH3 |
| 36006 | CH2CH(CH3)2 |
| 36007 | CH(CH3)CH2CH3 |
| 36008 | C(CH3)3 |
| 36009 | (CH2)4CH3 |
| 36010 | (CH2)5CH3 |
| 36011 | (CH2)6CH3 |
| 36012 | (CH2)7CH3 |
| 36013 | (CH2)8CH3 |
| 36014 | cyclopropyl |
| 36015 | cyclobutyl |
| 36016 | cyclohexyl |
| 36017 | Ph |
| 36018 | PhCH2 |
| 36019 | Ph(CH2)2 |
| 36020 | Ph(CH2)3 |
| 36021 | PhO(CH2)2 |
| 36022 | PhCH2OCH2CH2 |
| 36023 | PhCH2O(C=O)CH2CH2 |
| 36024 | o-CH3Ph |
| 36025 | m-CH3Ph |
| 36026 | p-CH3Ph |
| 36027 | 2,4-(CH3)2Ph |
| 36028 | 3,5-(CH3)2Ph |
| 36029 | 2,4,6-(CH3)3Ph |
| 36030 | p-CH3OPh |
| 36031 | p-CH3CH2OPh |
| 36032 | p-CH3(CH2)2OPh |
| 36033 | p-FPh |
| 36034 | p-ClPh |
| 36035 | p-BrPh |
| 36036 | p-IPh |
| 36037 | p-PhOPh |
| 36038 | p-PhCH2OPh |
| 36039 | p-NO2Ph |
| 36040 | p-CNPh |
| 36041 | p-CH3SO2Ph |
| 36042 | 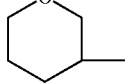 |
| 36043 | 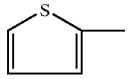 |
| 36044 | 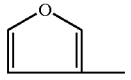 |
| 36045 |  |
| 36046 |  |

TABLE 36-continued

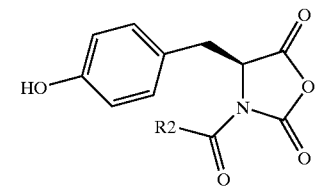

| Compound No. | R2 |
|---|---|
| 36047 | (oxine/pyran-3-yl) |
| 36048 | (indene-2-yl) |
| 36049 | (xanthene-2-yl) |
| 36050 | (phenoxathiine-2-yl) |
| 36051 | (oxazol-4-yl) |
| 36052 | (1-methylpyrazol-3-yl) |
| 36053 | (thiadiazol-yl) |
| 36054 | (isoxazol-3-yl) |
| 36055 | (pyridin-3-yl) |
| 36056 | (pyrazin-2-yl) |
| 36057 | (indolizin-2-yl) |
| 36058 | (naphthalen-2-yl) |

TABLE 36-continued

| Compound No. | R2 |
|---|---|
| 36059 | (quinoxalin-2-yl) |
| 36060 | (isoquinolin-3-yl) |
| 36061 | (quinolin-2-yl) |
| 36062 | (quinuclidinyl) |

TABLE 37

| Compound No. | R2 |
|---|---|
| 37001 | CH3 |
| 37002 | CH2CH3 |
| 37003 | (CH2)2CH3 |
| 37004 | CH(CH3)2 |
| 37005 | (CH2)3CH3 |
| 37006 | CH2CH(CH3)2 |
| 37007 | CH(CH3)CH2CH3 |
| 37008 | C(CH3)3 |
| 37009 | (CH2)4CH3 |
| 37010 | (CH2)5CH3 |
| 37011 | (CH2)6CH3 |
| 37012 | (CH2)7CH3 |
| 37013 | (CH2)8CH3 |
| 37014 | cyclopropyl |
| 37015 | cyclobutyl |
| 37016 | cyclohexyl |
| 37017 | Ph |
| 37018 | PhCH2 |
| 37019 | Ph(CH2)2 |
| 37020 | Ph(CH2)3 |
| 37021 | PhO(CH2)2 |
| 37022 | PhCH2OCH2CH2 |
| 37023 | PhCH2O(C=O)CH2CH2 |
| 37024 | o-CH3Ph |
| 37025 | m-CH3Ph |
| 37026 | p-CH3Ph |
| 37027 | 2,4-(CH3)2Ph |

TABLE 37-continued
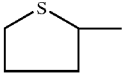
| Compound No. | R2 |
|---|---|
| 37028 | 3,5-(CH3)2Ph |
| 37029 | 2,4,6-(CH3)3Ph |
| 37030 | p-CH3OPh |
| 37031 | p-CH3CH2OPh |
| 37032 | p-CH3(CH2)2OPh |
| 37033 | p-FPh |
| 37034 | p-ClPh |
| 37035 | p-BrPh |
| 37036 | p-IPh |
| 37037 | p-PhOPh |
| 37038 | p-PhCH2OPh |
| 37039 | p-NO2Ph |
| 37040 | p-CNPh |
| 37041 | p-CH3SO2Ph |
| 37042 | 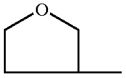 |
| 37043 | 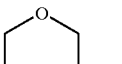 |
| 37044 | 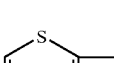 |
| 37045 | 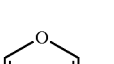 |
| 37046 | 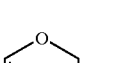 |
| 37047 | 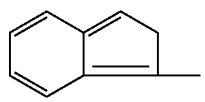 |
| 37048 | 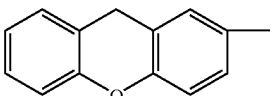 |
| 37049 | 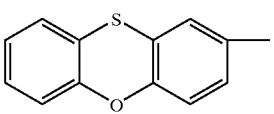 |
| 37050 | 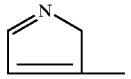 |
TABLE 37-continued
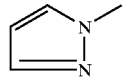
| Compound No. | R2 |
|---|---|
| 37051 | 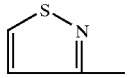 |
| 37052 | 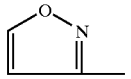 |
| 37053 | 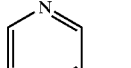 |
| 37054 | 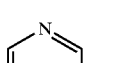 |
| 37055 | 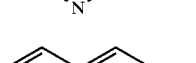 |
| 37056 | 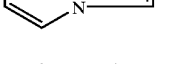 |
| 37057 | 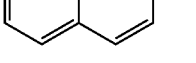 |
| 37058 | 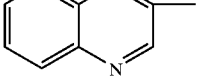 |
| 37059 | 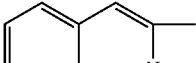 |
| 37060 |  |
| 37061 |  |
| 37062 |  |

TABLE 38
| Compound No. | R2 |
|---|---|
| 38001 | CH3 |
| 38002 | CH2CH3 |
| 38003 | (CH2)2CH3 |
| 38004 | CH(CH3)2 |
| 38005 | (CH2)3CH3 |
| 38006 | CH2CH(CH3)2 |
| 38007 | CH(CH3)CH2CH3 |
| 38008 | C(CH3)3 |
| 38009 | (CH2)4CH3 |
| 38010 | (CH2)5CH3 |
| 38011 | (CH2)6CH3 |
| 38012 | (CH2)7CH3 |
| 38013 | (CH2)8CH3 |
| 38014 | cyclopropyl |
| 38015 | cyclobutyl |
| 38016 | cyclohexyl |
| 38017 | Ph |
| 38018 | PhCH2 |
| 38019 | Ph(CH2)2 |
| 38020 | Ph(CH2)3 |
| 38021 | PhO(CH2)2 |
| 38022 | PhCH2OCH2CH2 |
| 38023 | PhCH2O(C=O)CH2CH2 |
| 38024 | o-CH3Ph |
| 38025 | m-CH3Ph |
| 38026 | p-CH3Ph |
| 38027 | 2,4-(CH3)2Ph |
| 38028 | 3,5-(CH3)2Ph |
| 38029 | 2,4,6-(CH3)3Ph |
| 38030 | p-CH3OPh |
| 38031 | p-CH3CH2OPh |
| 38032 | p-CH3(CH2)2OPh |
| 38033 | p-FPh |
| 38034 | p-ClPh |
| 38035 | p-BrPh |
| 38036 | p-IPh |
| 38037 | p-PhOPh |
| 38038 | p-PhCH2OPh |
| 38039 | p-NO2Ph |
| 38040 | p-CNPh |
| 38041 | p-CH3SO2Ph |
| 38042 | 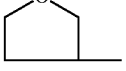 |
| 38043 | 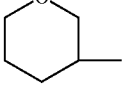 |
| 38044 | 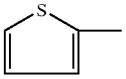 |
| 38045 | 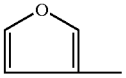 |
| 38046 | 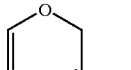 |
TABLE 38-continued
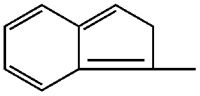
| Compound No. | R2 |
|---|---|
| 38047 | 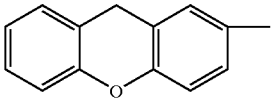 |
| 38048 | 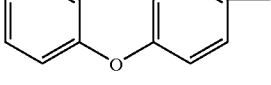 |
| 38049 |  |
| 38050 | 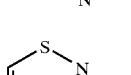 |
| 38051 | 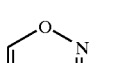 |
| 38052 | 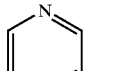 |
| 38053 | 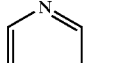 |
| 38054 | 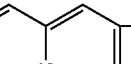 |
| 38055 | 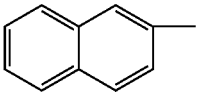 |
| 38056 |  |
| 38057 |  |
| 38058 |  |

TABLE 38-continued
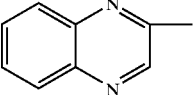
| Compound No. | R2 |
|---|---|
| 38059 | 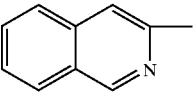 |
| 38060 | 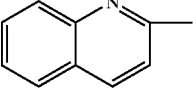 |
| 38061 |  |
| 38062 | 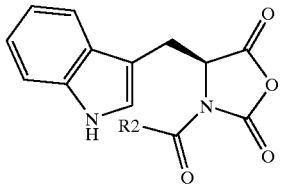 |
TABLE 39
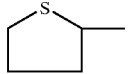
| Compound No. | R2 |
|---|---|
| 39001 | CH3 |
| 39002 | CH2CH3 |
| 39003 | (CH2)2CH3 |
| 39004 | CH(CH3)2 |
| 39005 | (CH2)3CH3 |
| 39006 | CH2CH(CH3)2 |
| 39007 | CH(CH3)CH2CH3 |
| 39008 | C(CH3)3 |
| 39009 | (CH2)4CH3 |
| 39010 | (CH2)5CH3 |
| 39011 | (CH2)6CH3 |
| 39012 | (CH2)7CH3 |
| 39013 | (CH2)8CH3 |
| 39014 | cyclopropyl |
| 39015 | cyclobutyl |
| 39016 | cyclohexyl |
| 39017 | Ph |
| 39018 | PhCH2 |
| 39019 | Ph(CH2)2 |
| 39020 | Ph(CH2)3 |
| 39021 | PhO(CH2)2 |
| 39022 | PhCH2OCH2CH2 |
| 39023 | PhCH2O(C=O)CH2CH2 |
| 39024 | o-CH3Ph |
| 39025 | m-CH3Ph |
| 39026 | p-CH3Ph |
| 39027 | 2,4-(CH3)2Ph |
TABLE 39-continued
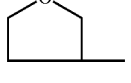
| Compound No. | R2 |
|---|---|
| 39028 | 3,5-(CH3)2Ph |
| 39029 | 2,4,6-(CH3)3Ph |
| 39030 | p-CH3OPh |
| 39031 | p-CH3CH2OPh |
| 39032 | p-CH3(CH2)2OPh |
| 39033 | p-FPh |
| 39034 | p-ClPh |
| 39035 | p-BrPh |
| 39036 | p-IPh |
| 39037 | p-PhOPh |
| 39038 | p-PhCH2OPh |
| 39039 | p-NO2Ph |
| 39040 | p-CNPh |
| 39041 | p-CH3SO2Ph |
| 39042 | 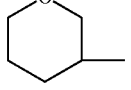 |
| 39043 | |
| 39044 | |
| 39045 | |
| 39046 | |
| 39047 | |
| 39048 |  |
| 39049 | |
| 39050 |  |

TABLE 39-continued
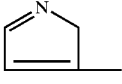
| Compound No. | R2 |
|---|---|
| 39051 | 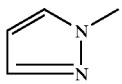 |
| 39052 | 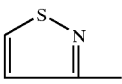 |
| 39053 | 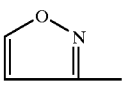 |
| 39054 | 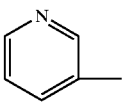 |
| 39055 | 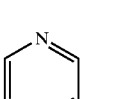 |
| 39056 | 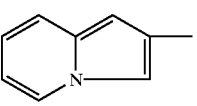 |
| 39057 | 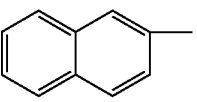 |
| 39058 | 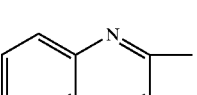 |
| 39059 | 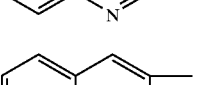 |
| 39060 | 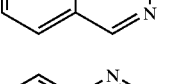 |
| 39061 |  |
| 39062 | 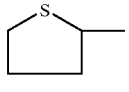 |
TABLE 40
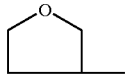
| Compound No. | R2 |
|---|---|
| 40001 | CH3 |
| 40002 | CH2CH3 |
| 40003 | (CH2)2CH3 |
| 40004 | CH(CH3)2 |
| 40005 | (CH2)3CH3 |
| 40006 | CH2CH(CH3)2 |
| 40007 | CH(CH3)CH2CH3 |
| 40008 | C(CH3)3 |
| 40009 | (CH2)4CH3 |
| 40010 | (CH2)5CH3 |
| 40011 | (CH2)6CH3 |
| 40012 | (CH2)7CH3 |
| 40013 | (CH2)8CH3 |
| 40014 | cyclopropyl |
| 40015 | cyclobutyl |
| 40016 | cyclohexyl |
| 40017 | Ph |
| 40018 | PhCH2 |
| 40019 | Ph(CH2)2 |
| 40020 | Ph(CH2)3 |
| 40021 | PhO(CH2)2 |
| 40022 | PhCH2OCH2CH2 |
| 40023 | PhCH2O(C=O)CH2CH2 |
| 40024 | o-CH3Ph |
| 40025 | m-CH3Ph |
| 40026 | p-CH3Ph |
| 40027 | 2,4-(CH3)2Ph |
| 40028 | 3,5-(CH3)2Ph |
| 40029 | 2,4,6-(CH3)3Ph |
| 40030 | p-CH3OPh |
| 40031 | p-CH3CH2OPh |
| 40032 | p-CH3(CH2)2OPh |
| 40033 | p-FPh |
| 40034 | p-ClPh |
| 40035 | p-BrPh |
| 40036 | p-IPh |
| 40037 | p-PhOPh |
| 40038 | p-PhCH2OPh |
| 40039 | p-NO2Ph |
| 40040 | p-CNPh |
| 40041 | p-CH3SO2Ph |
| 40042 | 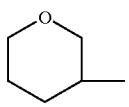 |
| 40043 | 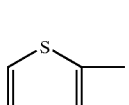 |
| 40044 |  |
| 40045 |  |

TABLE 40-continued

| Compound No. | R2 |
|---|---|
| 40046 | isoxazol-3-yl |
| 40047 | 2H-pyran-3-yl |
| 40048 | 1H-inden-2-yl |
| 40049 | 9H-xanthen-2-yl |
| 40050 | phenoxathiin-2-yl |
| 40051 | 2H-pyrrol-3-yl |
| 40052 | 1-methyl-1H-pyrazol-5-yl |
| 40053 | isothiazol-3-yl |
| 40054 | isoxazol-4-yl |
| 40055 | pyridin-3-yl |
| 40056 | pyrazin-2-yl |
| 40057 | indolizin-2-yl |
| 40058 | naphthalen-2-yl |
| 40059 | quinoxalin-2-yl |
| 40060 | isoquinolin-3-yl |
| 40061 | quinolin-2-yl |
| 40062 | 1-azabicyclo[2.2.1]heptyl |

TABLE 41
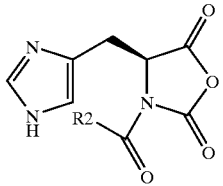
| Compound No. | R2 | Compound No. | R2 |
| --- | --- | --- | --- |
| 41001 | CH3 | 41045 | 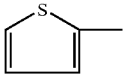 |
| 41002 | CH2CH3 | 41046 | 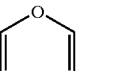 |
| 41003 | (CH2)2CH3 | 41047 | 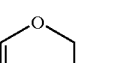 |
| 41004 | CH(CH3)2 | 41048 | 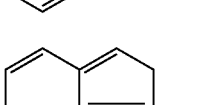 |
| 41005 | (CH2)3CH3 | 41049 | 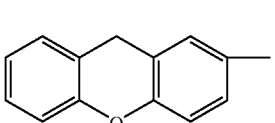 |
| 41006 | CH2CH(CH3)2 | 41050 | 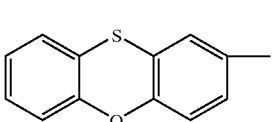 |
| 41007 | CH(CH3)CH2CH3 | 41051 | 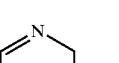 |
| 41008 | C(CH3)3 | 41052 | 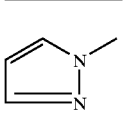 |
| 41009 | (CH2)4CH3 | 41053 | 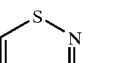 |
| 41010 | (CH2)5CH3 | 41054 | 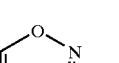 |
| 41011 | (CH2)6CH3 | 41055 | 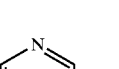 |
| 41012 | (CH2)7CH3 | 41056 | 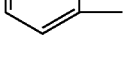 |

TABLE 41-continued
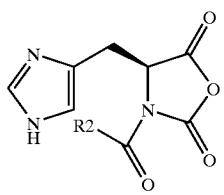
| Compound No. | R2 | Compound No. | R2 |
|---|---|---|---|
| 41013 | (CH2)8CH3 | 41057 | (indolizine) |
| 41014 | cyclopropyl | 41058 | (naphthalene) |
| 41015 | cyclobutyl | 41059 | (quinoxaline) |
| 41016 | cyclohexyl | 41060 | (isoquinoline) |
| 41017 | Ph | 41061 | (quinoline) |
| 41018 | PhCH2 | 41062 | (quinuclidine) |
| 41019 | Ph(CH2)2 | | |
| 41020 | Ph(CH2)3 | | |
| 41021 | PhO(CH2)2 | | |
| 41022 | PhCH2OCH2CH2 | | |
| 41023 | PhCH2O(C=O)CH2CH2 | | |
| 41024 | o-CH3Ph | | |
| 41025 | m-CH3Ph | | |
| 41026 | p-CH3Ph | | |
| 41027 | 2,4-(CH3)2Ph | | |
| 41028 | 3,5-(CH3)2Ph | | |
| 41029 | 2,4,6(CH3)3Ph | | |
| 41030 | p-CH3OPh | | |
| 41031 | p-CH3CH2OPh | | |
| 41032 | p-CH3(CH2)2OPh | | |
| 41033 | p-FPh | | |
| 41034 | p-ClPh | | |

TABLE 41-continued

| Compound No. | R2 | Compound No. | R2 |
|---|---|---|---|
| 41035 | p-BrPh | | |
| 41036 | p-IPh | | |
| 41037 | p-PhOPh | | |
| 41038 | p-PhCH2OPh | | |
| 41039 | p-NO2Ph | | |
| 41040 | p-CNPh | | |
| 41041 | p-CH3SO2Ph | | |
| 41042 | 2-tetrahydrothienyl | | |
| 41043 | 2-tetrahydrofuryl | | |
| 41044 | 3-tetrahydropyranyl | | |

TABLE 42

| Compound No. | R2 | Compound No. | R2 |
|---|---|---|---|
| 42001 | CH3 | 42045 | 2-thienyl |
| 42002 | CH2CH3 | 42046 | 2-furyl |
| 42003 | (CH2)2CH3 | 42047 | 3,4-dihydro-2H-pyran-3-yl |
| 42004 | CH(CH3)2 | 42048 | indenyl |

TABLE 42-continued

| Compound No. | R2 | Compound No. | R2 |
|---|---|---|---|
| 42005 | (CH2)3CH3 | 42049 | xanthene-2-yl |
| 42006 | CH2CH(CH3)2 | 42050 | phenoxathiin-2-yl |
| 42007 | CH(CH3)CH2CH3 | 42051 | pyrrol-2-yl |
| 42008 | C(CH3)3 | 42052 | 1-methylpyrazol-3-yl |
| 42009 | (CH2)4CH3 | 42053 | isothiazol-3-yl |
| 42010 | (CH2)5CH3 | 42054 | isoxazol-3-yl |
| 42011 | (CH2)6CH3 | 42055 | pyridin-3-yl |
| 42012 | (CH2)7CH3 | 42056 | pyrazin-2-yl |
| 42013 | (CH2)8CH3 | 42057 | indolizin-2-yl |
| 42014 | cyclopropyl | 42058 | naphthalen-2-yl |
| 42015 | cyclobutyl | 42059 | quinoxalin-2-yl |
| 42016 | cyclohexyl | 42060 | isoquinolin-3-yl |

TABLE 42-continued
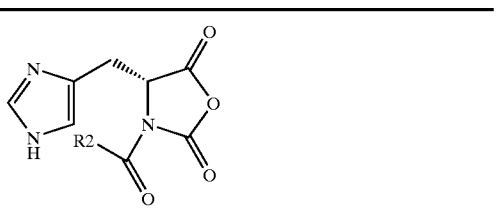
| Compound No. | R2 | Compound No. | R2 |
|---|---|---|---|
| 42017 | Ph | 42061 | 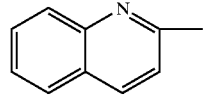 |
| 42018 | PhCH2 | 42062 |  |
| 42019 | Ph(CH2)2 | | |
| 42020 | Ph(CH2)3 | | |
| 42021 | PhO(CH2)2 | | |
| 42022 | PhCH2OCH2CH2 | | |
| 42023 | PhCH2O(C=O)CH2CH2 | | |
| 42024 | o-CH3Ph | | |
| 42025 | m-CH3Ph | | |
| 42026 | p-CH3Ph | | |
| 42027 | 2,4-(CH3)2Ph | | |
| 42028 | 3,5-(CH3)2Ph | | |
| 42029 | 2,4,6(CH3)3Ph | | |
| 42030 | p-CH3OPh | | |
| 42031 | p-CH3CH2OPh | | |
| 42032 | p-CH3(CH2)2OPh | | |
| 42033 | p-FPh | | |
| 42034 | p-ClPh | | |
| 42035 | p-BrPh | | |
| 42036 | p-IPh | | |
| 42037 | p-PhOPh | | |
| 42038 | p-PhCH2OPh | | |
| 42039 | p-NO2Ph | | |
| 42040 | p-CNPh | | |
| 42041 | p-CH3SO2Ph | | |
| 42042 | 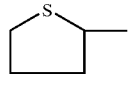 | | |
| 42043 | 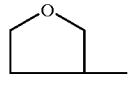 | | |

TABLE 42-continued
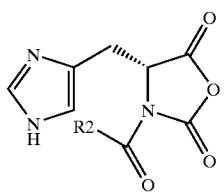
| Compound No. | R2 | Compound No. | R2 |
|---|---|---|---|
| 42044 | 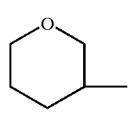 | | |
TABLE 43
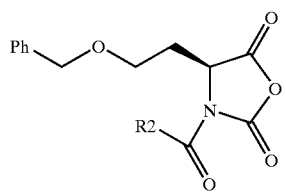
| Compound No. | R2 | Compound No. | R2 |
|---|---|---|---|
| 43001 | CH3 | 43045 |  |
| 43002 | CH2CH3 | 43046 | 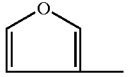 |
| 43003 | (CH2)2CH3 | 43047 | 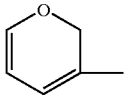 |
| 43004 | CH(CH3)2 | 43048 | 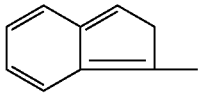 |
| 43005 | (CH2)3CH3 | 43049 | 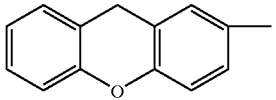 |
| 43006 | CH2CH(CH3)2 | 43050 | 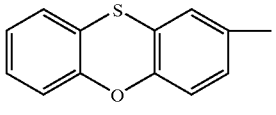 |
| 43007 | CH(CH3)CH2CH3 | 43051 |  |
| 43008 | C(CH3)3 | 43052 | 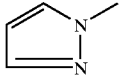 |

TABLE 43-continued
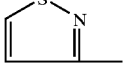
| Compound No. | R2 | Compound No. | R2 |
|---|---|---|---|
| 43009 | (CH2)4CH3 | 43053 | 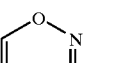 |
| 43010 | (CH2)5CH3 | 43054 | 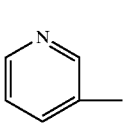 |
| 43011 | (CH2)6CH3 | 43055 | 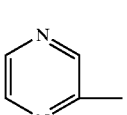 |
| 43012 | (CH2)7CH3 | 43056 | 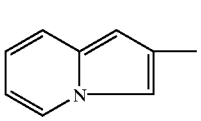 |
| 43013 | (CH2)8CH3 | 43057 | 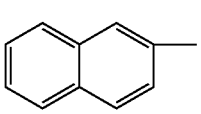 |
| 43014 | cyclopropyl | 43058 | 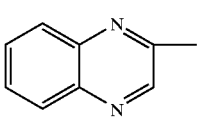 |
| 43015 | cyclobutyl | 43059 | 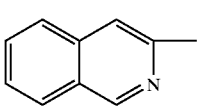 |
| 43016 | cyclohexyl | 43060 | 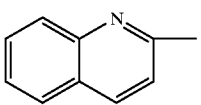 |
| 43017 | Ph | 43061 | 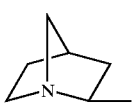 |
| 43018 | PhCH2 | 43062 |  |
| 43019 | Ph(CH2)2 | | |
| 43020 | Ph(CH2)3 | | |
| 43021 | PhO(CH2)2 | | |
| 43022 | PhCH2OCH2CH2 | | |
| 43023 | PhCH2O(C=O)CH2CH2 | | |

TABLE 43-continued
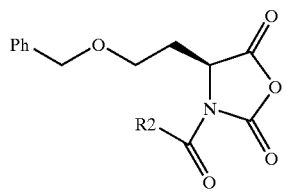
| Compound No. | R2 | Compound No. | R2 |
|---|---|---|---|
| 43024 | o-CH3Ph | | |
| 43025 | m-CH3Ph | | |
| 43026 | p-CH3Ph | | |
| 43027 | 2,4-(CH3)2Ph | | |
| 43028 | 3,5-(CH3)2Ph | | |
| 43029 | 2,4,6(CH3)3Ph | | |
| 43030 | p-CH3OPh | | |
| 43031 | p-CH3CH2OPh | | |
| 43032 | p-CH3(CH2)2OPh | | |
| 43033 | p-FPh | | |
| 43034 | p-ClPh | | |
| 43035 | p-BrPh | | |
| 43036 | p-IPh | | |
| 43037 | p-PhOPh | | |
| 43038 | p-PhCH2OPh | | |
| 43039 | p-NO2Ph | | |
| 43040 | p-CNPh | | |
| 43041 | p-CH3SO2Ph | | |
| 43042 | 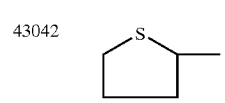 | | |
| 43043 | 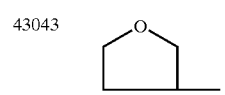 | | |
| 43044 | 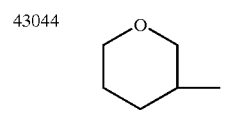 | | |

TABLE 44

| Compound No. | R2 | Compound No. | R2 |
|---|---|---|---|
| 44001 | CH3 | 44045 | 2-thienyl |
| 44002 | CH2CH3 | 44046 | 2-furyl |
| 44003 | (CH2)2CH3 | 44047 | 2H-pyran-3-yl |
| 44004 | CH(CH3)2 | 44048 | 1H-indene-2-yl |
| 44005 | (CH2)3CH3 | 44049 | 9H-xanthen-2-yl |
| 44006 | CH2CH(CH3)2 | 44050 | phenoxathiin-2-yl |
| 44007 | CH(CH3)CH2CH3 | 44051 | 2H-pyrrol-3-yl |
| 44008 | C(CH3)3 | 44052 | 1-methyl-1H-pyrazol-yl |
| 44009 | (CH2)4CH3 | 44053 | isothiazol-yl |
| 44010 | (CH2)5CH3 | 44054 | isoxazol-yl |
| 44011 | (CH2)6CH3 | 44055 | pyridin-3-yl |
| 44012 | (CH2)7CH3 | 44056 | pyrazin-2-yl |

TABLE 44-continued
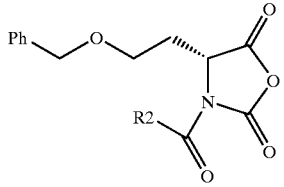
| Compound No. | R2 | Compound No. | R2 |
|---|---|---|---|
| 44013 | (CH2)8CH3 | 44057 | 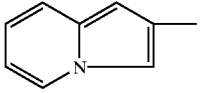 |
| 44014 | cyclopropyl | 44058 | 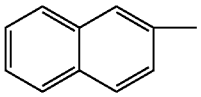 |
| 44015 | cyclobutyl | 44059 | 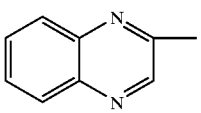 |
| 44016 | cyclohexyl | 44060 | 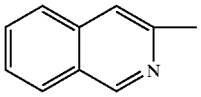 |
| 44017 | Ph | 44061 | 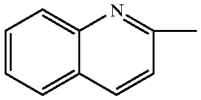 |
| 44018 | PhCH2 | 44062 | 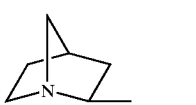 |
| 44019 | Ph(CH2)2 | | |
| 44020 | Ph(CH2)3 | | |
| 44021 | PhO(CH2)2 | | |
| 44022 | PhCH2OCH2CH2 | | |
| 44023 | PhCH2O(C=O)CH2CH2 | | |
| 44024 | o-CH3Ph | | |
| 44025 | m-CH3Ph | | |
| 44026 | p-CH3Ph | | |
| 44027 | 2,4-(CH3)2Ph | | |
| 44028 | 3,5-(CH3)2Ph | | |
| 44029 | 2,4,6(CH3)3Ph | | |
| 44030 | p-CH3OPh | | |
| 44031 | p-CH3CH2OPh | | |
| 44032 | p-CH3(CH2)2OPh | | |
| 44033 | p-FPh | | |
| 44034 | p-ClPh | | |

TABLE 44-continued

Structure: oxazolidine-2,5-dione with PhCH2OCH2CH2- substituent at the 4-position (S-configuration) and R2-C(=O)- group on N

| Compound No. | R2 | Compound No. | R2 |
|---|---|---|---|
| 44035 | p-BrPh | | |
| 44036 | p-IPh | | |
| 44037 | p-PhOPh | | |
| 44038 | p-PhCH2OPh | | |
| 44039 | p-NO2Ph | | |
| 44040 | p-CNPh | | |
| 44041 | p-CH3SO2Ph | | |
| 44042 | 2-tetrahydrothienyl | | |
| 44043 | 2-tetrahydrofuryl | | |
| 44044 | 3-tetrahydropyranyl | | |

TABLE 45

Structure: oxazolidine-2,5-dione with BocNH-(CH2)3- substituent at the 4-position and R2-C(=O)- group on N

| Compound No. | R2 | Compound No. | R2 |
|---|---|---|---|
| 45001 | CH3 | 45045 | 2-thienyl |
| 45002 | CH2CH3 | 45046 | 2-furyl |
| 45003 | (CH2)2CH3 | 45047 | 2H-pyran-3-yl |
| 45004 | CH(CH3)2 | 45048 | indenyl |

TABLE 45-continued
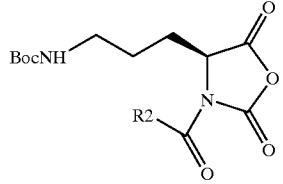
| Compound No. | R2 | Compound No. | R2 |
|---|---|---|---|
| 45005 | (CH2)3CH3 | 45049 | 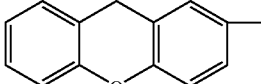 |
| 45006 | CH2CH(CH3)2 | 45050 | 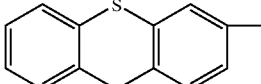 |
| 45007 | CH(CH3)CH2CH3 | 45051 |  |
| 45008 | C(CH3)3 | 45052 | 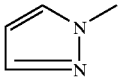 |
| 45009 | (CH2)4CH3 | 45053 | 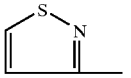 |
| 45010 | (CH2)5CH3 | 45054 | 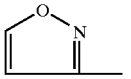 |
| 45011 | (CH2)6CH3 | 45055 | 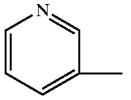 |
| 45012 | (CH2)7CH3 | 45056 | 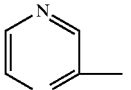 |
| 45013 | (CH2)8CH3 | 45057 | 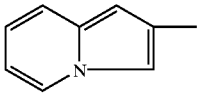 |
| 45014 | cyclopropyl | 45058 | 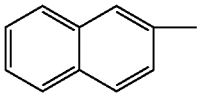 |
| 45015 | cyclobutyl | 45059 | 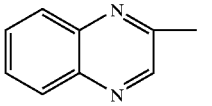 |
| 45016 | cyclohexyl | 45060 | 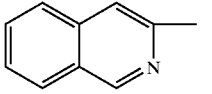 |

TABLE 45-continued

[Structure: BocNH-(CH2)3-C(H)(N-oxazolidine-2,5-dione)-C(=O)R2, where the N of the oxazolidinedione is acylated with R2-C(=O)-]

| Compound No. | R2 | Compound No. | R2 |
|---|---|---|---|
| 45017 | Ph | 45061 | 2-methylquinolinyl |
| 45018 | PhCH2 | 45062 | 1-azabicyclo[2.2.1]heptyl |
| 45019 | Ph(CH2)2 | | |
| 45020 | Ph(CH2)3 | | |
| 45021 | PhO(CH2)2 | | |
| 45022 | PhCH2OCH2CH2 | | |
| 45023 | PhCH2O(C=O)CH2CH2 | | |
| 45024 | o-CH3Ph | | |
| 45025 | m-CH3Ph | | |
| 45026 | p-CH3Ph | | |
| 45027 | 2,4-(CH3)2Ph | | |
| 45028 | 3,5-(CH3)2Ph | | |
| 45029 | 2,4,6(CH3)3Ph | | |
| 45030 | p-CH3OPh | | |
| 45031 | p-CH3CH2OPh | | |
| 45032 | p-CH3(CH2)2OPh | | |
| 45033 | p-FPh | | |
| 45034 | p-ClPh | | |
| 45035 | p-BrPh | | |
| 45036 | p-IPh | | |
| 45037 | p-PhOPh | | |
| 45038 | p-PhCH2OPh | | |
| 45039 | p-NO2Ph | | |
| 45040 | p-CNPh | | |
| 45041 | p-CH3SO2Ph | | |
| 45042 | tetrahydrothiophen-2-yl | | |
| 45043 | tetrahydrofuran-2-yl | | |

TABLE 45-continued
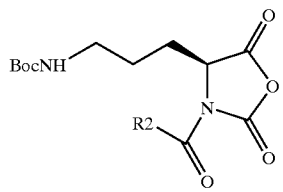
| Compound No. | R2 | Compound No. | R2 |
|---|---|---|---|
| 45044 | 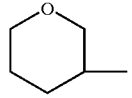 | | |
TABLE 46
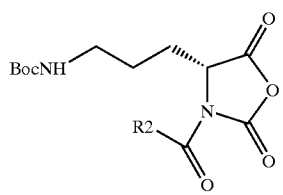
| Compound No. | R2 | Compound No. | R2 |
|---|---|---|---|
| 46001 | CH3 | 46045 |  |
| 46002 | CH2CH3 | 46046 | 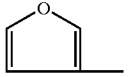 |
| 46003 | (CH2)2CH3 | 46047 | 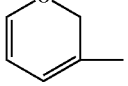 |
| 46004 | CH(CH3)2 | 46048 | 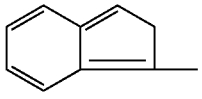 |
| 46005 | (CH2)3CH3 | 46049 | 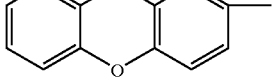 |
| 46006 | CH2CH(CH3)2 | 46050 | 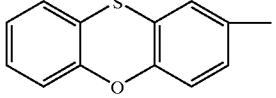 |
| 46007 | CH(CH3)CH2CH3 | 46051 |  |
| 46008 | C(CH3)3 | 46052 | 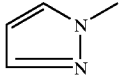 |

TABLE 46-continued

[Structure: BocNH-(CH2)3-CH attached to oxazolidine-2,5-dione ring with N-C(=O)-R2 substituent]

| Compound No. | R2 | Compound No. | R2 |
|---|---|---|---|
| 46009 | (CH2)4CH3 | 46053 | isothiazolyl |
| 46010 | (CH2)5CH3 | 46054 | isoxazolyl |
| 46011 | (CH2)6CH3 | 46055 | pyridin-3-yl |
| 46012 | (CH2)7CH3 | 46056 | pyrazin-2-yl |
| 46013 | (CH2)8CH3 | 46057 | indolizin-2-yl |
| 46014 | cyclopropyl | 46058 | naphthalen-2-yl |
| 46015 | cyclobutyl | 46059 | quinoxalin-2-yl |
| 46016 | cyclohexyl | 46060 | isoquinolin-3-yl |
| 46017 | Ph | 46061 | quinolin-2-yl |
| 46018 | PhCH2 | 46062 | 1-azabicyclo[2.2.1]heptanyl |
| 46019 | Ph(CH2)2 | | |
| 46020 | Ph(CH2)3 | | |
| 46021 | PhO(CH2)2 | | |
| 46022 | PhCH2OCH2CH2 | | |
| 46023 | PhCH2O(C=O)CH2CH2 | | |

TABLE 46-continued

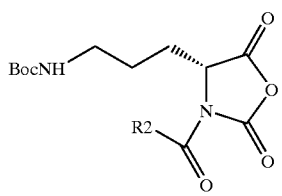

| Compound No. | R2 | Compound No. | R2 |
|---|---|---|---|
| 46024 | o-CH3Ph | | |
| 46025 | m-CH3Ph | | |
| 46026 | p-CH3Ph | | |
| 46027 | 2,4-(CH3)2Ph | | |
| 46028 | 3,5-(CH3)2Ph | | |
| 46029 | 2,4,6(CH3)3Ph | | |
| 46030 | p-CH3OPh | | |
| 46031 | p-CH3CH2OPh | | |
| 46032 | p-CH3(CH2)2OPh | | |
| 46033 | p-FPh | | |
| 46034 | p-ClPh | | |
| 46035 | p-BrPh | | |
| 46036 | p-IPh | | |
| 46037 | p-PhOPh | | |
| 46038 | p-PhCH2OPh | | |
| 46039 | p-NO2Ph | | |
| 46040 | p-CNPh | | |
| 46041 | p-CH3SO2Ph | | |
| 46042 | (2-thiolanyl) | | |
| 46043 | (2-tetrahydrofuryl) | | |
| 46044 | (3-tetrahydropyranyl) | | |

The compound numbers described in the above tables correspond to the compound numbers to be described in Examples.

A description will hereinafter be made about certain representative production processes according to the present invention.

[Production process of an amino acid N-carboxyanhydride with a substituent on a nitrogen atom thereof, which is represented by the formula (1)]

The compound represented by the formula (1) can be produced by reacting an amino acid N-carboxyanhydride, which is represented by the formula (4), with a compound of the formula (5) or (6).

Incidentally, the amino acid N-carboxyanhydride represented by the formula (4), which is used as a raw material in the production of the invention compound represented by the formula (1), can be produced by reacting the corresponding available amino acid with phosgene or by causing phosphorus trichloride, thionyl chloride or the like on an amino acid with a nitrogen atom thereof protected by urethane.

Further, the compound represented by the formula (5) or (6) is readily available from the market or by synthesis in a known manner.

The reaction temperature may range from −78 to 200° C., preferably from −50 to 50° C. The reaction time, on the other hand, may range from several minutes to 72 hours, preferably from several minutes to 24 hours.

[Production process of an amide derivative represented by the formula (8)]

The amidation reaction according to the present invention can be practiced by dissolving an N-substituted NCA in an inert diluent (for example, ethyl acetate) and then cooling the resulting solution under stirring. As an alternative, the reaction can be conducted in the absence of an inert diluent. Next, a solution of a desired amine (including a protected or unprotected amino acid) in an inert solvent (for example, ethyl acetate) is charged dropwise. This charging of the amine into a reaction system may also be conducted in the absence of an inert diluent. To the mixture so obtained, a base (for example, N-methylmorpholine, 4-dimethylaminopyridine or the like) is added. The base can promote a condensation reaction and can eliminate carbonic acid produced during the reaction, although it is not absolutely necessary to add the base.

Per mole of the N-substituted NCA, the desired amine may be used in an amount of from 1 to 20 equivalents, preferably from 1 to 5 equivalents, and the base, when to be added, may be used in an amount of from 0.1 to 20 equivalents, preferably from 0.1 to 5 equivalents.

When the inert diluent is used, the concentration of the N-substituted NCA may range from 0.01 to 50 mol/L, with a range of from 0.05 to 20 mol/L being preferred.

The reaction temperature may range from −78 to 200° C., preferably from −50 to 50° C. The reaction time, on the other hand, may range from several minutes to 72 hours, preferably from several minutes to 24 hours.

The amide derivative so completed can be purified by washing it with an aqueous acidic solution (for example, an aqueous solution of hydrochloric acid or an aqueous solution of potassium hydrogensulfate) to remove the unreacted amine, by washing it with an aqueous alkaline solution (for example, an aqueous solution of sodium hydroxide or an aqueous solution of sodium hydrogencarbonate) to eliminate byproducts formed by decomposition or the like, or by an operation such as recrystallization making use of an appropriate solvent. The amide derivative obtained by this purification is extremely uniform, and practically requires no further purification. As the concurrent formation of byproducts is very limited, the amide derivative is formed with extremely high yield and its purification is easy.

A description will next be described about racemization of an amino acid N-carboxyanhydride with a substituent of the acyl type on a nitrogen atom thereof as described herein. This compound can be readily converted into its corresponding diastereomer compound (diamide compound) by conducting a reaction with an optically active compound. It is possible to confirm racemization of the resulting diastereomer compound, because the surplus rate of the diastereomer can be easily determined by analyzing the compound, for example, by high-performance liquid chromatography, nuclear magnetic resonance spectroscopy or the like. The compounds and production processes described herein have been ascertained to be free of the problem of racemization because each of the compounds can be obtained in the form of a single diastereomer compound (diamide compound) alone by conducting the reaction under appropriate conditions.

Incidentally, the amine substituted by $R^3$ and $R^4$, which is represented by the formula (7) and is used as a raw material in the production of the invention compound represented by the formula (8), is readily available from the market or by synthesis in a known manner.

EXAMPLES

Examples and Referential Examples of the present invention will hereinafter be described. It should, however, be borne in mind that the present invention is by no means limited by them.

Example 1

Synthesis of (S)-3-benzoyl-4-methyl-2,5-oxazolidinedione (L-N-benzoylalaline-NCA) (Compound No. 1017)

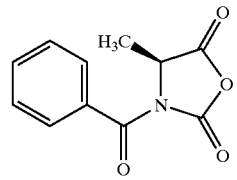

(1017)

(S)-4-Methyl-2,5-oxazolidinedione (L-alanine-NCA) (230 mg, 2.0 mmol) was dissolved in ethyl acetate (23 mL), followed by the addition of benzoyl chloride (365 mg, 2.6 mmol) under ice cooling. Further, a solution of 4-dimethylaminopyridine (318 mg, 2.6 mmol) in ethyl acetate (11 mL) was added dropwise under ice cooling over 20 minutes. After the resulting mixture was stirred as was at 0° C. for 3 hours, a precipitated salt was filtered off, and the filtrate was concentrated under reduced pressure. The concentration residue was re-dissolved in a mixed solvent consisting of ethyl acetate (5 mL) and hexane (5 mL), and insoluble matter was filtered off. The filtrate was concentrated under reduced pressure to afford the title compound as white crystals (351 mg, 80%).

Melting point: 104.2–105.1° C.(dec.)

$^1$H-N.M.R.(CDCl$_3$, 400 MHz) δ 1.74(3H, d, J=6.8 Hz), 5.13(1H, q, J=6.8 Hz), 7.44–7.54(2H, m), 7.61–7.65(1H, m), 7.72–7.75(2H, m).

IR(KBr)νmax 3379, 3074, 2991, 1865, 1822, 1698 cm$^{-1}$

Example 2

Synthesis of (S)-3-benzoyl-4-methyl-2,5-oxazolidinedione (L-N-benzoylalaline-NCA) (Compound No. 1017)

4-Dimethylaminopyridine (61 mg, 0.5 mmol) and N-methylmorpholine (152 mg, 1.5 mmol) were dissolved in ethyl acetate (15 mL), followed by the addition of (S)-4-methyl-2,5-oxazolidinedione (L-alanine-NCA) (230 mg, 2.0 mmol) under ice cooling. Further, a solution of benzoyl chloride (281 mg, 2.0 mmol) in ethyl acetate (7 mL) was added dropwise under ice cooling over 20 minutes. After the resulting mixture was stirred as was at 0° C. for 2 hours, a precipitated salt was filtered off, and the filtrate was concentrated under reduced pressure. The concentration residue was re-dissolved in a mixed solvent consisting of ethyl acetate (5 mL) and hexane (5 mL), and insoluble matter was filtered off. The filtrate was concentrated under reduced pressure to afford the title compound as white crystals (324 mg, 74%).

Example 3

Synthesis of (S)-3-benzoyl-4-isopropyl-2,5-oxazolidinedione (L-N-benzoylvaline-NCA)

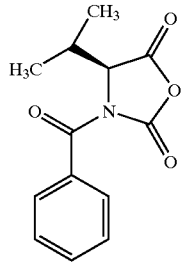

(3017)

Benzoyl chloride (295 mg, 2.1 mmol) was dissolved in ethyl acetate (21 mL), followed by the addition of (S)-4-isopropyl-2,5-oxazolidinedione (L-valine-NCA) (286 mg, 2.0 mmol) under ice cooling. Further, a solution of 4-dimethylaminopyridine (257 mg, 2.1 mmol) in ethyl acetate (11 mL) was added dropwise under ice cooling over 20 minutes. The resulting mixture was allowed to rise as was in temperature from 09. After the mixture was stirred at room temperature for 2 hours, a precipitated salt was filtered off, and the filtrate was concentrated under reduced pressure. The concentration residue was re-dissolved in a mixed solvent consisting of ethyl acetate (5 mL) and hexane (5 mL), and insoluble matter was filtered off. The filtrate was concentrated under reduced pressure to afford the title compound as white crystals (351 mg, 80%).

Melting point: 124.8–125.9° C. (dec.)

$^1$H-N.M.R.(CDCl$_3$, 400 MHz) δ 1.09(3H, d, J=6.8 Hz), 1.26(3H, d, J=7.1 Hz), 2.51(1H, m), 5.09(1H, d, J=3.7 Hz), 7.47–7.52(2H, m), 7.62–7.66(1H, m), 7.74–7.77(2H, m).

IR(KBr)νmax 2969, 2937, 2879, 1862, 1816, 1694 cm$^{-1}$

Example 4

Synthesis of (S)-3-benzoyl-4-tert-butyl-2,5-oxazolidinedione (L-N-benzoyl-tert-leucine-NCA) (Compound No. 9017)

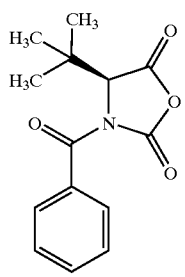

(9017)

In a similar manner as in Example 3, the title compound was obtained as white crystals (341 mg, 65%) by using benzoyl chloride (295 mg, 2.1 mmol), (S)-4-tert-butyl-2,5-oxazolidinedione (L-tert-leucine-NCA)(314 mg, 2.0 mmol), 4-dimethylaminopyridine (257 mg, 2.1 mmol) and ethyl acetate (32 mL).

Melting point: 127.8–128.9° C.(dec.)

$^1$H-N.M.R.(CDCl$_3$, 400 MHz) δ 1.15(9H, s), 5.10(1H, s), 7.52(2H, t, J=8.1 Hz), 7.67(1H, t, J=7.3 Hz), 7.86(2H, dd, J=1.2, 8.3 Hz).

IR(KBr)νmax 2983, 2963, 2876, 1860, 1808, 1704 cm$^{-1}$

Example 5

Synthesis of (S)-3-benzoyl-4-phenyl-2,5-oxazolidinedione (L-N-benzoylphenylalanine-NCA) (Compound No. 35017)

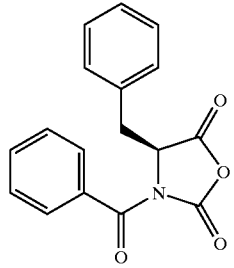

(35017)

In a similar manner as in Example 3, the title compound was obtained as white crystals (476 mg, 81%) by using benzoyl chloride (295 mg, 2.1 mmol), (S)-4-phenyl-2,5-oxazolidinedione (L-phenylalanine-NCA)(382 mg, 2.0 mmol), 4-dimethylaminopyridine (257 mg, 2.1 mmol) and ethyl acetate (32 mL).

Melting point: 125.8–126.4° C. (dec.)

$^1$H-N.M.R.(CDCl$_3$, 400 MHz) δ 3.50(1H, d, J=2.9 Hz), 3.51(1H, d, J=5.6 Hz), 5.36(1H, dd, J=2.9, 5.6 Hz), 7.09–7.11(2H, m), 7.31–7.36(3H, m), 7.39–7.45(4H, m), 7.57–7.60(1H, m).

IR(KBr)νmax 3070, 3031, 1867, 1786, 1708 cm$^{-1}$

Example 6

Synthesis of (S)-3-benzoyl-4-benzyloxycarbonylethyl-2,5-oxazolidinedione (L-N-benzoyl-O-benzylglutamic acid-NCA) (Compound No. 17017)

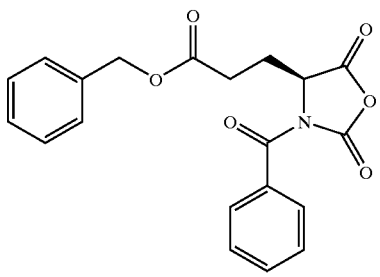

(17017)

In a similar manner as in Example 3, the title compound was obtained as white crystals (573 mg, 78%) by using benzoyl chloride (295 mg, 2.1 mmol), (S)-4-benzyloxycarbonylethyl-2,5-oxazolidinedione (L-N-benzoyl-O-benzylglutamic acid-NCA)(527 mg, 2.0 mmol), 4-dimethylaminopyridine (257 mg, 2.1 mmol) and ethyl acetate (32 mL).

Melting point: 94.5–94.9° C. (dec.)

$^1$H-N.M.R.(CDCl$_3$, 400 MHz) δ 2.47–2.50(2H, m), 2.53–2.63(2H, m), 5.09(1H, d, J=12.0 Hz), 5.14(1H, d, J=12.2 Hz), 5.21(1H, t, J=5.5 Hz), 7.32–7.39(5H, m), 7.43–7.47(2H, m), 7.61(1H, t, J=7.6 Hz), 7.69(2H, dd, J=1.2, 8.1 Hz).

IR(KBr)νmax 3258, 3065, 2964, 1869, 1805, 1731, 1701 cm$^{-1}$

Example 7

Synthesis of (S)-3-(p-methylbenzoyl)-4-methyl-2,5-oxazolidinedione (L-N-(p-methylbenzoyl)-alanine-NCA) (Compound No. 1026)

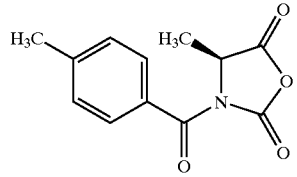

(1026)

p-Methylbenzoyl chloride (309 mg, 2.0 mmol) was dissolved in ethyl acetate (5 mL), followed by the addition of (S)-4-methyl-2,5-oxazolidinedione (L-alanine-NCA) (230 mg, 2.0 mmol) under ice cooling. Further, a solution of 4-dimethylaminopyridine (244 mg, 2.0 mmol) in ethyl acetate (10 mL) was added dropwise under ice cooling over 20 minutes. After the resulting mixture was stirred as was at 0° C. for 2 hours, a precipitated salt was filtered off, and the filtrate was concentrated under reduced pressure. The concentration residue was re-dissolved in a mixed solvent consisting of ethyl acetate (5 mL) and hexane (5 mL), and insoluble matter was filtered off. The filtrate was concentrated under reduced pressure to afford the title compound (152 mg, 33%) as a colorless clear syrup.

$^1$H-N.M.R.(CDCl$_3$, 400 MHz) δ 1.72(3H, d, J=7.1 Hz), 2.44(3H, s), 5.14(1H, q, J=7.1 Hz), 7.29(2H, d, J=8.1 Hz), 7.65(2H, d, J=8.3 Hz).

IR(KBr)νmax 3278, 2998, 2942, 1853, 1835, 1694 cm$^{-1}$

Example 8

Synthesis of (S)-3-(p-bromobenzoyl)-4-methyl-2,5-oxazolidinedione (L-N-(p-bromobenzoyl)-alanine-NCA) (Compound No. 1035)

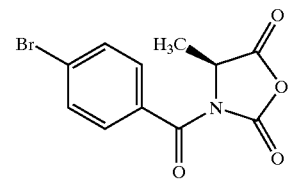

(1035)

In a similar manner as in Example 7, the title compound (238 mg, 40%) was obtained as a colorless clear syrup by using p-bromobenzoyl chloride (439 mg, 2.0 mmol), (S)-4-methyl-2,5-oxazolidinedione (L-alanine-NCA)(230 mg, 2.0 mmol), 4-dimethylaminopyridine (244 mg, 2.0 mmol) and ethyl acetate (15 mL).

$^1$H-N.M .R.(CDCl$_3$, 400 MHz) δ 1.74(3H, d, J=6.8 Hz), 5.13(1H, q, J=6.8 Hz), 7.61(2H, d, J=2.3 Hz), 7.63(2H, d, J=2.3 Hz).

IR(KBr)νmax 3350, 2998, 2942, 1855, 1840, 1698 cm$^{-1}$

Example 9

Synthesis of (S)-3-acetyl-4-methyl-2,5-oxazolidinedione (L-N-acetylalanine-NCA) (Compound No. 1001)

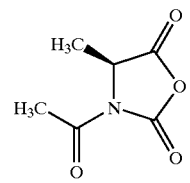

(1001)

(S)-4-methyl-2,5-oxazolidinedione (L-alanine-NCA) (345 mg, 3 mmol) was dissolved in ethyl acetate (20 mL), followed by the addition of acetyl chloride (306 mg, 3.9 mmol) under ice cooling. Further, a solution of N-methylmorpholine (394 mg, 3.9 mmol) in ethyl acetate (10 mL) was added dropwise under ice cooling over 20 minutes. After the resulting mixture was stirred as was at 0° C. for 2 hours, a precipitated salt was filtered off, and the filtrate was concentrated under reduced pressure. The concentration residue was re-dissolved in chloroform (5 mL), and insoluble matter was filtered off. The filtrate was concentrated under reduced pressure to afford the title compound (350 mg, 74%) as a colorless clear syrup.

$^1$H-N.M.R.(CDCl$_3$, 400 MHz) δ 1.69(3H, d, J=6.9 Hz), 2.59(3H, s), 4.80(1H, q, J=6.9 Hz).

IR(neat)νmax 3405, 2945, 1864, 1794, 1720 cm$^{-1}$

Example 10

Synthesis of (S)-3-acetyl-4-methyl-2,5-oxazolidinedione (L-N-acetylalanine-NCA) (Compound No. 1001)

(S)-4-methyl-2,5-oxazolidinedione (L-alanine-NCA) (345 mg, 3 mmol) was dissolved in ethyl acetate (20 mL), followed by the addition of acetyl chloride (306 mg, 3.9 mmol) under ice cooling. Further, a solution of 4-dimethylaminopyridine (476 mg, 3.9 mmol) in ethyl acetate (15 mL) was added dropwise under ice cooling over 20 minutes. After the resulting mixture was stirred as was at 0° C. for 2 hours, a precipitated salt was filtered off, and the filtrate was concentrated under reduced pressure. The concentration residue was re-dissolved in ethyl acetate (5 mL), and insoluble matter was filtered off. The filtrate was concentrated under reduced pressure to afford the title compound (118 mg, 25%) as a colorless clear syrup.

Example 11

Synthesis of (S)-3-decanoyl-4-methyl-2,5-oxazolidinedione (L-N-decanoylalanine-NCA) (Compound No. 1013)

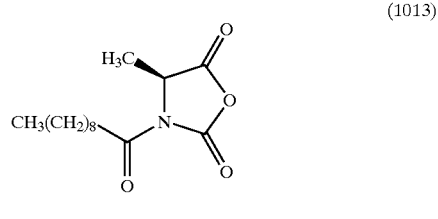

(1013)

(S)-4-methyl-2, 5-oxazolidinedione (L-alanine-NCA) (345 mg, 3 mmol) was dissolved in ethyl acetate (20 mL), followed by the addition of decanoyl chloride (744 mg, 3.9 mmol) under ice cooling. Further, a solution of N-methylmorpholine (394 mg, 3.9 mmol) in ethyl acetate (10 mL) was added dropwise under ice cooling over 20 minutes, and the resulting mixture was then stirred at the same temperature for 2 hours, the reaction mixture was treated in a similar manner as in Synthesis Process 5 of Example 8 to afford the title compound (525 mg, 65%) as a colorless clear syrup. A portion of the thus-obtained syrup was recrystallized from hexane to obtain white crystals (280 mg).

Melting point: 61–63° C.

$^1$H-N.M.R.(CDCl$_3$, 400 MHz) δ 0.88(3H, t, J=6.9 Hz), 1.27(12H, bs), 1.68(3H, d, J=7.3 Hz), 1.73–1.60(2H, m), 2.93(2H, t, J=7.6 Hz), 4.81(1H, q, J=7.3 Hz).

IR(KBr)νmax 2926, 2857, 1868, 1801, 1715 cm$^{-1}$

Example 12

Synthesis of (S)-3-(3-phenylpropanoyl)-4-methyl-2, 5-oxazolidinedione (L-N-(3-phenylpropanoyl)-alanine-NCA) (Compound No. 1019)

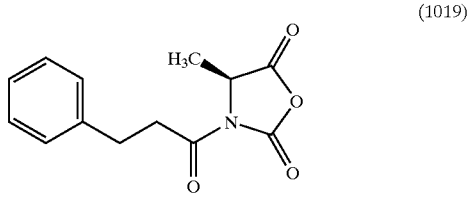

(1019)

(S)-4-methyl-2,5-oxazolidinedione (L-alanine-NCA) (345 mg, 3 mmol) was dissolved in ethyl acetate (20 mL), followed by the addition of 3-phenylpropanoyl chloride (658 mg, 3.9 mmol) under ice cooling. Further, a solution of N-methyl-morpholine (394 mg, 3.9 mmol) in ethyl acetate (10 mL) was added dropwise under ice cooling over 20 minutes, and the resulting mixture was then stirred at the same temperature for 2 hours. The reaction mixture was treated in a similar manner as in Synthesis Process 5 of Example 8 to afford the title compound (408 mg, 55%) as a colorless clear syrup.

$^1$H-N.M.R.(CDCl$_3$, 400 MHz) δ 1.64(3H, d, J=6.8 Hz), 3.03–2.99(2H, m), 3.29–3.19(2H, m), 4.78(1H, q, J=6.8 Hz), 7.32–7.18(5H, m).

IR(neat)νmax 3405, 2910, 2850, 1860, 1803, 1720 cm$^{-1}$

Example 13

Synthesis of N-benzoyl-L-alanyl-L-phenylalanine methyl ester (Compound No. 30)

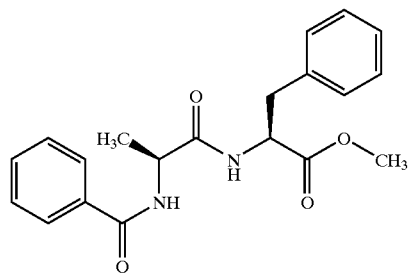

(30)

L-Phenylalanine methyl ester hydrochloride (518 mg, 2.4 mmol) was suspended in tetrahydrofuran (12 mL), and at 0° C., N-methylmorpholine (242 mg, 2.4 mmol) was added, followed by stirring for 20 minutes. (S)-3-Benzoyl-4-methyl-2,5-oxazolidinedione (N-benzoyl-L-alanine-NCA) (438 mg, 2 mmol) was added as crystals at 0° C. After the resulting mixture was stirred for 15 minutes, the mixture was allowed to rise in temperature to room temperature, at which the mixture was stirred for 15 minutes. The reaction mixture was poured into 1 N hydrochloric acid (25 mL), followed by extraction with ethyl acetate (25 mL). The organic layer was washed successively with a saturated aqueous solution of sodium hydrogencarbonate (25 mL) and a saturated aqueous solution of sodium chloride (25 mL), and was then dried over anhydrous magnesium sulfate. The organic layer was concentrated under reduced pressure. The resulting white solid was washed with hexane-ethyl acetate to afford the title compound (462 mg, 65%) as white crystals.

Melting point: 134–135° C.

$^1$H-N.M.R.(CDCl$_3$, 400 MHz) δ 1.45(3H, d, J=7.0 Hz), 3.05(1H, dd, J=13.9, 6.8 Hz), 3.16(1H, dd, J=13.9, 5.6 Hz), 3.74(3H, s,), 4.71(1H, quintet, J=7.0 Hz), 4.88–4.85(1H, m), 6.78–6.74(2H, m), 7.16–7.06(5H, m), 7.53–7.42(3H, m), 7.77(2H, d, J=7.0 Hz).

IR(KBr)νmax 3298, 3062, 3025, 2976, 2932, 1741, 1661, 1630, 1536, 1451 cm$^{-1}$

Example 14

Synthesis of N-benzoyl-L-alanine-(S)-1-(p-tolyl) ethylamide (Compound No. 31)

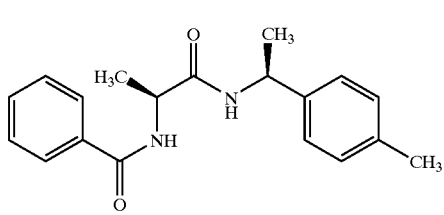

(31)

(S)-3-Benzoyl-4-methyl-2,5-oxazolidinedione (N-benzoyl-L-alanine-NCA) (110 mg, 0.50 mmol) was dissolved in ethyl acetate (2.5 mL), followed by the addition of a solution of (S)-1-(p-tolyl)ethylamine (68 mg, 0.50 mmol) in ethyl acetate (2.5 mL) at 0° C. A solution of N-methylmorpholine (61 mg, 0.6 mmol) in ethyl acetate (3.0 mL) was then added, followed by stirring for 30 minutes. The reaction mixture was poured into 1 N hydrochloric acid (10 mL), followed by extraction with ethyl acetate (10 mL). The organic layer was washed successively with a saturated aqueous solution of sodium hydrogencarbonate (10 mL) and a saturated aqueous solution of sodium chloride (10 mL), and was then dried over anhydrous magnesium sulfate. The organic layer was concentrated under reduced pressure to afford the title compound (149 mg, 97%) as white crystals.

Melting point: 158.6–160.1° C.

$^1$H-N.M.R.(CDCl$_3$, 400 MHz) δ 1.46(3H, d, J=7.2 Hz), 1.48(3H, d, J=6.8 Hz), 2.33(3H, s), 4.80 (1H, quintet, J=7.1 Hz), 5.06(1H, quintet, J=7.1 Hz), 7.15(2H, d, J=8.1 Hz), 7.25(2H, d, J=8.1 Hz), 7.40–7.43(1H, m), 7.43(2H, d, J=7.6 Hz), 7.79(2H, d, J=7.6 Hz).

IR(KBr)νmax 3308, 2978, 2935, 1660, 1639, 1603, 1580, 1527, 1490 cm$^{-1}$

Example 15

Synthesis of N-benzoyl-L-valine-(S)-1-(p-tolyl)ethylamide (Compound No. 32)

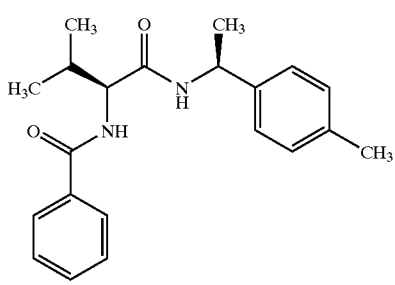

(32)

(S)-3-Benzoyl-4-isopropyl-2,5-oxazolidinedione (N-benzoyl-L-valine-NCA) (100 mg, 0.40 mmol) was dissolved in ethyl acetate (2.0 mL), followed by the addition of a solution of (S)-1-(p-tolyl)ethylamine (55 mg, 0.40 mmol) and N-methylmorpholine (61 mg, 0.60 mmol) in ethyl acetate (2.0 mL) at 0° C. The resulting mixture was stirred for 30 minutes. The reaction mixture was poured into 1 N hydrochloric acid (10 mL), followed by extraction with ethyl acetate (10 mL). The organic layer was washed successively with a saturated aqueous solution of sodium hydrogencarbonate (10 mL) and a saturated aqueous solution of sodium chloride (10 mL), and was then dried over anhydrous magnesium sulfate. The organic layer was concentrated under reduced pressure to afford the title compound (134 mg, 98%) as white crystals.

Melting point: 214.4–215.3° C.

$^1$H-N.M.R.(CDCl$_3$, 400 MHz) δ 0.95(3H, d, J=6.6 Hz), 0.96(3H, d, J=6.8 Hz), 1.42(3H, d, J=6.8 Hz), 2.13–2.21(1H, m), 2.33(3H, s), 4.53(1H, dd, J=8.5, 7.3 Hz), 5.06(1H, quintet, J=7.3 Hz), 6.70(1H, brd, J=7.8 Hz), 6.98(1H, brd, J=8.8 Hz), 7.14(2H, d, J=7.8 Hz), 7.21(2H, d, J=8.3 Hz), 7.41(2H, t, J=8.1 Hz), 7.50(1H, t, J=7.5 Hz), 7.79(2H, dd, J=8.1, 1.5 Hz).

IR(KBr)νmax 3284, 3059, 2970, 2927, 2871, 1654, 1633, 1579, 1541, 1490 cm$^{-1}$

Example 16

Synthesis of N-benzoyl-L-tert-leucine-(S)-1-(p-tolyl)ethylamide (Compound No. 33)

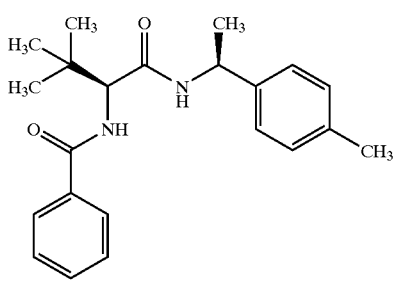

(33)

(S)-3-Benzoyl-4-tert-butyl-2,5-oxazolidinedione (N-benzoyl-L-tert-leucine-NCA)(100 mg, 0.38 mmol) was dissolved in ethyl acetate (2.0 mL), followed by the addition of a solution of (S)-1-(p-tolyl)ethylamine (52 mg, 0.38 mmol) in ethyl acetate (2.0 mL) at 0° C. The resulting mixture was stirred for 30 minutes. The reaction mixture was poured into 1 N hydrochloric acid (10 mL), followed by extraction with ethyl acetate (10 mL). The organic layer was washed successively with a saturated aqueous solution of sodium hydrogencarbonate (10 mL) and a saturated aqueous solution of sodium chloride (10 mL), and was then dried over anhydrous magnesium sulfate. The organic layer was concentrated under reduced pressure to afford the title compound (66 mg, 49%) as white crystals.

Melting point: 144.0–144.8° C.

$^1$H-N.M.R.(CDCl$_3$, 400 MHz) δ 1.00(9H, s), 1.43(3H, d, J=6.8 Hz), 2.34(3H, s), 4.51(1H, d, J=9.3 Hz), 5.07(1H, quintet, J=7.3 Hz), 6.38(1H, brd, J=7.6 Hz), 6.96(1H, brd, J=7.0 Hz), 7.14(2H, d, J=7.8 Hz), 7.21(2H, d, J=8.1 Hz), 7.43(2H, t, J=7.8 Hz), 7.51(1H, t, J=7.3 Hz), 7.79(2H, dd, J=8.3, 1.2 Hz).

IR(KBr)νmax 3274, 3065, 2968, 2872, 1636, 1579, 1525 cm$^{-1}$

Example 17

Synthesis of N-benzoyl-L-phenylalanine-(S)-1-(p-tolyl)ethylamide (Compound No. 34)

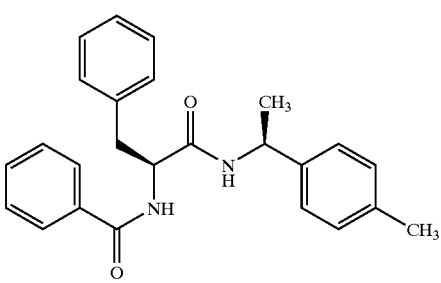

(34)

(S)-3-Benzoyl-benzoyl-2,5-oxazolidinedione (N-benzoyl-L-phenylalanine-NCA)(100 mg, 0.34 mmol) was dissolved in ethyl acetate (2.0 mL), followed by the addition of a solution of (S)-1-(p-tolyl)ethylamine (46 mg, 0.34 mmol) in ethyl acetate (2.0 mL) at 0° C. The resulting mixture was stirred for 30 minutes. The reaction mixture was poured into 1 N hydrochloric acid (10 mL), followed by extraction with ethyl acetate (10 mL). The organic layer was washed successively with a saturated aqueous solution of sodium hydrogencarbonate (10 mL) and a saturated aqueous solution of sodium chloride (10 mL), and was then dried over anhydrous magnesium sulfate. The organic layer was concentrated under reduced pressure to afford the title compound (110 mg, 84%) as white crystals.

Melting point: 214.2–214.9° C.

$^1$H-N.M.R.(CDCl$_3$, 400 MHz) δ 1.38(3H, d, J=7.1 Hz), 2.34(3H, s,), 3.05(1H, dd, J=13.4, 8.5 Hz), 3.20(1H, dd, J=13.4, 5.6 Hz), 4.82(1H, dt, J=8.3, 5.6 Hz), 4.99(1H, quintet, J=7.2 Hz), 6.03(1H, brd, J=7.8 Hz), 6.96(1H, brd, J=5.9 Hz), 6.98(1H, d, J=8.1 Hz), 7.09(1H, d, J=7.8 Hz), 7.14–7.17(1H, m), 7.18(4H, m), 7.42(2H, dt, J=7.8, 1.2 Hz), 7.50(1H, t, J=7.3 Hz), 7.74(2H, dd, J=8.3, 1.2 Hz).

IR(KBr)νmax 3289, 3063, 3030, 2974, 2926, 1653, 1632, 1604, 1579, 1541 cm$^{-1}$ Example 18

Synthesis of N-benzoyl-O-benzyl-L-glutamic acid-(S)-1-(p-tolyl)ethylamide (Compound No. 35)

(35)

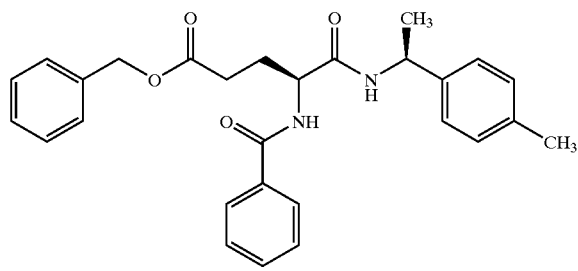

(S)-3-Benzoyl-4-benzyloxycarbonylethyl-2,5-oxazolidinedione (L-N-benzoyl-O-benzylglutamic acid-NCA)(100 mg, 0.27 mmol) was dissolved in ethyl acetate (2.0 mL), followed by the addition of a solution of (S)-1-(p-tolyl)ethylamine (37 mg, 0.27 mmol) and N-methylmorpholine (28 mg, 0.27 mmol) in ethyl acetate (2.0 mL) at 0° C. The resulting mixture was stirred for 30 minutes. The reaction mixture was poured into 1 N hydrochloric acid (10 mL), followed by extraction with ethyl acetate (10 mL). The organic layer was washed successively with a saturated aqueous solution of sodium hydrogencarbonate (10 mL) and a saturated aqueous solution of sodium chloride (10 mL), and was then dried over anhydrous magnesium sulfate. The organic layer was concentrated under reduced pressure to afford the title compound (106 mg, 85%) as white crystals.

Melting point: 123.4–124.9° C.

$^1$H-N.M.R.(CDCl$_3$, 400 MHz) δ 1.43(3H, d, J=7.1 Hz), 2.04–2.23(2H, m), 2.32(3H, s), 2.34–2.67(2H, m), 4.69–4.74(1H, m), 5.00–5.07(1H, m), 5.10(2H, s), 6.85–6.94(1H, m), 7.12(2H, d, J=8.2 Hz), 7.19(2H, d, J=8.2 Hz), 7.29–7.36(6H, m), 7.40–7.45(2H, m), 7.49–7.52(1H, m), 7.80(2H, dd, J=8.3, 1.2 Hz).

IR(KBr)νmax 3289, 3060, 3032, 2974, 2931, 1726, 1630, 1579, 1534 cm$^{-1}$

Example 19

Synthesis of N-acetyl-L-alanine-(S)-1-(p-tolyl) ethylamide (Compound No. 36)

(36)

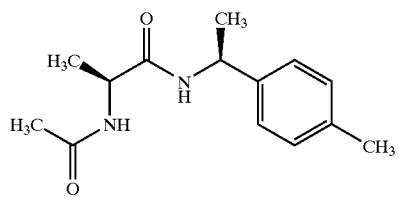

(S)-3-Acetyl-4-methyl-2,5-oxazolidinedione (N-acetyl-L-alanine-NCA)(424 mg, 2.7 mmol) was dissolved in ethyl acetate (10 mL), followed by the addition of (S)-1-(p-tolyl) ethylamine (406 mg, 3 mmol) at 0° C. The resulting mixture was stirred for 30 minutes. The reaction mixture was poured into 1 N hydrochloric acid (25 mL), followed by extraction with ethyl acetate (25 mL). The organic layer was washed successively with a saturated aqueous solution of sodium hydrogencarbonate (25 mL) and a saturated aqueous solution of sodium chloride (25 mL), and was then dried over anhydrous magnesium sulfate. The organic layer was concentrated under reduced pressure, and the resulting white solid was washed with hexane-ethyl acetate to afford the title compound (380 mg, 57%) as white crystals.

Melting point: 201–203° C.

$^1$H-N.M.R.(CDCl$_3$, 400 MHz) δ 1.32(3H, d, J=7.9 Hz), 1.44(3H, d, J=7.9 Hz), 1.98(3H, s), 2.32(3H, s), 4.54(1H, quintet, J=7.9 Hz), 5.01(1H, quintet, J=7.9 Hz), 6.48(1H, brd, J=7.9 Hz), 6.88(1H, brd, J=7.9 Hz), 7.20–7.10(4H, m).

IR(KBr)νmax 3292, 1633, 1546, 1444 cm$^{-1}$

Example 20

Synthesis of N-decanoyl-L-alanyl-L-phenylalanine methyl ester (Compound No. 37)

(37)

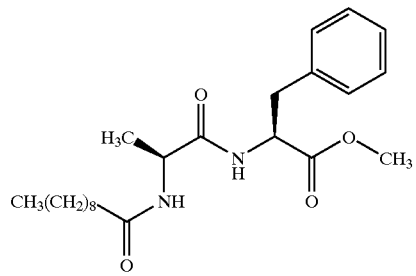

L-Phenylalanine methyl ester hydrochloride (259 mg, 1.2 mmol) was suspended in tetrahydrofuran (6 mL), followed by the addition of N-methylmorpholine (121 mg, 1.2 mmol) at 0° C. The resulting mixture was stirred for 20 minutes. (S)-3-Decanoyl-4-methyl-2,5-oxazolidinedione (N-decanoyl-L-alanine-NCA) (270 mg, 1 mmol) was added as crystals at 0° C., followed by stirring for 5 minutes. The mixture was allowed to rise in temperature to room temperature, at which the mixture was stirred for 30 minutes. The reaction mixture was treated in a similar manner as in Example 19 to afford the title compound (289 mg, 71%) as white crystals.

Melting point: 120–122° C.

¹H-N.M.R.(CDCl₃, 400 MHz) δ 0.88(3H, t, J=6.8 Hz), 1.30–1.25(12H, m), 1.32(3H, d, J=7.1 Hz), 1.61–1.58(2H, m), 2.15(2H, t, J=7.8 Hz), 3.06(1H, dd, J=6.6, 13.9 Hz), 3.14(1H, dd, J=5.6, 13.9 Hz), 3.72(3H, s), 4.50–4.44(1H, m), 4.85–4.80(1H, m), 6.00(1H, brd, J=7.8 Hz), 6.57(1H, brd, J=7.8 Hz), 7.11–7.09(2H, m), 7.30–7.23(3H, m).

IR(KBr)vmax 3298, 3061, 2923, 2852, 1750, 1644, 1541, 1453 cm⁻¹

Example 21

Synthesis of N-decanoyl-L-alanine-(S)-1-(p-tolyl)ethylamide (Compound No. 38)

(38)

(S)-3-Decanoyl-4-methyl-2,5-oxazolidinedione (N-decanoyl-L-alanine-NCA) (100 mg, 0.37 mmol) was dissolved in tetrahydrofuran (3 mL), and at 0° C., (S)-1-(p-tolyl)ethylamine (49 mg, 0.36 mmol) and N-methylmorpholine (37 mg, 0.36 mmol) were added, followed by stirring for 30 minutes. The reaction mixture was treated in a similar manner as in Example 19 to afford the title compound (103 mg, 77%) as white crystals.

Melting point: 153–154° C.

¹H-N.M.R.(CDCl₃, 400 MHz) δ 0.88(3H, t, J=6.8 Hz), 1.33–1.20(12H, m), 1.33(3H, d, J=6.8 Hz), 1.44(3H, d, J=6.8 Hz), 1.71–1.59(2H, m), 2.18(2H, t, J=7.2 Hz), 2.33(3H, s), 4.53(1H, quintet, J=6.8 Hz), 5.02(1H, quintet, J=6.8 Hz), 6.28(1H, brs), 6.84(1H, brs), 7.13(2H, d, J=8.1 Hz), 7.20 (2H, d, J=8.1 Hz).

IR(KBr)vmax 3297, 2920, 2852, 1638, 1556, 1452 cm⁻¹

Example 22

Synthesis of N-decanoyl-L-alaninebutylamide (Compound No. 39)

(39)

(S)-3-Decanoyl-4-methyl-2,5-oxazolidinedione (N-decanoyl-L-alanine-NCA) (270 mg, 1 mmol) was dissolved in tetrahydrofuran (6 mL), and at 0° C., butylamine (146 mg, 2 mmol) was added, followed by stirring for 30 minutes. The reaction mixture was treated in a similar manner as in Example 19 to afford the title compound (217 mg, 73%) as white crystals.

Melting point: 128–130° C.

¹H-N.M.R.(CDCl₃, 400 MHz) δ 0.88(3H, t, J=6.8 Hz), 0.92(3H, t, J=7.3 Hz), 1.36–1.26(14H, m), 1.36(3H, d, J=7.6 Hz), 1.52–1.45(2H, m), 1.63–1.57(2H, m), 2.23–2.15(2H, m), 3.27–3.21(2H, m), 4.51(1H, quintet, J=7.6 Hz), 6.34(1H, brd, J=7.6 Hz), 6.61(1H, brs).

IR(KBr)vmax 3295, 3096, 2959, 2925, 2853, 1634, 1545, 1468 cm⁻¹

Example 23

Synthesis of N-decanoyl-L-alaninemorpholinoamide (Compound No. 40)

(40)

(S)-3-Decanoyl-4-methyl-2,5-oxazolidinedione (N-decanoyl-L-alanine-NCA) (100 mg, 0.37 mmol) was dissolved in tetrahydrofuran (3 mL), and at 0° C., morpholine (52 mg, 0.6 mmol) was added, followed by stirring for 30 minutes. The reaction mixture was treated in a similar manner as in Example 19 to afford the title compound (112 mg, 97%) as a colorless clear syrup.

¹H-N.M.R.(CDCl₃, 400 MHz) δ 0.88(3H, t, J=6.9 Hz), 1.32–1.19(12H, m), 1.31(3H, d, J=7.8 Hz), 1.64–1.59(2H, m), 2.20(2H, t, J=7.6 Hz), 3.61–3.47(4H, m), 3.73–3.66(4H, m), 4.89(1H, quintet, J=7.8 Hz), 6.60–6.55(1H, m).

IR(neat)vmax 3308, 2926, 2856, 1637, 1535, 1466 cm⁻¹

INDUSTRIAL APPLICABILITY

The invention compounds represented by the formula (1) readily react with nucleophilic reagents such as free amines, and use of these compounds permits high-yield, mass and low-cost production of amino acid derivatives, optically active compounds, peptides, polypeptides or the like without racemization. The novel compounds and novel production processes according to the present invention, therefore, are extremely useful and are expected to find themselves as industrially-excellent compounds and processes in many fields led by the fields of pharmaceuticals and agrochemicals.

What is claimed is:

1. A compound of formula (1'):

(1)

wherein
  $R^1$ represents a substituted or unsubstituted alkyl group, a substituted or unsubstituted cycloalkyl group, a substituted or unsubstituted aralkyl group, a substituted or unsubstituted aryl group, a substituted or unsubstituted heterocycle, or a substituted or unsubstituted heterocyclic alkyl group:
  $R^{2'}$ represents an unsubstituted alkyl group, a substituted or unsubstituted cycloalkyl group, a substituted or unsubstituted aralkyl group, a substituted or unsubstituted aryl group, a substituted or unsubstituted heterocycle, or a substituted or unsubstituted heterocyclic alkyl group; with a proviso that a compound in which $R^{2'}$ is a 2-oxopropyl group, a compound of the following formula (2) is excluded.

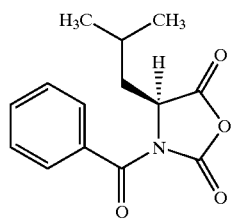

(2)

2. A process for the production of a compound of formula (1) according to claim 1, which comprises reacting, in an inert diluent and in the presence of a condensing agent, an amino acid N-carboxyanhydride represented by the following formula (4):

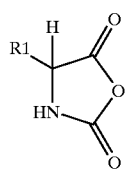

(4)

with a compound represented by the following formula (5):

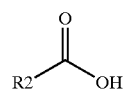

(5)

wherein $R^1$ represents a substituted or unsubstituted alkyl group, a substituted or unsubstituted cycloalkyl group, a substituted or unsubstituted aralkyl group, a substituted or unsubstituted aryl group, a substituted or unsubstituted heterocycle, or a substituted or unsubstituted heterocyclic alkyl group;

$R^{2'}$ represents an unsubstituted alkyl group, a substituted or unsubstituted cycloalkyl group, a substituted or unsubstituted aralkyl group, a substituted or unsubstituted aryl group, a substituted or unsubstituted heterocycle, or a substituted or unsubstituted heterocyclic alkyl group.

3. A process for the production of a compound of formula (1) according to claim 1, which comprises reacting, in an inert diluent and in the presence of an amine base, an amino acid N-carboxyanhydride represented by the following formula (4):

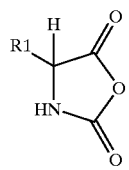

(4)

with a compound represented by the following formula (6):

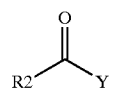

(6)

wherein $R^1$ represents a substituted or unsubstituted alkyl group, a substituted or unsubstituted cycloalkyl group, a substituted or unsubstituted aralkyl group, a substituted or unsubstituted aryl group, a substituted or unsubstituted heterocycle, or a substituted or unsubstituted heterocyclic alkyl group;

$R^{2'}$ represents an unsubstituted alkyl group, a substituted or unsubstituted cycloalkyl group, a substituted or unsubstituted aralkyl group, a substituted or unsubstituted aryl group, a substituted or unsubstituted heterocycle, or a substituted or unsubstituted heterocyclic alkyl group, and Y represents a halogen atom.

4. A compound of formula (1') according to claim 1 wherein $R^{2'}$ is an unsubstituted alkyl group, a substituted or unsubstituted cycloalkyl group, or a substituted or unsubstituted aralkyl group.

5. A compound of formula (1') according to claim 1, wherein $R^{2'}$ is an unsubstituted alkyl group.

6. A compound of formula (1') according to claim 1, wherein $R^{2'}$ is a substituted or unsubstituted heterocycle or a substituted or unsubstituted heterocyclic alkyl group.

7. A compound of formula (1') according to claim 1, wherein $R^1$ is a side chain on an a-carbon atom of a protected or unprotected amino acid.

8. A process for the production of an amide derivative represented by the following formula (8):

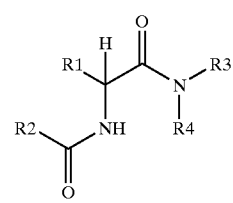

(8)

wherein $R^1$ and $R^2$ each independently represents a unsubstituted alkyl group, a substituted or unsubstituted cycloalkyl group, a substituted or unsubstituted aralkyl group, a substituted or unsubstituted aryl group, a substituted or unsubstituted heterocycle, or a substituted or unsubstituted heterocyclic alkyl group, with a proviso that a compound in which $R^2$ is a 2-oxopropyl group, a compound of the following formula (2) or a compound of the following formula (3) is excluded:

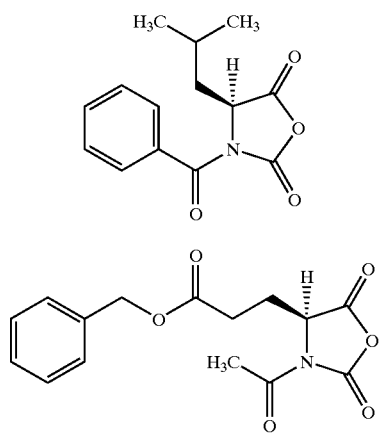

$R^3$ and $R^4$ each independently represents a hydrogen atom, a substituted or unsubstituted alkyl group, a substituted or unsubstituted cycloalkyl group, a substituted or unsubstituted aralkyl group, a substituted or unsubstituted aryl group, a substituted or unsubstituted heterocycle, or a substituted or unsubstituted heterocyclic alkyl group, which comprises a step of reacting a compound of formula (1):

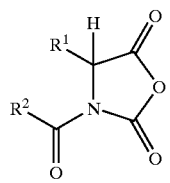

wherein $R^1$ and $R^2$ have the same meanings as defined above, with an amine derivative represented by the following formula (7):

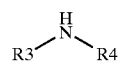

wherein $R^3$ and $R^4$ have the same meanings as defined above.

9. A process for the production of an amide derivative represented by the following formula (8):

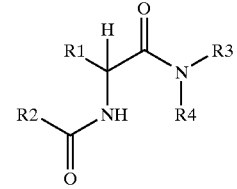

wherein $R^1$ and $R^2$ each independently represents a substituted or unsubstituted alkyl group, a substituted or unsubstituted cycloalkyl group, a substituted or unsubstituted aralkyl group, a substituted or unsubstituted aryl group, a substituted or unsubstituted heterocycle, or a substituted or unsubstituted heterocyclic alkyl group, with a proviso that a compound in which $R^2$ is a 2-oxopropyl group, a compound of the following formula (2) or a compound of the following formula (3) is excluded:

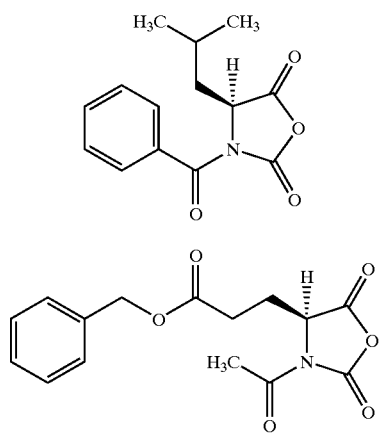

$R^3$ and $R^4$ each independently represents a hydrogen atom, a substituted or unsubstituted alkyl group, a substituted or unsubstituted cycloalkyl group, a substituted or unsubstituted aralkyl group, a substituted or unsubstituted aryl group, a substituted or unsubstituted heterocycle, or a substituted or unsubstituted heterocyclic alkyl group, which comprises a step of reacting a compound of formula (1):

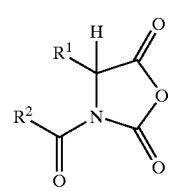

wherein $R^1$ and $R^2$ have the same meanings as defined above, with a protected or unprotected amino acid.

* * * * *